United States Patent [19]
Lollar et al.

[11] Patent Number: 5,888,974
[45] Date of Patent: Mar. 30, 1999

[54] HYBRID HUMAN/ANIMAL FACTOR VIII

[75] Inventors: John S. Lollar, Decatur, Ga.;
Marschall S. Runge, Galveston, Tex.

[73] Assignee: Emory University, Atlanta, Ga.

[21] Appl. No.: 475,201

[22] Filed: Jun. 7, 1995

Related U.S. Application Data

[63] Continuation-in-part of PCT/US94/13200, Nov. 15, 1994 which is a continuation of Ser. No. 212,133, Mar. 11, 1994, Pat. No. 5,663,060, which is a continuation-in-part of Ser. No. 864,004, Apr. 7, 1992, Pat. No. 5,364,771.

[51] Int. Cl.$^6$ .......................... A61K 38/37; C07K 14/755
[52] U.S. Cl. ............................... 514/12; 514/2; 514/834; 530/383; 930/100
[58] Field of Search .................... 514/2, 12, 834; 530/383; 930/100

[56] References Cited

U.S. PATENT DOCUMENTS

| | | | |
|---|---|---|---|
| Re. 32,011 | 10/1985 | Zimmerman et al. | 530/383 |
| 4,554,101 | 11/1985 | Hopp | 530/324 |
| 4,757,006 | 7/1988 | Toole et al. | 435/69.6 |
| 4,868,112 | 9/1989 | Toole, Jr. | 514/8 |
| 4,965,199 | 10/1990 | Capon et al. | 435/69.6 |
| 4,970,300 | 11/1990 | Fulton et al. | 530/383 |
| 4,980,456 | 12/1990 | Scandella et al. | 530/383 |
| 5,004,803 | 4/1991 | Kaufman et al. | 530/383 |
| 5,149,637 | 9/1992 | Scandella et al. | 435/69.6 |
| 5,171,844 | 12/1992 | Van Ooyen et al. | 530/383 |
| 5,246,850 | 9/1993 | Bennett et al. | 435/69.6 |
| 5,422,260 | 6/1995 | Kaufman et al. | 435/212 |
| 5,563,045 | 10/1996 | Pittman | 435/69.6 |
| 5,618,788 | 4/1997 | Capon et al. | 514/12 |
| 5,618,789 | 4/1997 | Capon et al. | 514/12 |
| 5,633,150 | 5/1997 | Wood et al. | 435/69.6 |

FOREIGN PATENT DOCUMENTS

| | | |
|---|---|---|
| 0 306 968 A2 | 9/1988 | European Pat. Off. |
| 91/07438 | 5/1990 | WIPO |
| WO 91/09122 | 6/1991 | WIPO |
| WO 92/16557 | 10/1992 | WIPO |
| WO 94/11503 | 5/1994 | WIPO |

OTHER PUBLICATIONS

Lollar, P. et al. (1994) "Inhibition of Human Factor VIIIa by Anti–A2 Subunit Antibodies" *J. Clin. Invest.* 93:2497–2504.
Gilles, Jean Guy and J.–M. R. Saint–Remy (1994) "Healthy Subjects Produce both Anti–Factor VIII and Specific Anti––Idiotype Antibodies" *J. Clin. Invest.* 94:1496–1505.
Hoyer, L.W. and D. Scandella (1994) "Factor VIII Inhibitors: Structure and Function in Autoantibody and Hemophilia A Patients" *Seminars in Hematology* 31(2)(4):1–5.
Brinkhous, K.M. et al., "Purified Human Factor VIII Procoagulant Protein: Comparative Hemostatic Resonce After Infusions into Hemophilia and von Willebrand Disease Dogs" *Proc. Natl. Acad. Sci. U.S.A.*, 82:8752–8755 (1985).
Elder, B., et al., "Sequence of the Murine Factor VIII cDNA", *Genomics*, 16(2):374–379 (1993).
Hoeben, R.C., "Expression of Functional Factor VIII in Primary Human Skin Fibroblasts After Retrovirus–mediated Gene Transfer", *J. Biol. Chem.*, 265(13):7318–7323 (1990).
Scandella, D., et al., "Localization of Epitopes for Human Factor VIII Inhibitor Antibodies by Immunoblotting and Antibody Neutralization," 111 (25) *Chem. Abst.* 570, Abst. 230240 (Dec. 18, 1989).
Scandella, D., et al., "Localization of Epitopes for Human Factor VIII Inhibitor Antibodies by Immunoblotting and Antibody Neutralization," 82 (6) *Blood* 1767–1775 (1993).
Scandella, D. et al., "A Recombinant Factor VIII A2 Domain Polypeptide Quantitatively Neutralizes Human Inhibitor Antibodies that Bind to A2," 121 (19) *Chem. Abst.* 782, Abst. 268801 (Dec. 20, 1993).
Arai, M., et al., "Molecular basis of factor VIII inhibition by human antibodies," 83 *J. Clin. Invest.* 1978–1984 (1989).
Burke, R.L., et al., "The functional domains of coagulation factor VIII:C," 261 J. Biol. Chem. 12574–12578 (1986).
Eaton, D., et al., "Proteolytic processing of human factor VIII. Correlation of specific cleavages by thrombin, factor Xa, and activated protein C with activation and inactivation of factor VIII coagulant activity," 25 *Biochem.* 505–512 (1986).

(List continued on next page.)

*Primary Examiner*—Dian C. Jacobson
*Attorney, Agent, or Firm*—Greenlee Winner and Sullivan PC

[57] ABSTRACT

A hybrid procoagulant factor VIII is produced by isolation and recombination of human and other nonhuman mammalian factor VIII subunits or domains, or by genetic engineering of the human and animal factor VIII genes. Subunits or domains of factor VIII that have been purified from human or animal plasma are isolated, and hybrid human/animal factor VIII is produced by (1) mixing either animal heavy chain subunits with human light chain subunits or by mixing human heavy chain subunits with animal light chain subunits, thereby producing human light chain/animal heavy chain and human heavy chain/animal light chain hybrid molecules; or by (2) mixing one or more domains of one species with one or more domains of the other species. These hybrid molecules are isolated by ion exchange chromatography. Alternatively, recombinant DNA methods are used to change elements of animal factor VIII or human factor VIII to the corresponding elements of human factor VIII or animal factor VIII, respectively, to produce hybrid human/animal factor VIII. A recombinant hybrid equivalent factor VIII molecule is produced by substituting amino acid sequence having no known factor VIII sequence identity for specific amino acid sequence in the human or animal factor VIII. The hybrid factor VIII and hybrid equivalent factor VIII molecules are administered to patients having factor VIII deficiency.

2 Claims, 2 Drawing Sheets

OTHER PUBLICATIONS

Hoeben, R.C., et al., "Toward Gene Therapy for Hemophilia A: Long–Term Persistence for Factor VIII–Secreting Fibroblasts After Transplantation into Immunodeficient Mice", *Human Gene Therapy,* 4(2):179–186 (1993).

Horton, R.M., et al., "Gene Splicing by Overlap Extension", *Meth. Enzymol.,* 217:270 (1993).

Levinson, B., et al., "Sequence of the Human Factor VII-I–Associated Gene is Conserved in Mouse", *Genomics,* 13:862–865 (1992).

Lollar, P., et al., "Inhibition of Human Factor VIIIa by Anti–A2 Subunit Antibodies", *Blood,* 82:Abstract No. 230 (1993).

Lollar, P., et al., "Coagulant Properties of Hybrid Human-–Porcine Factor VIII Molecules", *J. Biol. Chem.,* 267:23652–23657 (1992).

Lubin, I.M., et al., "Elimination of a Major Inhibitor Epitope in Factor VIII", *J. Biol. Chem.,* 269(12):8639–8641 (1994).

Lubin, L.M., et al., "Expression of a Recombinant Hybrid Human/Porcine Factor VIII Molecule with Elimination of Reactivity Toward an Inhibitory Anti–Human A2 Domain Antibody", *Blood,* 82:Abstract 229 (1993).

Lusher, J.M., et al., "Recombinant Factor VIII for the Treatment of Previously Untreated Patients with hemophilia A", *New. Engl. J. Med.,* 328(7):453–459 (1993).

Pittman, D.D., et al., "A2 Domain of Human Recombinant-–Derived Factor VIII is Required for Procoagulant Activity but not for Thrombin Cleavage", *Blood,* 79(2):389–397 (1992).

Rebemtulla, A., "Improved Procoagulant Activity of Human Factor VIII Molecules Containing Portions of Porcine Sequence", *Blood,* 82:Abstract 1339 (1993).

Sarkar, G., et al., "Access to a Messenger RNA Sequence or its Protein Product is not Limited by Tissue or Species Specificity", *Science,* 244:331–334 (1989).

Shime, M., et al., "Factor VIII Neutralizing Monoclonal Antibody and a Human Inhibitor Alloantibody Recognizing Epitopes in the C2 Domain Inhibit Binding to von Willebrand Factor and to Phosphatidyl Serine", *Thromb. Haemostas.,* 69:240–246 (1993).

Eaton, D.L., et al., "Construction and characterization of an active factor VIII variant lacking the central one–third of the molecule," 25 *Biochem.* 8343–8347 (1986).

Eaton, D.L., et al., "Characterization of recombinant human factor VIII," 262 *J. of Biol. Chem.* 3285–3290 (1987).

Fass, D.N., et al., "Monoclonal antibodies to porcine factor VIII coagulant and their use in the isolation of active coagulant protein," 59 *Blood* 594–600 (1982).

Fay, P.J., et al., "The size of human factor VIII heterodimers and the effects produced by thrombin," 871 *Biochimica et Biophysica Acta* 268–278 (1986).

Fay, P.J., "Subunit structure of thrombin–activated human factor VIIIa," 952 *Biochimica et Biophysica Acta* 181–190 (1987).

Fay, P.J., "Reconstitution of human factor VIII from isolated subunits," 262 *Arch. Biochem. Biophys.* 525–531 (1988).

Fay, P.J., et al., "Topography of the human factor VIII–von Willebrand factor complex," 265 *J. Biol. Chem.* 6197–6202 (1990).

Fay, P.J., et al., "von Willebrand factor mediates protection of factor VIII from activated protein C–catalyzed inactivation," 266 *J. Biol. Chem.* 2172–2177 (1991).

Fay, P.J., et al., "Human factor VIII subunit structure," 266 *J. Biol. Chem.* 1–6 (1991).

Fulcher, C.A., and T.S. Zimmerman, "Characterization of the human factor VIII procoagulant protein with a heterologous precipitating antibody," 79 *Proc. Nat'l. Acad. Sci. U.S.A.* 1648–1652 (1982).

Fulcher, C.A., et al., "Human factor VIII procoagulant protein," 76 *J. Clin. Invest.* 117–124 (1985).

Gitschier, J., et al., "Characterization of the human factor VIII gene," 312 *Nature* 326–330 (1984).

Hill–Eubanks, D.C., and P. Lollar, "von Willebrand factor is a cofactor for thrombin–catalyzed cleavage of the factor VIII light chain," 265 *J. Biol. Chem.* 17854–17858 (1990).

Kaufman, R.J., et al., "Synthesis, processing, and secretion of recombinant human factor VIII expressed in mammalian cells," 263 *J. Biol. Chem.* 6352–6362 (1988).

Kaufman, R.J., et al., "Effect of von Willebrand factor coexpression on the synthesis and secretion of factor VIII in Chinese hamster ovary cells," 9 *Molec. Cell. Biol.* 1233–1242 (1989).

Koedam, J.A., et al., "The effect of von Willebrand factor on activation of factor VIII by factor Xa," 189 *Eur. J. Biochem.* 229–234 (1990).

Kohn, D.B., and P.W. Kantoff, "Potential applications of gene therapy," 29 *Transfusion* 812–820 (1989).

Leyte, A., et al., "Sulfation of Tyr$^{1000}$ of human blood coagulation factor VIII is essential for the interaction of factor VIII with von Willebrand factor," 266 *J. Biol. Chem.* 740–746 (1991).

Lollar, P., et al., "Activation of porcine factor VIII:C by thrombin and factor Xa," 24 *Biochemistry* 8056–8064 (1985).

Lollar, P. (J.S.), et al., "Association of the factor VIII light chain with von Willebrand factor," 263 *J. Biol. Chem.* 10451 (1988).

Lollar, P. (J.S.), et al., "Molecular characterization of commercial porcine factor VIII concentrate," 71 *Blood* 137–143 (1988).

Lollar, P. (J.S.), and C.G. Parker, "Subunit structure of thrombin–activated porcine factor VIII," 28 *Biochemistry* 666–674 (1989).

Lollar, P., and C.G. Parker, "pH–dependent denaturation of thrombin–activated porcine factor VIII," 265 *J. Biol. Chem.* 1688–1692 (1990).

Lollar, P., "The association of factor VIII with von Willebrand factor," 66 *Mayo Clin. Proc.* 542–534 (1991).

Lollar, P., and E.T. Parker, "Structural basis for the decreased procoagulant activity of human factor VIII compared to the porcine homolog," 266 *J. Biol. Chem.* 12481–12486 (1991).

Mosesson, M.W., et al., "Structural model of porcine factor VIII and factor VIIIa molecules based on scanning transmission electron microscope (STEM) images and STEM mass analysis," 85 *J. Clin. Invest.* 1983–1990 (1990).

Neylor, J.A., et al., "Detection of three novel mutations in two haemophilia A patients by rapid screening of whole essential region of factor VIII gene," 337 *The Lancet* 635–639 (1991).

Pittman, D.D., and R.J. Kaufman, "Proteolytic requirements for thrombin activation of anti–hemophilic factor (factor VIII)," 85 *Proc. Nat'l. Acad. Sci. U.S.A.* 2429–2433 (1988).

Roberts, H.R., and M.R. Jones, "Hemophilia and related conditions—Congenital deficiencies of prothrombin (factor 1M, factor V, and factors VII to XII," Ch. 153, 1453–1474, 1460, in *Hematology,* Williams, W.J., et al., ed., 1990.

Toole, J.J., et al., "Molecular cloning of a cDNA encoding human antihaemophilic factor," 312 *Nature* 342–347 (1984).

Toole, J.J., et al., "A large region (≈95 kDa) of human factor VIII is dispensable for in vitro procoagulant activity," 83 *Proc. Nat'l. Acad. Sci. U.S.A.* 5939–5942 (1986).

Vehar, G.A., and E.W. Davie, "Preparation and properties of bovine factor VIII (antihemophilic factor)," 19 *Biochem.* 401–410 (1980).

Vehar, G.A., et al., "Structure of human factor VIII," 312 *Nature* 337–342 (1984).

Walker, F.J., et al., "Identification of the binding site for activated protein C on the light chain of factors V and VIII," 265 *J. Biol. Chem.* 1484–1489 (1990).

Ware, J., et al., "Localization of a factor VIII–inhibiting antibody epitope to a region between residues 338 and 362 of factor VIII heavy chain," 85 *Proc. Natl. Acad. Sci. USA* 3165–3169 (1988).

Wood, W.I., et al., "Expression of active human factor VIII from recombinant DNA clones," 312 *Nature* 330–337 (1984).

Scandalla, D. et al., "A Recombinant Factor VIII A2 Domain Polypeptide Quantitatively Neutralizes Human Inhibitor Antibodies that Bind to A2," 74 (5) *Blood* 1618–1626 (1989).

FIGURE 1A

```
                1
     373        ↓
Pig  SVAKKHPKTWVHYISAEEEDWDYAPAVPSPSDRSYKSLYLNSGPQRIGRKYKKARFVAYT        432
Hum  SVAKKHPKTWVHYIAAEEEDWDYAPLVLAPDDRSYKSQYLNNGPQRIGRKYKKVRFMAYT        432
     ***** ***** ***   ******** *  **** *** *** ********* ** ***
Mou  SVAKKYPKTWIHYISAEEEDWDYAPSVPTSDNGSYKSQYLSNGPHRIGRKYKKVRFIAYT        432

2                                                3
        ↓                                                ↓
Pig  DVTFKTRKAIPYESGILGPLLYGEVGDTLLIIFKNKASRPYNIYPHGITDVSALHPGRLL        492
Hum  DETFKTREAIQHESGILGPLLYGEVGDTLLIIFKNQASRPYNIYPHGITDVRPLYSRRLP        492
     * ***** ** **************************** ************   *  **
Mou  DETFKTRETIQHESGLLGPLLYGEVGDTLLIIFKNQASRPYNIYPHGITDVSPLHARRLP        492

4
           ↓
Pig  KGWKHLKDMPILPGETFKYKWTVTVEDGPTKSDPRCLTRYYSSSINLEKDLASGLIGPLL        552
Hum  KGVKHLKDFPILPGEIFKYKWTVTVEDGPTKSDPRCLTRYYSSFVNMERDLASGLIGPLL        552
     ** ***** ****** ************************** *  * *********
Mou  RGIKHVKDLPIHPGEIFKYKWTVTVEDGPTKSDPRCLTRYYSSFINPERDLASGLIGPLL        552

5
                                       ↓
Pig  ICYKESVDQRGNQMMSDKRNVILFSVFDENQSWYLAENIQRFLPNPDGLQPQDPEFQASN        612
Hum  ICYKESVDQRGNQIMSDKRNVILFSVFDENRSWYLTENIQRFLPNPAGVQLEDPEFQASN        612
     *************  *************** **** ******** * *  * ******
Mou  ICYKESVDQRGNQMMSDKRNVILFSIFDENQSWYITENMQRFLPNAAKTQPQDPGFQASN        612
```

FIGURE 1B

```
Pig  IMHSINGYVFDSLQLSVCLHEVAYWYILSVGAQTDFLSVFFSGYTFKHKMVYEDTLTLFP      672
Hum  IMHSINGYVFDSLQLSVCLHEVAYWYILSIGAQTDFLSVFFSGYTFKHKMVYEDTLTLFP      672
     ********** * ************** ********* ********************
Mou  IMHSINGYVFDSLELTVCLHEVAYWHILSVGAQTDFLSIFFSGYTFKHKMVYEDTLTLFP      672

6                7
Pig  FSGETVFMSMENPGLWVLGCHNSDLRNRGMTALLKVYSCDRDIGDYYDNTYEDIPGFLLS      732
Hum  FSGETVFMSMENPGLWILGCHNSDFRNRGMTALLKVSSCDKNTGDYYEDSYEDISAYLLS      732
     *************** ******* ************  *** * *** *  ****  *
Mou  FSGETVFMSMENPGLWVLGCHNSDFRKRGMTALLKVSSCDKSTSDYYEEIYEDIPTQLVN      732

Pig  GKNVIEPR                                                          740
Hum  KNNAIEPR                                                          740
       ** * **
Mou  ENNVIDPR                                                          740
```

HYBRID HUMAN/ANIMAL FACTOR VIII

This application is a continuation-in-part of PCT/USC94/13200; filed Nov. 15, 1994, which is continuation-in-part of Ser. No. 08/212,133, filed Mar. 11, 1994, now U.S. Pat. No. 5,663,060, which is a continuation-in-part of Ser. No. 07/864,004, filed Apr. 7, 1992, now U.S. Pat. No. 5,364,771.

The government has rights in this invention arising from National Institutes of Health Grant Nos. HL40921, HL46215, and HL36094 that partially funded the research leading to this invention.

BACKGROUND OF THE INVENTION

This invention relates generally to a hybrid factor VIII having human and animal factor VIII amino acid sequence or having human factor VIII and non-factor VIII amino acid sequence and methods of preparation and use thereof.

Blood clotting begins when platelets adhere to the cut wall of an injured blood vessel at a lesion site. Subsequently, in a cascade of enzymatically regulated reactions, soluble fibrinogen molecules are converted by the enzyme thrombin to insoluble strands of fibrin that hold the platelets together in a thrombus. At each step in the cascade, a protein precursor is converted to a protease that cleaves the next protein precursor in the series. Cofactors are required at most of the steps.

Factor VIII circulates as an inactive precursor in blood, bound tightly and non-covalently to von Willebrand factor. Factor VIII is proteolytically activated by thrombin or factor Xa, which dissociates it from von Willebrand factor and activates its procoagulant function in the cascade. In its active form, the protein factor VIIIa is a cofactor that increases the catalytic efficiency of factor IXa toward factor X activation by several orders of magnitude.

People with deficiencies in factor VIII or antibodies against factor VIII who are not treated with factor VIII suffer uncontrolled internal bleeding that may cause a range of serious symptoms, from inflammatory reactions in joints to early death. Severe hemophiliacs, who number about 10,000 in the United States, can be treated with infusion of human factor VIII, which will restore the blood's normal clotting ability if administered with sufficient frequency and concentration. The classic definition of factor VIII, in fact, is that substance present in normal blood plasma that corrects the clotting defect in plasma derived from individuals with hemophilia A.

The development of antibodies ("inhibitors" or "inhibitory antibodies") that inhibit the activity of factor VIII is a serious complication in the management of patients with hemophilia. Autoantibodies develop in approximately 20% of patients with hemophilia A in response to therapeutic infusions of factor VIII. In previously untreated patients with hemophilia A who develop inhibitors, the inhibitor usually develops within one year of treatment. Additionally, autoantibodies that inactivate factor VIII occasionally develop in individuals with previously normal factor VIII levels. If the inhibitor titer is low enough, patients can be managed by increasing the dose of factor VIII. However, often the inhibitor titer is so high that it cannot be overwhelmed by factor VIII. An alternative strategy is to bypass the need for factor VIII during normal hemostasis using factor IX complex preparations (for example, KONYNEO®, Proplex®) or recombinant human factor VIIIa. Additionally, since porcine factor VIII usually has substantially less reactivity with inhibitors than human factor VIII, a partially purified porcine factor VIII preparation (HYATE:C®) is used. However, inhibitors may develop to porcine factor VIII after one or more infusions.

Several preparations of human plasma-derived factor VIII of varying degrees of purity are available commercially for the treatment of hemophilia A. These include a partially-purified factor VIII derived from the pooled blood of many donors that is heat- and detergent-treated for viruses but contains a significant level of antigenic proteins; a monoclonal antibody-purified factor VIII that has lower levels of antigenic impurities and viral contamination; and recombinant human factor VIII, clinical trials for which are underway. Unfortunately, human factor VIII is unstable at physiologic concentrations and pH, is present in blood at an extremely low concentration (0.2 $\mu$g/ml plasma), and has low specific clotting activity.

Hemophiliacs require daily replacement of factor VIII to prevent bleeding and the resulting deforming hemophilic arthropathy. However, supplies have been inadequate and problems in therapeutic use occur due to difficulty in isolation and purification, immunogenicity, and the necessity of removing the AIDS and hepatitis infectivity risk. The use of recombinant human factor VIII or partially-purified porcine factor VIII will not resolve all the problems.

The problems associated with the commonly used, commercially available, plasma-derived factor VIII have stimulated significant interest in the development of a better factor VIII product. There is a need for a more potent factor VIII molecule so that more units of clotting activity can be delivered per molecule; a factor VIII molecule that is stable at a selected pH and physiologic concentration; a factor VIII molecule that is less apt to cause production of inhibitory antibodies; and a factor VIII molecule that evades immune detection in patients who have already acquired antibodies to human factor VIII.

It is therefore an object of the present invention to provide a factor VIII that corrects hemophilia in a patient deficient in factor VIII or having inhibitors to factor VIII.

It is a further object of the present invention to provide methods for treatment of hemophiliacs.

It is still another object of the present invention to provide a factor VIII that is stable at a selected pH and physiologic concentration.

It is yet another object of the present invention to provide a factor VIII that has greater coagulant activity than human factor VIII.

It is an additional object of the present invention to provide a factor VIII against which less antibody is produced.

SUMMARY OF THE INVENTION

The present invention provides isolated, purified, hybrid factor VIII molecules and fragments thereof with coagulant activity including hybrid factor VIII having factor VIII amino acid sequence derived from human and pig or other non-human mammal (together referred to herein as "animal"); or in a second embodiment including a hybrid equivalent factor VIII having factor VIII amino acid sequence derived from human or animal or both and amino acid sequence having no known sequence identity to factor VIII ("non-factor VIII amino acid sequence"), preferably substituted in an antigenic and/or immunogenic region of the factor VIII, is described. One skilled in the art will realize that numerous hybrid factor VIII constructs can prepared including, but not limited to, human/animal factor VIII having greater coagulant activity than human factor VIII ("superior coagulant activity"); non-immunogenic human/equivalent factor VIII; non-antigenic human/equivalent or human/animal factor VIII; non-immunogenic human/animal or human/equivalent factor VIII having superior coagulant activity; non-antigenic human/animal or human/animal/equivalent factor VIII having superior coagulant activity; non-immunogenic, non-antigenic human/equivalent or human/equivalent/animal factor VIII; and non-immunogenic, non-antigenic human/animal/equivalent factor VIII having superior coagulant activity.

The hybrid factor VIII molecule is produced by isolation and recombination of human and animal factor VIII subunits or domains; or by genetic engineering of the human and animal factor VIII genes.

In a preferred embodiment, recombinant DNA methods are used to substitute elements of animal factor VIII for the corresponding elements of human factor VIII, resulting in hybrid human/animal factor VIII molecules. In a second preferred embodiment, recombinant DNA methods are used to replace one or more amino acids in the human or animal factor VIII or in a hybrid human/animal factor VIII with amino acids that have no known sequence identity to factor VIII, preferably a sequence of amino acids that has less immunoreactivity with naturally occurring inhibitory antibodies to factor VIII ("nonantigenic amino acid sequence") and/or is less apt to elicit the production of antibodies to factor VIII ("non-immunogenic amino acid sequence") than human factor VIII. An example of an amino acid sequence that can be used to replace immunogenic or antigenic sequence is a sequence of alanine residues.

In another embodiment, subunits of factor VIII are isolated and purified from human or animal plasma, and hybrid human/animal factor VIII is produced either by mixture of animal heavy chain subunits with human light chain subunits or by mixture of human heavy chain subunits with animal light chain subunits, thereby producing human light chain/animal heavy chain and human heavy chain/animal light chain hybrid molecules. These hybrid molecules are isolated by ion exchange chromatography.

Alternatively, one or more domains or partial domains of factor VIII are isolated and purified from human or animal plasma, and hybrid human/animal factor VIII is produced by mixture of domains or partial domains from one species with domains or partial domains of the second species. Hybrid molecules can be isolated by ion exchange chromatography.

Methods for preparing highly purified hybrid factor VIII are described having the steps of: (a) isolation of subunits of plasma-derived human factor VIII and subunits of plasma-derived animal factor VIII, followed by reconstitution of coagulant activity by mixture of human and animal subunits, followed by isolation of hybrid human/animal factor VIII by ion exchange chromatography; (b) isolation of domains or partial domains of plasma-derived human factor VIII and domains or partial domains of plasma-derived animal factor VIII, followed by reconstitution of coagulant activity by mixture of human and animal domains, followed by isolation of hybrid human/animal factor VIII by ion exchange chromatography; (c) construction of domains or partial domains of animal factor VIII by recombinant DNA technology, and recombinant exchange of domains of animal and human factor VIII to produce hybrid human/animal factor VIII with coagulant activity; (d) creation of hybrid human/animal factor VIII by replacement of specific amino acid residues of the factor VIII of one species with the corresponding unique amino acid residues of the factor VIII of the other species; or (e) creation of a hybrid equivalent factor VIII molecule having human or animal amino acid sequence or both, in which specific amino acid residues of the factor VIII are replaced with amino acid residues having no known sequence identity to factor VIII by site-directed mutagenesis.

Some embodiments of hybrid or hybrid equivalent factor VIII have specific activity greater than that of human factor VIII and equal to or greater than that of porcine factor VIII. Some embodiments of hybrid or hybrid equivalent factor VIII have equal or less immunoreactivity with inhibitory antibodies to factor VIII and/or less immunogenicity in humans or animals, compared to human or porcine factor VIII.

Also provided are pharmaceutical compositions and methods for treating patients having factor VIII deficiency comprising administering the hybrid or hybrid equivalent factor VIII.

BRIEF DESCRIPTION OF THE DRAWINGS

FIGS. 1A and 1B is an amino acid sequence alignment of human, mouse, and porcine factor VIII A2 domains, in which residue numbering begins at position 373 with respect to the full length sequence of human factor VIII (SEQ ID NO: 2).

DETAILED DESCRIPTION OF THE INVENTION DEFINITIONS

Unless otherwise specified or indicated, as used herein, "hybrid factor VIII" or "hybrid protein" denotes any functional factor VIII protein molecule or fragment thereof comprising factor VIII amino acid sequence from human, porcine, and/or non-human, non-porcine mammalian species. Such combinations include, but are not limited to, any or all of the following hybrid factor VIII molecules or fragments thereof: (1) human/porcine; (2) human/non-human, non-porcine mammalian, such as human/mouse; (3) porcine/non-human, non-porcine mammalian, such as porcine/mouse; and (4) species-1/species-2, in which neither species is porcine or human, such as mouse/dog. Such combinations also include hybrid factor VIII equivalent molecules or fragments thereof, as further defined below, comprising factor VIII amino acid sequence of hybrid, human, porcine, or non-human, non-porcine mammalian origin in which amino acid sequence having no known sequence identity to factor VIII is substituted. Such hybrid combinations also include hybrid factor VIII molecules or fragments thereof comprising factor VIII amino acid sequence derived from more than two species, such as human/pig/mouse, or from two or more species in which amino acid sequence having no known sequence identity to factor VIII is substituted. Unless otherwise indicated, "hybrid factor VIII" includes fragments of the hybrid factor VIII, which can be used, as described below in one exemplary embodiment, as probes for research purposes or as diagnostic reagents.

As used herein, "mammalian factor VIII" includes factor VIII with amino acid sequence derived from any non-human mammal, unless otherwise specified. "Animal", as used herein, refers to pig and other non-human mammals.

A "fusion protein" or "fusion factor VIII or fragment thereof", as used herein, is the product of a hybrid gene in which the coding sequence for one protein is extensively altered, for example, by fusing part of it to the coding sequence for a second protein from a different gene to produce a hybrid gene that encodes the fusion protein. As used herein, a fusion protein is a subset of the hybrid VIII protein described in this application.

A "corresponding" nucleic acid or amino acid or sequence of either, as used herein, is one present at a site in a factor VIII or hybrid factor VIII molecule or fragment thereof that has the same structure and/or function as a site in the factor VIII molecule of another species, although the nucleic acid or amino acid number may not be identical. A sequence "corresponding to" another factor VIII sequence substantially corresponds to such sequence, and hybridizes to the sequence of the designated SEQ ID NO. under stringent conditions. A sequence "corresponding to" another factor VIII sequence also includes a sequence that results in the expression of a factor VIII or claimed procoagulant hybrid factor VIII or fragment thereof and would hybridize to the designated SEQ ID NO. but for the redundancy of the genetic code.

A "unique" amino acid residue or sequence, as used herein, refers to an amino acid sequence or residue in the factor VIII molecule of one species that is different from the homologous residue or sequence in the factor VIII molecule of another species.

"Specific activity," as used herein, refers to the activity that will correct the coagulation defect of human factor VIII deficient plasma. Specific activity is measured in units of clotting activity per milligram total factor VIII protein in a standard assay in which the clotting time of human factor VIII deficient plasma is compared to that of normal human plasma. One unit of factor VIII activity is the activity present in one milliliter of normal human plasma. In the assay, the shorter the time for clot formation, the greater the activity of the factor VIII being assayed. Hybrid human/porcine factor VIII has coagulation activity in a human factor VIII assay. This activity, as well as that of other hybrid or hybrid equivalent factor VIII molecules or fragments thereof, may be less than, equal to, or greater than that of either plasma-derived or recombinant human factor VIII.

The human factor VIII cDNA nucleotide and predicted amino acid sequences are shown in SEQ ID NOs:1 and 2, respectively. Factor VIII is synthesized as an approximately 300 kDa single chain protein with internal sequence homology that defines the "domain" sequence $NH_2$-A1-A2-B-A3-C1-C2-COOH. In a factor VIII molecule, a "domain", as used herein, is a continuous sequence of amino acids that is defined by internal amino acid sequence identity and sites of proteolytic cleavage by thrombin. Unless otherwise specified, factor VIII domains include the following amino acid residues, when the sequences are aligned with the human amino acid sequence (SEQ ID NO:2): A1, residues Ala1-Arg372; A2, residues Ser373-Arg740; B, residues Ser741-Arg1648; A3, residues Ser1690-Ile2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the factor VIII light chain activation peptide. Factor VIII is proteolytically activated by thrombin or factor Xa, which dissociates it from von Willebrand factor, forming factor VIIIa, which has procoagulant function. The biological function of factor VIIIa is to increase the catalytic efficiency of factor IXa toward factor X activation by several orders of magnitude. Thrombin-activated factor VIIIa is a 160 kDa A1/A2/A3-C1-C2 heterotrimer that forms a complex with factor IXa and factor X on the surface of platelets or monocytes. A "partial domain" as used herein is a continuous sequence of amino acids forming part of a domain.

"Subunits" of human or animal factor VIII, as used herein, are the heavy and light chains of the protein. The heavy chain of factor VIII contains three domains, A1, A2, and B. The light chain of factor VIII also contains three domains, A3, C1, and C2.

The hybrid factor VIII or fragment thereof can be made (1) by substitution of isolated, plasma-derived animal subunits or human subunits (heavy or light chains) for corresponding human subunits or animal subunits; (2) by substitution of human domains or animal domains (A1, A2, A3, B, C1, and C2) for corresponding animal domains or human domains; (3) by substitution of parts of human domains or animal domains for parts of animal domains or human domains; (4) by substitution of at least one specific sequence including one or more unique human or animal amino acid(s) for the corresponding animal or human amino acid (s); or (5) by substitution of amino acid sequence that has no known sequence identity to factor VIII for at least one sequence including one or more specific amino acid residue (s) in human, animal, or hybrid factor VIII or fragments thereof. A "B-domainless" hybrid factor VIII, hybrid equivalent factor VIII, or fragment of either, as used herein, refers to any one of the hybrid factor VIII constructs described herein that lacks the B domain.

The terms "epitope", "antigenic site", and "antigenic determinant", as used herein, are used synonymously and are defined as a portion of the human, animal, hybrid, or hybrid equivalent factor VIII or fragment thereof that is specifically recognized by an antibody. It can consist of any number of amino acid residues, and it can be dependent upon the primary, secondary, or tertiary structure of the protein. In accordance with this disclosure, a hybrid factor VIII, hybrid factor VIII equivalent, or fragment of either that includes at least one epitope may be used as a reagent in the diagnostic assays described below. In some embodiments, the hybrid or hybrid equivalent factor VIII or fragment thereof is not cross-reactive or is less cross-reactive with all naturally occurring inhibitory factor VIII antibodies than human or porcine factor VIII.

The term "immunogenic site", as used herein, is defined as a region of the human or animal factor VIII, hybrid or hybrid equivalent factor VIII, or fragment thereof that specifically elicits the production of antibody to the factor VIII, hybrid, hybrid equivalent, or fragment in a human or animal, as measured by routine protocols, such as immunoassay, e.g. ELISA, or the Bethesda assay, described herein. It can consist of any number of amino acid residues, and it can be dependent upon the primary, secondary, or tertiary structure of the protein. In some embodiments, the hybrid or hybrid equivalent factor VIII or fragment thereof is nonimmunogenic or less immunogenic in an animal or human than human or porcine factor VIII.

As used herein, a "hybrid factor VIII equivalent molecule or fragment thereof" or "hybrid equivalent factor VIII or fragment thereof" is an active factor VIII or hybrid factor VIII molecule or fragment thereof comprising at least one sequence including one or more amino acid residues that have no known identity to human or animal factor VIII sequence substituted for at least one sequence including one or more specific amino acid residues in the human, animal, or hybrid factor VIII or fragment thereof. The sequence of one or more amino acid residues that have no known identity to human or animal factor VIII sequence is also referred to herein as "non-factor VIII amino acid sequence". In a preferred embodiment, the amino acid(s) having no known sequence identity to factor VIII sequence are alanine residues. In another preferred embodiment, the specific factor VIII sequence for which the amino acid(s) having no known sequence identity to factor VIII sequence are substituted includes an antigenic site that is immunoreactive with naturally occurring factor VIII inhibitory antibodies, such that the resulting hybrid factor VIII equivalent molecule or fragment thereof is less immunoreactive or not immunoreactive with factor VIII inhibitory antibodies. In yet another preferred embodiment, the specific hybrid factor VIII sequence for which the amino acid(s) having no known sequence identity to factor VIII sequence are substituted includes an immunogenic site that elicits the formation of factor VIII inhibitory antibodies in an animal or human, such that the resulting hybrid factor VIII equivalent molecule or fragment thereof is less immunogenic.

"Factor VIII deficiency," as used herein, includes deficiency in clotting activity caused by production of defective factor VIII, by inadequate or no production of factor VIII, or by partial or total inhibition of factor VIII by inhibitors. Hemophilia A is a type of factor VIII deficiency resulting from a defect in an X-linked gene and the absence or deficiency of the factor VIII protein it encodes.

As used herein, "diagnostic assays" include assays that in some manner utilize the antigen-antibody interaction to detect and/or quantify the amount of a particular antibody that is present in a test sample to assist in the selection of medical therapies. There are many such assays known to those of skill in the art. As used herein, however, the hybrid or hybrid equivalent factor VIII DNA or fragment thereof and protein expressed therefrom, in whole or in part, can be substituted for the corresponding reagents in the otherwise known assays, whereby the modified assays may be used to detect and/or quantify antibodies to factor VIII. It is the use of these reagents, the hybrid or hybrid equivalent factor VIII DNA or fragment thereof or protein expressed therefrom, that permits modification of known assays for detection of antibodies to human or animal factor VIII or to hybrid human/animal factor VIII. Such assays include, but are not limited to ELISAs, immunodiffusion assays, and immunoblots. Suitable methods for practicing any of these assays are known to those of skill in the art. As used herein, the hybrid or hybrid equivalent factor VIII or fragment thereof that includes at least one epitope of the protein can be used as the diagnostic reagent. Examples of other assays in which the hybrid or hybrid equivalent factor VIII or fragment thereof can be used include the Bethesda assay and anticoagulation assays.

General Description of Methods

U.S. Ser. No. 07/864,004 describes the discovery of hybrid human/porcine factor VIII molecules having coagulant activity, in which elements of the factor VIII molecule of human or pig are substituted for corresponding elements of the factor VIII molecule of the other species. U.S. Ser. No. 08/212,133 and PCT/US94/13200 describe procoagulant hybrid human/animal and hybrid equivalent factor VIII molecules, in which elements of the factor VIII molecule of one species are substituted for corresponding elements of the factor VIII molecule of the other species.

The present invention provides hybrid human/animal, animal/animal, and equivalent factor VIII molecules and fragments thereof, and the nucleic acid sequences encoding such hybrids, some of which have greater coagulant activity in a standard clotting assay when compared to highly-purified human factor VIII; and/or are less immunoreactive to inhibitory antibodies to human or porcine factor VIII than human or porcine factor VIII; and/or are less immunogenic in a human or animal than human or porcine factor VIII. These hybrid factor VIII molecules can be constructed as follows.

At least five types of active hybrid human/porcine or hybrid equivalent factor VIII molecules or fragments thereof, the nucleic acid sequences encoding these hybrid factor VIII molecules, and the methods for preparing them are disclosed herein: those obtained (1) by substituting a human or porcine subunit (i.e., heavy chain or light chain) for the corresponding porcine or human subunit; (2) by substituting one or more human or porcine domain(s) (i.e., A1, A2, A3, B, C1, and C2) for the corresponding porcine or human domain(s); (3) by substituting a continuous part of one or more human or porcine domain(s) for the corresponding part of one or more porcine or human domain(s); (4) by substituting at least one specific sequence including one or more unique amino acid residue(s) in human or porcine factor VIII for the corresponding porcine or human sequence; and (5) by substituting at least one sequence including one or more amino acid residue(s) having no known sequence identity to factor VIII ("non-factor VIII amino acid sequence") for at least one specific sequence of one or more amino acids in human, porcine, or hybrid human/porcine factor VIII.

At least five types of active hybrid human/non-human, non-porcine mammalian or hybrid equivalent factor VIII molecules or fragments thereof, and the nucleic acid sequences encoding them, can also be prepared by the same methods: those obtained (1) by substituting a human or non-human, non-porcine mammalian subunit (i.e., heavy chain or light chain) for the corresponding non-human, non-porcine mammalian or human subunit; (2) by substituting one or more human or non-human, non-porcine mammalian domain(s) (i.e., A1, A2, A3, B, C1, and C2) for the corresponding non-human, non-porcine mammalian or human domain(s); (3) by substituting a continuous part of one or more human or non-human, non-porcine mammalian domain(s) for the corresponding part of one or more non-human, non-porcine mammalian or human domain(s); (4) by substituting at least one specific sequence including one or more unique amino acid residue(s) in human or non-human, non-porcine mammalian factor VIII for the corresponding non-human, non-porcine mammalian or human sequence; and (5) by substituting at least one sequence including one or more amino acid residue(s) having no known sequence identity to factor VIII ("non-factor VIII amino acid sequence") for at least one specific sequence of one or more amino acids in human, non-human, non-porcine mammalian, or hybrid human/non-human, non-porcine mammalian factor VIII.

Further, one skilled in the art will readily recognize that the same methods can be used to prepare at least five types of active hybrid factor VIII molecules or fragments thereof, corresponding to types (1)–(5) in the previous two paragraphs, comprising factor VIII amino acid sequence from two or more non-human mammals, such as porcine/mouse, and further comprising non-factor VIII amino acid sequence.

Hybrid human/animal, animal/animal, and equivalent factor VIII proteins or fragments thereof listed above under groups (1)–(3) are made by isolation of subunits, domains, or continuous parts of domains of plasma-derived factor VIII, followed by reconstitution and purification. Hybrid human/animal, animal/animal, and equivalent factor VIII proteins or fragments thereof described under groups (3)–(5) above are made by recombinant DNA methods. The hybrid molecule may contain a greater or lesser percentage of human than animal sequence, depending on the origin of the various regions, as described in more detail below.

Since current information indicates that the B domain has no inhibitory epitope and has no known effect on factor VIII function, in some embodiments the B domain is deleted in the active hybrid or hybrid equivalent factor VIII molecules or fragments thereof ("B(−) factor VIII") prepared by any of the methods described herein.

It is shown in Example 4 that hybrid human/porcine factor VIII comprising porcine heavy chain and human light chain and corresponding to the first type of hybrid listed above has greater specific coagulant activity in a standard clotting assay compared to human factor VIII. The hybrid human/animal or equivalent factor VIII with coagulant activity, whether the activity is higher, equal to, or lower than that of human factor VIII, can be useful in treating patients with inhibitors, since these inhibitors can react less with hybrid human/animal or equivalent factor VIII than with either human or porcine factor VIII.

Preparation Of Hybrid Factor VIII Molecules From Isolated Human And Animal Factor VIII Subunits By Reconstitution The present invention provides hybrid human/animal factor VIII molecules or fragments thereof, with subunit substitutions, the nucleic acid sequences encoding these hybrids, methods for preparing and isolating them, and methods for characterizing their procoagulant activity. One method, modified from procedures reported by Fay, P. J., et al., 265 J. Biol. Chem. 6197 (1990); and Lollar, J. S., et al., 263 J. Biol. Chem. 10451 (1988), involves the isolation of subunits (heavy and light chains) of human and animal factor VIII, followed by recombination of human heavy chain and animal light chain or by recombination of human light chain and animal heavy chain.

Isolation of both human and animal individual subunits involves dissociation of the light chain/heavy chain dimer. This is accomplished, for example, by chelation of calcium with ethylenediaminetetraacetic acid (EDTA), followed by monoS™ HPLC (Pharmacia-LKB, Piscataway, N.J.). Hybrid human/animal factor VIII molecules are reconstituted from isolated subunits in the presence of calcium. Hybrid human light chain/animal heavy chain or animal light chain/human heavy chain factor VIII is isolated from unreacted heavy chains by monoS™ HPLC by procedures for the isolation of porcine factor VIII, such as described by Lollar, J. S., et al., 71 Blood 137–143 (1988).

These methods, used in one embodiment to prepare active hybrid human/porcine factor VIII, described in detail in the examples below, result in hybrid human light chain/porcine heavy chain molecules with greater than six times the procoagulant activity of human factor VIII.

Other hybrid human/non-human, non-porcine mammalian factor VIII molecules can be prepared, isolated, and characterized for activity by the same methods. One skilled in the art will readily recognize that these methods can also be used to prepare, isolate, and characterize for activity hybrid animal/animal factor VIII, such as porcine/mouse, comprising the light or heavy chain or one species is combined with the heavy or light chain of the other species.

Preparation Of Hybrid Factor VIII Molecules From Isolated Human And Animal Factor VIII Domains By Reconstitution The present invention provides hybrid human/animal factor VIII molecules or fragments thereof with domain substitutions, the nucleic acid sequences encoding them, methods for preparing and isolating them, and methods for characterizing their procoagulant activity. One method involves the isolation of one or more domains of human and one or more domains of animal factor VIII, followed by recombination of human and animal domains to form hybrid human/animal factor VIII with coagulant activity, as described by Lollar, P., et al., 267(33) J. Biol. Chem. 23652–23657 (Nov. 25, 1992), for hybrid human/porcine factor VIII.

Specifically provided is a hybrid human/porcine factor VIII with substitution of the porcine A2 domain for the human A2 domain, which embodiment illustrates a method by which domain-substituted hybrid human/non-human, non-porcine mammalian factor VIII can be constructed. Plasma-derived non-human, non-porcine mammalian and human A1/A3-C1-C2 dimers are isolated by dissociation of the A2 domain from factor VIIIa. This is accomplished, for example, in the presence of NaOH, after which the mixture is diluted and the dimer is eluted using monoS™ HPLC (Pharmacia-LKB, Piscataway, N.J.). The A2 domain is isolated from factor VIIIa as a minor component in the monoS™ HPLC. Hybrid human/animal factor VIII molecules are reconstituted by mixing equal volumes of the A2 domain of one species and the A1/A3-C1-C2 dimer of the other species.

Hybrid human/animal factor VIII or fragments thereof with one or more domain substitutions is isolated from the mixture of unreacted dimers and A2 by monoS™ HPLC by procedures for the isolation of porcine factor VIII, as described by Lollar, J. S., et al., 71 Blood 137–143 (1988). Routine methods can also be used to prepare and isolate the A1, A3, C1, C2, and B domains of the factor VIII of one species, any one or more of which can be substituted for the corresponding domain in the factor VIII of the other species. One skilled in the art will readily recognize that these methods can also be used to prepare, isolate, and characterize for activity domain-substituted hybrid animal/animal factor VIII, such as porcine/mouse.

These methods, described in detail in the examples below, result in hybrid factor VIII molecules with procoagulant activity.

Preparation of Hybrid Factor VIII Molecules by Recombinant Engineering of the Sequences Encoding Human, Animal, and Hybrid Factor VIII Subunits, Domains, or parts of Domains Substitution of subunits, domains, continuous parts of domains:

The present invention provides active, recombinant hybrid human/animal and hybrid equivalent factor VIII molecules and fragments thereof with subunit, domain, and amino acid sequence substitutions, the nucleic acid sequences encoding these hybrids, methods for preparing and isolating them, and methods for characterizing their coagulant, immunoreactive, and immunogenic properties.

The human factor VIII gene was isolated and expressed in mammalian cells, as reported by Toole, J. J., et al., 312 Nature 342–347 (1984) (Genetics Institute); Gitschier, J., et al., 312 Nature 326–330 (1984) (Genentech); Wood, W. I., et al., 312 Nature 330–337 (1984) (Genentech); Vehar, G. A., et al., 312 Nature 337–342 (1984) (Genentech); WO 87/04187; WO 88/08035; WO 88/03558; U.S. Pat. No. 4,757,006, and the amino acid sequence was deduced from cDNA. U.S. Pat. No. 4,965,199 to Capon et al. discloses a recombinant DNA method for producing factor VIII in mammalian host cells and purification of human factor VIII. Human factor VIII expression in CHO (Chinese hamster ovary) cells and BHKC (baby hamster kidney cells) has been reported. Human factor VIII has been modified to delete part or all of the B domain (U.S. Pat. No. 4,868,112), and replacement of the human factor VIII B domain with the human factor V B domain has been attempted (U.S. Pat. No. 5,004,803). The CDNA sequence encoding human factor VIII and predicted amino acid sequence are shown in SEQ ID NOs:1 and 2, respectively.

Porcine factor VIII has been isolated and purified from plasma (Fass, D. N., et al., 59 *Blood* 594 (1982)). Partial amino acid sequence of porcine factor VIII corresponding to portions of the N-terminal light chain sequence having homology to ceruloplasmin and coagulation factor V and largely incorrectly located were described by Church et al., 81 *Proc. Natl. Acad. Sci. USA* 6934 (1984). Toole, J. J., et al., 312 *Nature* 342–347 (1984) described the partial sequencing of the N-terminal end of four amino acid fragments of porcine factor VIII but did not characterize the fragments as to their positions in the factor VIII molecule. The amino acid sequence of the B and part of the A2 domains of porcine factor VIII were reported by Toole, J. J., et al., 83 *Proc. Natl. Acad. Sci. U.S.A.* 5939–5942 (1986). The cDNA sequence encoding the complete A2 domain of porcine factor VIII and predicted amino acid sequence and hybrid human/porcine factor VIII having substitutions of all domains, all subunits, and specific amino acid sequences were disclosed in U.S. Ser. No. 07/864,004 entitled "Hybrid Human/Porcine Factor VIII" filed Apr. 7, 1992 by John S. Lollar and Marschall S. Runge, which issued as U.S. Pat. No. 5,364,771 on Nov. 15, 1994, and in WO 93/20093. The cDNA sequence encoding the A2 domain of porcine factor VIII having sequence identity to residues 373–740 in mature human factor VIII, as shown in SEQ ID NO:1, and the predicted amino acid sequence are shown in SEQ ID NOs:3 and 4, respectively. More recently, the nucleotide and corresponding amino acid sequences of the A1 and A2 domains of porcine factor VIII and a chimeric factor VIII with porcine A1 and/or A2 domains substituted for the corresponding human domains were reported in WO 94/11503.

Both porcine and human factor VIII are isolated from plasma as a two subunit protein. The subunits, known as the heavy chain and light chain, are held together by a non-covalent bond that requires calcium or other divalent metal ions. The heavy chain of factor VIII contains three domains, A1, A2, and B, which are linked covalently. The light chain of factor VIII also contains three domains, designated A3, C1, and C2. The B domain has no known biological function and can be removed from the molecule proteolytically or by recombinant DNA technology methods without significant alteration in any measurable parameter of factor VIII. Human recombinant factor VIII has a similar structure and function to plasma-derived factor VIII, though it is not glycosylated unless expressed in mammalian cells.

Both human and porcine activated factor VIII ("factor VIIIa") have three subunits due to cleavage of the heavy chain between the A1 and A2 domains. This structure is designated A1/A2/A3-C1-C2. Human factor VIIIa is not stable under the conditions that stabilize porcine factor VIIIa, presumably because of the weaker association of the A2 subunit of human factor VIIIa. Dissociation of the A2 subunit of human and porcine factor VIIIa is associated with loss of activity in the factor VIIIa molecule.

Using as probes the known sequence of parts of the porcine factor VIII molecule, the domains of the porcine factor VIII molecule that have not been sequenced to date can be sequenced by standard, established cloning techniques, such as those described in Weis, J. H., "Construction of recombinant DNA libraries," in *Current Protocols in Molecular Biology*, F. M. Ausubel et al., eds. (1991); and Sambrook, J., et al., *Molecular Cloning, A Laboratory Manual*, so that full length hybrids can be constructed.

Specifically provided as an exemplary and a preferred embodiment is active recombinant hybrid human/porcine factor VIII having substituted A2 domain, the nucleic acid sequence encoding it, and the methods for preparing, isolating, and characterizing its activity. The methods by which this hybrid construct is prepared can also be used to prepare active recombinant hybrid human/porcine factor VIII or fragments thereof having substitution of subunits, continuous parts of domains, or domains other than A2. One skilled in the art will recognize that these methods also demonstrate how other recombinant hybrid human/non-human, non-porcine mammalian or animal/animal hybrid factor VIII molecules or fragments thereof can be prepared in which subunits, domains, or continuous parts of domains are substituted.

Recombinant hybrid human/porcine factor VIII is prepared starting with human cDNA (Biogen, Inc.) encoding the factor VIII sequence. In a preferred embodiment, the factor VIII encoded by this cDNA includes domains A1-A2-A3-C1-C2, lacking the entire B domain, and corresponds to amino acid residues 1–740 and 1649–2332 of single chain human factor VIII (see SEQ ID NO:2), according to the numbering system of Wood et al., 312 *Nature* 330–337 (1984).

Individual subunits, domains, or continuous parts of domains of porcine or human factor VIII cDNA can be cloned and substituted for the corresponding human or porcine subunits, domains, or parts of domains by established mutagenesis techniques. For example, Lubin, I. M., et al., 269(12) *J. Biol Chem.* 8639–8641 (March 1994) describes techniques for substituting the porcine A2 domain for the human domain using convenient restriction sites. Other methods for substituting any arbitrary region of the factor VIII cDNA of one species for the factor VIII cDNA of another species include splicing by overlap extension ("SOE"), as described by Horton, R. M., et al., 217 *Meth. Enzymol.* 270–279 (1993).

The hybrid factor VIII cDNA encoding subunits, domains, or parts of domains or the entire hybrid cDNA molecules are cloned into expression vectors for ultimate expression of active hybrid human/porcine factor VIII protein molecules in cultured cells by established techniques, as described by Selden, R. F., "Introduction of DNA into mammalian cells," in *Current Protocols in Molecular Biology*, F. M. Ausubel et al., eds (1991).

In a preferred embodiment, a hybrid human/porcine cDNA encoding factor VIII, in which the porcine sequence encodes a domain or part domain, such the A2 domain or part domain, is inserted in a mammalian expression vector, such as ReNeo, to form a hybrid factor VIII construct. Preliminary characterization of the hybrid factor VIII is accomplished by insertion of the hybrid cDNA into the ReNeo mammalian expression vector and transient expression of the hybrid protein in COS-7 cells. A determination of whether active hybrid protein is expressed can then be made. The expression vector construct is used further to stably transfect cells in culture, such as baby hamster kidney cells, using methods that are routine in the art, such as liposome-mediated transfection (Lipofectin™, Life Technologies, Inc.). Expression of recombinant hybrid factor VIII protein can be confirmed, for example, by sequencing, Northern and Western blotting, or polymerase chain reaction (PCR). Hybrid factor VIII protein in the culture media in which the transfected cells stably expressing the protein are maintained can be precipitated, pelleted, washed, and resuspended in an appropriate buffer, and the recombinant hybrid factor VIII protein purified by standard techniques, including immunoaffinity chromatography using, for example, monoclonal anti-A2-Sepharose™.

In a further embodiment, the hybrid factor VIII comprising subunit, domain, or amino acid sequence substitutions is expressed as a fusion protein from a recombinant molecule in which sequence encoding a protein or peptide that enhances, for example, stability, secretion, detection, isolation, or the like is inserted in place adjacent to the factor VIII encoding sequence. Established protocols for use of homologous or heterologous species expression control sequences including, for example, promoters, operators, and regulators, in the preparation of fusion proteins are known and routinely used in the art. See *Current Protocols in Molecular Biology* (Ausubel, F. M., et al., eds), Wiley Interscience, N.Y.

The purified hybrid factor VIII or fragment thereof can be assayed for immunoreactivity and coagulation activity by standard assays including, for example, the plasma-free factor VIII assay, the one-stage clotting assay, and the enzyme-linked immunosorbent assay using purified recombinant human factor VIII as a standard.

Other vectors, including both plasmid and eukaryotic viral vectors, may be used to express a recombinant gene construct in eukaryotic cells depending on the preference and judgment of the skilled practitioner (see, for example, Sambrook et al., Chapter 16). Other vectors and expression systems, including bacterial, yeast, and insect cell systems, can be used but are not preferred due to differences in, or lack of, glycosylation.

Recombinant hybrid factor VIII protein can be expressed in a variety of cells commonly used for culture and recombinant mammalian protein expression. A preferred cell line, available from the American Type Culture Collection, Rockville, Md., is baby hamster kidney cells, which are cultured using routine procedure and media.

The same methods employed for preparing hybrid human/porcine factor VIII having subunit, domain, or amino acid sequence substitution can be used to prepare other recombinant hybrid factor VIII protein and fragments thereof and the nucleic acid sequences encoding these hybrids, such as human/non-human, non-porcine mammalian or animal/animal. Starting with primers from the known human DNA sequence, the murine and part of the porcine factor VIII cDNA have been cloned. Factor VIII sequences of other species for use in preparing a hybrid human/animal or animal/animal factor VIII molecule can be obtained using the known human and porcine DNA sequences as a starting point. Other techniques that can be employed include PCR amplification methods with animal tissue DNA, and use of a cDNA library from the animal to clone out the factor VIII sequence.

As an exemplary embodiment, hybrid human/mouse factor VIII protein can be made as follows. DNA clones corresponding to the mouse homolog of the human factor VIII gene have been isolated and sequenced and the amino acid sequence of mouse factor VIII protein predicted, as described in Elder, G., et al., 16(2) *Genomics* 374–379 (May 1993), which also includes a comparison of the predicted amino acid sequences of mouse, human, and part of porcine factor VIII molecules. The mouse factor VIII cDNA sequence and predicted amino acid sequence are shown in SEQ ID NO:5 and SEQ ID NO:8, respectively. In a preferred embodiment, the RNA amplification with transcript sequencing (RAWTS) methods described in Sarkar, G., and S. S. Sommer, 244 *Science* 331–334 (1989), can be used. Briefly, the steps are (1) cDNA synthesis with oligo(dT) or an mRNA-specific oligonucleotide primer; (2) polymerase chain reaction (PCR) in which one or both oligonucleotides contains a phage promoter attached to a sequence complementary to the region to be amplified; (3) transcription with a phage promoter; and (4) reverse transcriptase-mediated dideoxy sequencing of the transcript, which is primed with a nested (internal) oligonucleotide. In addition to revealing sequence information, this method can generate an in vitro translation product by incorporating a translation initiation signal into the appropriate PCR primer; and can be used to obtain novel mRNA sequence information from other species.

Substitution of amino acid(s):

The present invention provides active recombinant hybrid human/animal and animal/animal factor VIII molecules or fragments thereof comprising at least one sequence including one or more unique amino acids of one species substituted for the corresponding amino acid sequence of the other species or fragments thereof, nucleic acid sequences encoding these hybrids, methods for preparing and isolating them, and methods for characterizing their coagulant, immunogenic, and immunoreactive properties.

The A2 domain is necessary for the procoagulant activity of the factor VIII molecule. Studies show that porcine factor VIII has six-fold greater procoagulant activity than human factor VIII (Lollar, P., and E. T. Parker 266 *J. Biol. Chem.* 12481–12486 (1991)), and that the difference in coagulant activity between human and porcine factor VIII appears to be based on a difference in amino acid sequence between one or more residues in the human and porcine A2 domains (Lollar, P., et al., 267 *J. Biol. Chem.* 23652–23657 (1992)). Further, the A2 and C2 domains and possibly a third light chain region in the human factor VIII molecule are thought to harbor the epitopes to which most, if not all, inhibitory antibodies react, according to Hoyer, L. W., and D. Scandella, 31 *Semin. Hematol.* 1–5 (1994).

Recombinant hybrid human/animal, animal/animal, or equivalent factor VIII molecules or fragments thereof can be made by substitution of at least one specific sequence including one or more unique amino acids from the A2, C2, and/or other domains of the factor VIII of one species for the corresponding sequence of the other species, wherein the amino acid sequences differ, as illustrated in more detail below, between the molecules of the two species. In an exemplary preferred embodiment described herein, the present invention provides active recombinant hybrid human/porcine factor VIII comprising porcine amino acid sequence substituted for corresponding human amino acid sequence that includes an epitope, wherein the hybrid factor VIII has decreased or no immunoreactivity with inhibitory antibodies to factor VIII. In a further embodiment, active recombinant hybrid factor VIII molecules can also be made comprising amino acid sequence from more than one species substituted for the corresponding sequence in a third species. Recombinant hybrid equivalent molecules can also be made, comprising human, animal, or hybrid factor VIII including at least one sequence including one or more amino acids that have no known sequence identity to factor VIII, as further described below.

Any hybrid factor VIII construct having specific amino acid substitution as described can be assayed by standard procedures for coagulant activity and for reactivity with inhibitory antibodies to factor VIII for identification of hybrid factor VIII molecules with enhanced coagulant activity and/or decreased antibody immunoreactivity. Hybrid molecules may also be identified that have reduced coagulant activity compared to human or porcine factor VIII but also have decreased antibody reactivity. One skilled in the art will recognize that hybrid factor VIII molecules or fragments thereof having less, equal, or greater coagulant activity, compared to human or porcine factor VIII, is useful for treating patients who have a factor VIII deficiency. The methods described herein to prepare active recombinant hybrid human/porcine factor VIII with substitution of specific amino acids can be used to prepare active recombinant hybrid human/non-human, non-porcine mammalian factor VIII protein, hybrid animal-1/animal-2 factor VIII, and hybrid equivalent factor VIII or fragments thereof.

Hybrid factor VIII molecules with altered coagulant activity.

The present invention provides procoagulant recombinant hybrid human/animal, animal/animal, or equivalent factor VIII molecules or fragments thereof comprising at least one specific sequence including one or more unique amino acids having procoagulant activity in the factor VIII of one species substituted for the corresponding amino acid sequence of the factor VIII of the other species, using established site-directed mutagenesis techniques as described herein. The specific sequences to be used in the substitution are selected and the hybrid constructs are prepared and assayed for coagulant activity, as follows. Specifically provided as a preferred and exemplary embodiment is a hybrid human/porcine factor VIII comprising amino acid substitutions in the A2 domain. It is understood that one skilled in the art can use these methods to prepare other hybrid human/animal, animal/animal, and equivalent factor VIII molecules or fragments thereof having altered coagulant activity, preferably increased coagulant activity compared to human factor VIII.

The basis for the greater coagulant activity in porcine factor VIII appears to be the more rapid spontaneous dissociation of the A2 subunit of human factor VIIIa than porcine factor VIIIa, which leads to loss of activity, according to Lollar, P., and C. G. Parker, 265 *J. Biol. Chem.* 1688–1692 (1990); Lollar, P., et al. 267 *J. Biol. Chem.* 23652–23657 (1992); Fay, P. J., and T. M. Smudzin, 267 *J. Biol. Chem.* 13246–13250 (1992).

A comparison of the alignment of the amino acid sequences of the human and porcine factor VIII A2 domains (residue numbering starts at position 373 with respect to the full length amino acid sequence of human factor VIII, SEQ ID NO:2) is shown in FIGS. 1A–1B. For preparation of a hybrid human/porcine factor VIII molecule with altered coagulant activity, the initial target candidates for mutagenesis, which were revealed upon comparison of the human and porcine A2 amino acid sequences (SEQ ID NOs:2 and 6, respectively) within the human A2 domain, are shown in Table I.

TABLE I

HUMAN AMINO ACID SEQUENCE TARGET CANDIDATES FOR MUTAGENESIS (SEQ ID NO:2)

| Sequence | Residues | Mismatches | Charge Changes |
|---|---|---|---|
| 398–403 | 6 | 4 | 1 |
| 434–444 | 10 | 4 | 3 |
| 484–496 | 13 | 7 | 3 |
| 598–603 | 6 | 4 | 2 |
| 536–541 | 6 | 4 | 0 |
| 713–722 | 10 | 6 | 2 |
| 727–737 | 11 | 6 | 2 |

Table I and the bold letters of FIGS. 1A–1B illustrate seven sequences in the human and pig A2 domain amino acid sequences (SEQ ID NOs:2 and 6, respectively) that constitute only 17 percent of the A2 domain but include 70 percent of the sequence differences between human and porcine A2 domains.

A recombinant hybrid human/porcine construct is described in which amino acids Ser373-Glu604 in the A2 domain (Ser373-Arg740) of human factor VIII have been replaced with the homologous porcine sequence. This construct does not react with A2 inhibitors and has the same coagulant activity as human B(−) factor VIII. A plasma-derived hybrid molecule is described that comprises a complete porcine A2 domain substitution in the human factor VIII that has increased coagulant activity compared to human factor VIII. Comparison of these constructs indicates that a region between residues Asp605 and Arg740 is responsible for the difference in activity between human and porcine factor VIII. This region can be defined more specifically by systematically making recombinant hybrid human/porcine factor VIII molecules with porcine substitutions in the region between Asp605 and Arg740 by using established site-directed mutagenesis techniques, for example, the "splicing by overlap extension" (SOE) method that has been used extensively to make hybrid factor VIII molecules containing porcine substitutions in the $NH_2$-terminal region of A2. These molecules can be expressed in COS-7 cells and baby hamster kidney cells as described above. They can be purified to homogeneity using methods known in the art, such as heparin-Sepharose™ and immunoaffinity chromatography. Protein concentration can be estimated by absorption of ultraviolet light at $A_{280}$, and the specific activity of the constructs can be determined by dividing coagulant activity (measured in units per ml by single stage clotting assay) by $A_{280}$. Human factor VIII has a specific activity of approximately 3000–4000 U/$A_{280}$, whereas porcine factor VIII has a specific activity of approximately 20,000 U/$A_{280}$. In a preferred embodiment, the procoagulant recombinant hybrid human/porcine factor VIII has a specific activity of 20,000 U/$A_{280}$ and contains a minimal amount of porcine substitution in the A2 domain.

As described herein, site-directed mutagenesis techniques are used to identify hybrid protein with coagulant activity that can be enhanced, equal to, or reduced, compared to human factor VIII, but preferably is enhanced. In the hybrid human/porcine embodiment, specific human sequences are replaced with porcine sequences, preferably using the splicing by overlap extension method (SOE), as described by Ho, S. N., et al., 77 *Gene* 51–59 (1994), and in Examples 7 and 8. Oligonucleotide-directed mutagenesis can also be used, as was done to loop out the amino acid sequence for part of the human A2 domain (see Example 7). As functional analysis of the hybrids reveals coagulant activity, the sequence can be further dissected and mapped for procoagulant sequence by standard point mutation analysis techniques.

The present invention contemplates that hybrid factor VIII cDNA and protein can be characterized by methods that are established and routine, such as DNA sequencing, coagulant activity assays, mass by ELISA and by UV absorbance at 280 nm of purified hybrid factor VIII, specific coagulant activity (U/mg), SDS-PAGE of purified hybrid factor VIII, and the like. Other known methods of testing for clinical effectiveness may be required, such as amino acid, carbohydrate, sulfate, or metal ion analysis.

A recombinant hybrid factor VIII having superior coagulant activity, compared to human factor VIII, may be less expensive to make than plasma-derived factor VIII and may decrease the amount of factor VIII required for effective treatment of factor VIII deficiency.

Hybrid factor VIII molecules with reduced immunoreactivity.

Epitopes that are immunoreactive with antibodies that inhibit the coagulant activity of factor VIII ("inhibitors" or "inhibitory antibodies") have been characterized based on known structure-function relationships in factor VIII. Presumably, inhibitors could act by disrupting any of the macromolecular interactions associated with the domain structure of factor VIII or its associations with von Willebrand factor, thrombin, factor Xa, factor IXa, or factor X. However, over 90 percent of inhibitory antibodies to human factor VIII act by binding to epitopes located in the 40 kDa A2 domain or 20 kDa C2 domain of factor VIII, disrupting specific functions associated with these domains, as described by Fulcher et al., 82 Proc. Natl. Acad. Sci. USA 7728–7732 (1985), and Scandella et al., 85 Proc. Natl. Acad. Sci. USA 6152–6156 (1988). In addition to the A2 and C2 epitopes, there may be a third epitope in the A3 or C1 domain of the light chain of factor VIII, according to Scandella et al., 82 Blood 1767–1775 (1993). The significance of this putative third epitope is unknown, but it appears to account for a minor fraction of the epitope reactivity in factor VIII.

Anti-A2 antibodies block factor X activation, as shown by Lollar et al., 93 J. Clin. Invest. 2497–2504 (1994). Previous mapping studies by deletion mutagenesis described by Ware et al., 3 Blood Coagul. Fibrinolysis 703–716 (1992), located the A2 epitope to within a 20 kDa region at the $NH_2$-terminal end of the 40 kDa A2 domain. Competition immunoradiometric assays have indicated that A2 inhibitors recognize either a common epitope or narrowly clustered epitopes, as described by Scandella et al., 67 Thromb. Haemostas. 665–671 (1992), and as demonstrated in Example 8.

The present invention provides active recombinant hybrid and hybrid equivalent factor VIII molecules or fragments thereof, the nucleic acid sequences encoding these hybrids, methods of preparing and isolating them, and methods for characterizing them. These hybrids comprise human/animal, animal/animal, or equivalent hybrid factor VIII molecules, further comprising at least one specific amino acid sequence including one or more unique amino acids of the factor VIII of one species substituted for the corresponding amino acid sequence of the factor VIII of the other species; or comprises at least one sequence including one or more amino acids having no known sequence identity to factor VIII substituted for specific amino acid sequence in human, animal, or hybrid factor VIII. The resulting hybrid factor VIII has reduced or no immunoreactivity to factor VIII inhibitory antibodies, compared to human or porcine factor VIII.

Using the approach described in the previous section for substitution of amino acids in the factor VIII molecule, mutational analysis is employed to select corresponding factor VIII amino acid sequence of one species, preferably porcine, which is substituted for at least one sequence including one or more amino acids in the factor VIII of another species, preferably human, or for amino acid sequence of a hybrid equivalent factor VIII molecule, that includes one or more critical region(s) in the A2, C2, or any other domain to which inhibitory antibodies are directed. The methods are described in more detail below. The resulting procoagulant recombinant hybrid construct has reduced or no immunoreactivity to inhibitory antibodies, compared in human factor VIII, using standard assays. Through systematic substitution of increasingly smaller amino acid sequences followed by assay of the hybrid construct for immunoreactivity, as described below, the epitope in any domain of a factor VIII molecule is mapped, substituted by amino acid sequence having less or no immunoreactivity, and a hybrid factor VIII is prepared.

It is understood that one skilled in the art can use this approach combining epitope mapping, construction of hybrid factor VIII molecules, and mutational analysis of the constructs to identify and replace at least one sequence including one or more amino acids comprising an epitope in the A2, C2, and/or other domains to which inhibitory antibodies are directed and to construct procoagulant recombinant hybrid human/animal, animal/animal, or equivalent factor VIII or fragments thereof having decreased or no immunoreactivity compared to human or porcine factor VIII. This approach is used, as described in Example 8, to prepare a recombinant procoagulant hybrid human/porcine factor VIII having porcine amino acid substitutions in the human A2 domain and no antigenicity to anti-factor VIII antibodies as an exemplary embodiment.

Usually, porcine factor VIII has limited or no reaction with inhibitory antibodies to human factor VIII. The recombinant hybrid human/porcine factor VIII molecules having decreased or no reactivity with inhibitory antibodies based on amino acid substitution in the A2 domain are prepared, as an example of how hybrid factor VIII can be prepared using the factor VIII of other species and substitutions in domains other than the A2, as follows. The porcine A2 domain is cloned by standard cloning techniques, such as those described above and in Examples 6, 7, and 8, and then cut and spliced within the A2 domain using routine procedures, such as using restriction sites to cut the cDNA or splicing by overlap extension (SOE). The resulting porcine amino acid sequence is substituted into the human A2 domain to form a hybrid factor VIII construct, which is inserted into a mammalian expression vector, preferably ReNeo, stably transfected into cultured cells, preferably baby hamster kidney cells, and expressed, as described above. The hybrid factor VIII is assayed for immunoreactivity, for example with anti-A2 antibodies by the routine Bethesda assay or by plasma-free chromogenic substrate assay. The Bethesda unit (BU) is the standard method for measuring inhibitor titers. If the Bethesda titer is not measurable (<0.7 BU/mg IgG) in the hybrid, then a human A2 epitope was eliminated in the region of substituted corresponding porcine sequence. The epitope is progressively narrowed, and the specific A2 epitope can thus be determined to produce a hybrid human/porcine molecule with as little porcine sequence as possible. As described herein, a 25-residue sequence corresponding to amino acids Arg484-Ile508 that is critical for inhibitory immunoreactivity has been identified and substituted in the human A2 domain. Within this sequence are only nine differences between human and porcine factor VIII. This region can be further analyzed and substituted.

Hybrid human/porcine factor VIII molecules having decreased or no reactivity with inhibitory antibodies based on substitution of amino acid sequence in the C1, C2, or other domain, with or without substitution in the A2 domain, can also be prepared. The C2 epitope, for example, can be mapped using the homolog scanning approach combined with site-directed mutagenesis. More specifically, the procedures can be the same or similar to those described herein for amino acid substitution in the A2 domain, including cloning the porcine C2 or other domain, for example by using RT-PCR or by probing a porcine liver cDNA library with human C2 or other domain DNA; restriction site techniques and/or successive SOE to map and simultaneously replace epitopes in the C2 or other domain; substitution for the human C2 or other domain in B(−) factor VIII; insertion into an expression vector, such as pBluescript; expression in cultured cells; and routine assay for immunoreactivity. For the assays, the reactivity of C2 hybrid factor VIII with a C2-specific inhibitor, MR (Scandella, D., et al., Thromb. Haemostasis 67:665–671 (1992) and Lubin et al. (1994)), and/or other C2 specific antibodies prepared by affinity chromatography can be performed.

The C2 domain consists of amino acid residues 2173–2332 (SEQ ID NO:2). Within this 154 amino acid region, inhibitor activity appears to be directed to a 65 amino acid region between residues 2248 and 2312, according to Shima, M., et al., 69 Thromb. Haemostas. 240–246 (1993). If the C2 sequence of human and porcine factor VIII is approximately 85 percent identical in this region, as it is elsewhere in the functionally active regions of factor VIII, there will be approximately ten differences between human and porcine factor VIII C2 amino acid sequence, which can be used as initial targets to construct hybrids with substituted C2 sequence.

It is likely that clinically significant factor VIII epitopes are confined to the A2 and C2 domains. However, if antibodies to other regions (A1, A3, B, or C1 domains) of factor VIII are identified, the epitopes can be mapped and eliminated by using the approach described herein for the nonantigenic hybrid human/porcine factor VIII molecules.

More specifically, mapping of the putative second light chain epitope and/or any other epitope in any other animal or human factor VIII domain can also be accomplished. Initially, determination of the presence of a third inhibitor epitope in the A3 or C1 domains can be made as follows. Using human ("H") and porcine ("p") factor VIII amino acid sequences as a model, $A1_P$-$A2_P$-$A3_P$-$C1_H$-$C2_P$ and $A1_P$-$A2_P$-$A3_H$-$C1_P$-$C2_P$ B-domainless hybrids will be constructed. Inhibitor IgG from approximately 20 patient plasmas (from Dr. Dorothea Scandella, American Red Cross) who have low or undetectable titers against porcine factor VIII will be tested against the hybrids. If the third epitope is in the A3 domain, inhibitory IgG is expected to react with $A1_P$-$A2_P$-$A3_H$-$C1_P$-$C2_P$ but not $A1_P$-$A2_P$-$A3_P$-$C1_H$-$C2_P$. Conversely, if the third epitope is in the C1 domain, then inhibitory IgG is expected to react with $A1_P$-$A2_P$-$A3_P$-$C1_H$-$C2_P$ but not $A1_P$-$A2_P$-$A3_H$-$C1_P$-$C2_P$. If a third epitope is identified it will be characterized by the procedures described herein for the A2 and C2 epitopes.

For example, antibodies specific for the C1 or A3 domain epitope can be isolated from total patient IgG by affinity chromatography using the $A1_P$-$A2_P$-$A3_H$-$C1_P$-$C2_P$ and $A1_P$-$A2_P$-$A3_P$-$C1_H$-$C1_P$ hybrids, and by elimination of C2 specific antibodies by passage over recombinant factor VIII C2-Sepharose™. The putative third epitope will be identified by SOE constructs in which, in a preferred embodiment, portions of the human factor VIII A3 or C1 domain are systematically replaced with porcine sequence.

Hybrid factor VIII molecules with reduced immunogenicity.

A molecule is immunogenic when it can induce the production of antibodies in human or animal. The present invention provides a procoagulant recombinant hybrid human/animal or animal/animal factor VIII molecule, hybrid factor VIII equivalent molecule, or fragment of either that is less immunogenic than wild-type human porcine factor VIII in human or animal, comprising at least one specific amino acid sequence including one or more unique amino acids of the factor VIII of one species substituted for the corresponding amino acid sequence that has immunogenic activity of the factor VIII of the other species; or at least one amino acid sequence including one or more amino acids having no known identity to factor VIII substituted for amino acid sequence of the human, animal, or hybrid factor. This hybrid can be used to lower the incidence of inhibitor development in an animal or human and to treat factor VIII deficiency, and would be preferred in treating previously untreated patients with hemophilia. In a preferred embodiment, the hybrid factor VIII comprises human factor VIII amino acid sequence, further comprising one or more alanine residues substituted for human amino acid sequence having immunogenic activity, resulting in a procoagulant recombinant hybrid equivalent molecule or fragment thereof having reduced or no immunogenicity in human or animal.

The process described herein of epitope mapping and mutational analysis combined with substitution of non-antigenic amino acid sequence in a factor VIII molecule, using hybrid human/porcine factor VIII, produces hybrid molecules with low antigenicity. Using this model and the associated methods, any of the hybrid constructs described herein can be altered by site-directed mutagenesis techniques to remove as much of any functional epitope as possible to minimize the ability of the immune system to recognize the hybrid factor VIII, thereby decreasing its immunogenicity.

One method that can be used to further reduce the antigenicity and to construct a less immunogenic hybrid factor VIII is alanine scanning mutagenesis, described by Cunningham, B. C., and J. A. Wells, 244 Science 1081–1085 (1989), of selected specific amino acid sequences in human, animal, or hybrid equivalent factor VIII. In alanine scanning mutagenesis, amino acid side chains that are putatively involved in an epitope are replaced by alanine residues by using site-directed mutagenesis. By comparing antibody binding of alanine mutants to wild-type protein, the relative contribution of individual side chains to the binding interaction can be determined. Alanine substitutions are likely to be especially useful, since side chain contributions to antibody binding are eliminated beyond the β carbon, but, unlike glycine substitution, main chain conformation is not usually altered. Alanine substitution does not impose major steric, hydrophobic or electrostatic effects that dominate protein-protein interactions.

In protein antigen-antibody interactions, there usually are about 15–20 antigen side chains in contact with the antibody. Side chain interactions, as opposed to main chain interactions, dominate protein-protein interactions. Recent studies have suggested that only a few (approximately 3 to 5) of these side-chain interactions contribute most of the binding energy. See Clackson, T., and J. A. Wells, 267 Science 383–386 (1995). An extensive analysis of growth hormone epitopes for several murine monoclonal antibodies revealed the following hierarchy for side chain contributions to the binding energy: Arg>Pro>Glu~Asp~Phe~Ile, with Trp, Ala, Gly, and Cys not tested (Jin, L., et al., 226 J. Mol. Biol. 851–865 (1992)). Results with the A2 epitope described herein are consistent with this, since twelve of the 25 residues in the 484–508 A2 segment contain these side chains (Table 1).

The finding that certain amino acid residues are particularly well recognized by antibodies, indicates that elimination of these residues from a known epitope can decrease the ability of the immune system to recognize these epitopes, i.e., can make a molecule less immunogenic. In the case of the A2 epitope, immunogenic residues can be replaced without loss of factor VIII coagulant activity. For example, in HP9, Arg484 is replaced by Ser, Pro485 is replaced by Ala, Arg489 is replaced by Gly, Pro492 is replaced by Leu, and Phe501 is replaced by Met. Further, results from the patient plasmas used to test immunoreactivity in hybrid human/porcine factor VIII constructs, described in Example 8, indicate that antibodies from different patients recognize the same or a very similar structural region in the A2 domain and that the residues in the A2 domain that participate in binding A2 inhibitors appear to show little variation. Thus, the A2 epitope included in human factor VIII residues 484–508 is an immunodominant epitope in that it is recognized by the human immune system better than other structural regions of factor VIII. Replacing this structure by nonantigenic factor VIII sequence from another species or by non-factor VIII amino acid sequence, while retaining full procoagulant activity, is expected to alter recognition of hybrid or hybrid equivalent factor VIII by the immune system.

It is anticipated that site-directed mutagenesis to replace bulky and/or charged residues that tend to dominate epitopes with small, neutral side chains (e.g., alanine) may produce a less immunogenic region. It is expected that a molecule containing a few of these substitutions at each significant inhibitor epitope will be difficult for the immune system to fit by the lock-and-key mechanism that is typical of antigen-antibody interactions. Because of its low antigenicity, such a hybrid molecule could be useful in treating factor VIII deficiency patients with inhibitors, and because of its low immunogenicity, it could useful in treating previously untreated patients with hemophilia A.

A general result is that mutation of one of a few key residues is sufficient to decrease the binding constant for a given protein-protein interaction by several orders of magnitude. Thus, it appears likely that all factor VIII epitopes contain a limited number of amino acids that are critical for inhibitor development. For each epitope in factor VIII, alanine substitutions for at least one sequence including one or more specific amino acids having immunogenic activity, may produce an active molecule that is less immunogenic than wild-type factor VIII. In a preferred embodiment, the hybrid factor VIII is B-domainless.

The methods for preparing active recombinant hybrid or hybrid equivalent factor VIII with substitution of amino acid sequence having little or no immunogenic activity for amino acid sequence in the factor VIII having immunogenic activity are as follows, using hybrid human/porcine factor VIII with amino acid substitutions in the A2 domain as an exemplary embodiment. There are 25 residues in the human factor VIII region 484–508. Site-directed mutagenesis can be used to make single mutants in which any of these residues is replaced by any of the other 19 amino acids for a total of 475 mutants. Furthermore, hybrid molecules having more than one mutation can be constructed.

The hybrid constructs can be assayed for antigenicity by measuring the binding constant for inhibitor antibodies, as described by Friguet, B., et al., 77 *J. Immunol. Methods* 77:305–319 (1985). In a preferred embodiment, the binding constant will be reduced by at least three orders of magnitude, which would lower the Bethesda titer to a level that is clinically insignificant. For example, the $IC_{50}$ (a crude measure of the binding constant) of inhibition by A2 antibodies was reduced in hybrid human/porcine factor VIII constructs HP2, HP4, HP5, HP7, and HP9, described in Example 8, and this was associated with a reduction in Bethesda titer to an unmeasurable level. It is anticipated, for example, that a double or triple alanine mutant of human factor VIII (e.g., a human factor VIII Arg484→Ala, Arg489→Ala, Phe501→Ala triple mutant) will produce a molecule with sufficiently low antigenicity for therapeutic use. Similar mutations can be made in the C2 epitope and the putative third epitope. In a preferred embodiment comprises two or three alanine substitutions into two or three factor VIII epitopes. Other substitutions into these regions can be also be done.

In a preferred embodiment, hybrid equivalent factor VIII molecules will be identified that are less antigenic and/or immunogenic in human and animal than either human or porcine factor VIII. Such hybrid equivalent constructs can be tested in animals for their reduced antigenicity and/or immunogenicity. For example, control and factor VIII deficient rabbits, pigs, dogs, mice, primates, and other mammals can be used as animal models. In one experimental protocol, the hybrid or hybrid equivalent factor VIII can be administered systematically over a period of six months to one year to the animal, preferably by intravenous infusion, and in a dosage range between 5 and 50 Units/kg body weight, preferably 10–50 Units/kg, and most preferably 40 Units/kg body weight. Antibodies can be measured in plasma samples taken at intervals after the infusions over the duration of the testing period by routine methods, including immunoassay and the Bethesda assay. Coagulant activity can also be measured in samples with routine procedures, including a one-stage coagulation assay.

The hybrid equivalent factor VIII molecules can be tested in humans for their reduced antigenicity and/or immunogenicity in at least two types of clinical trials. In one type of trial, designed to determine whether the hybrid or hybrid equivalent factor VIII is immunoreactive with inhibitory antibodies, hybrid or hybrid equivalent factor VIII is administered, preferably by intravenous infusion, to approximately 25 patients having factor VIII deficiency who have antibodies to factor VIII that inhibit the coagulant activity of therapeutic human or porcine factor VIII. The dosage of the hybrid or hybrid equivalent factor VIII is in a range between 5 and 50 Units/kg body weight, preferably 10–50 Units/kg, and most preferably 40 Units/kg body weight. Approximately 1 hour after each administration, the recovery of factor VIII from blood samples is measured in a one-stage coagulation assay. Samples are taken again approximately 5 hours after infusion, and recovery is measured. Total recovery and the rate of disappearance of factor VIII from the samples is predictive of the antibody titre and inhibitory activity. If the antibody titre is high, factor VIII recovery usually cannot be measured. The recovery results are compared to the recovery results in patients treated with plasma-derived human factor VIII, recombinant human factor VIII, porcine factor VIII, and other commonly used therapeutic forms of factor VIII or factor VIII substitutes.

In a second type of clinical trial, designed to determine whether the hybrid or hybrid equivalent factor VIII is immunogenic, i.e., whether patients will develop inhibitory antibodies, hybrid or hybrid equivalent factor VIII is administered, as described in the preceeding paragraph, to approximately 100 previously untreated hemophiliac patients who have not developed antibodies to factor VIII. Treatments are given approximately every 2 weeks over a period of 6 months to 1 year. At 1 to 3 month intervals during this period, blood samples are drawn and Bethesda assays or other antibody assays are performed to determine the presence of inhibitory antibodies. Recovery assays can also be done, as described above, after each infusion. Results are compared to hemophiliac patients who receive plasma-derived human factor VIII, recombinant human factor VIII, porcine factor VIII, or other commonly used therapeutic forms of factor VIII or factor VIII substitutes.

Preparation of hybrid factor VIII molecules using human and non-porcine, non-human mammalian factor VIII amino acid sequence.

The methods used to prepare hybrid human/porcine factor VIII with substitution of specific amino acids can be used to prepare recombinant hybrid human/non-human, non-porcine mammalian or animal/animal factor VIII protein that has, compared to human or porcine factor VIII, altered or the same coagulant activity and/or equal or reduced immunoreactivity and/or immunogenicity, based on substitution of one or more amino acids in the A2, C2, and/or other domains.

Similar comparisons of amino acid sequence identity can be made between human and non-human, non-porcine mammalian factor VIII proteins to determine the amino acid sequences in which procoagulant activity, anti-A2 and anti-C2 immunoreactivity, and or immunogenicity, or immunoreactivity and/or immunogenicity in other domains reside. Similar methods can then be used to prepare hybrid human/non-human, non-porcine mammalian factor VIII molecules. As described above, functional analysis of each hybrid will reveal those with decreased reactivity to inhibitory antibodies, and/or reduced immunogenicity, and/or increased coagulant activity, and the sequence can be further dissected by point mutation analysis.

For example, hybrid human/mouse factor VIII molecules can be prepared as described above. The amino acid sequence alignment of the A2 domain of human (SEQ ID NO:2) and mouse (SEQ ID NO:6) is shown in FIGS. 1A–1B. As reported by Elder et al., the factor VIII protein encoded by the mouse cDNA (SEQ ID NO:5) has 2319 amino acids, with 74% sequence identity overall to the human sequence (SEQ ID NO:2) (87 percent identity when the B domain is excluded from the comparison), and is 32 amino acids shorter than human factor VIII. The amino acid sequences in the mouse A and C domains (SEQ ID NO:6) are highly conserved, with 84–93 percent sequence identity to the human sequence (SEQ ID NO:2), while the B and the two short acidic domains have 42–70 percent sequence identity. Specifically, the A1, A2, and A3 mouse amino acid sequences (SEQ ID NO:6) are 85, 85, and 90 percent identical to the corresponding human amino acid sequences (SEQ ID NO:2). The C1 and C2 mouse amino acid sequences are 93 and 84 percent identical to the corresponding human amino acid sequences. In the predicted mouse factor VIII amino acid sequence (SEQ ID NO:6), the A1, A2, and A3 domains are homologous to human factor VIII amino acids 1–372, 373–740, and 1690–2032, respectively, using amino acid sequence identity for numbering purposes.

The thrombin/factor Xa and all but one activated protein C cleavage sites are conserved in mouse factor VIII. The tyrosine residue for von Willebrand factor binding is also conserved.

According to Elder et al., the nucleotide sequence (SEQ ID NO:5) of mouse factor VIII contains 7519 bases and has 67 percent identity overall with the human nucleotide sequence (SEQ ID NO:1). The 6957 base pairs of murine coding sequence have 82 percent sequence identity with the 7053 base pairs of coding sequence in human factor VIII. When the B domain is not included in the comparison, there is an 88 percent nucleotide sequence identity.

Elder et al. report that human and mouse factor VIII molecules are 74 percent identical overall, and that 95 percent of the human residues that lead to hemophilia when altered are identical in the mouse. These data support the application of the same techniques used to identify amino acid sequence with coagulant activity and/or immunoreactivity to antibodies in the porcine factor VIII molecule to the mouse or other animal factor VIII to identify similar amino acid sequences and prepare hybrid molecules.

Preparation of hybrid factor VIII molecules having reduced cross-reactivity using human and non-human, non-porcine mammalian factor VIII amino acid sequence and non-factor VIII amino acid sequence.

Porcine factor VIII is used clinically to treat factor VIII deficiency patients who have inhibitory antibodies to human factor VIII. Cross-reactivity, in which human plasma reacts with porcine factor VIII, can be reduced by preparation of hybrid porcine/non-human, non-porcine mammalian or hybrid equivalent factor VIII. In a preferred embodiment, a determination of whether human A2, C2, or other domain-specific inhibitors react with non-human, non-porcine mammalian ("other mammalian") factor VIII is made, using the routine Bethesda assay and the particular other mammalian plasma as the standard. Inhibitor titers are usually measured in plasma, so purified other mammalian factor VIII is not necessary. If the inhibitors do not react with the other mammalian factor VIII, such as murine factor VIII, the sequence of which is known, then corresponding other mammalian sequence can be substituted into the porcine epitope region, as identified by using human/porcine hybrids. Once the animal sequence is known, site directed mutagenesis techniques, such as oligonucleotide-mediated mutagenesis described by Kunkel, T. A., et al., 204 *Meth. Enzymol.* 125–139 (1991), can be used to prepare the hybrid porcine/animal factor VIII molecule. If other animal plasmas are less reactive with A2, C2, or other factor VIII inhibitors than murine or porcine factor VIII, the animal sequence corresponding to the porcine epitope can be determined by routine procedures, such as RT-PCR, and a hybrid human/animal or porcine/animal factor VIII constructed by site directed mutagenesis. Also, hybrid human/animal or porcine/non-porcine mammalian factor VIII having reduced cross-reactivity with human plasma compared to porcine factor VIII can be prepared that has corresponding amino acid sequence substitution from one or more other animals. In a further embodiment, cross-reactivity can be reduced by substitution of amino acid sequence having no known identity to factor VIII amino acid sequence, preferably alanine residues using alanine scanning mutagenesis techniques, for porcine epitope sequence.

After identification of clinically significant epitopes, recombinant hybrid factor VIII molecules will be expressed that have less than or equal cross-reactivity compared with porcine factor VIII when tested in vitro against a broad survey of inhibitor plasmas. Preferably these molecules will be combined A2/C2 hybrids in which immunoreactive amino acid sequence in these domains is replaced by other mammalian sequence. Additional mutagenesis in these regions may be done to reduce cross-reactivity. Reduced cross-reactivity, although desirable, is not necessary to produce a product that may have advantages over the existing porcine factor VIII concentrate, which produces side effects due to contaminant porcine proteins and may produce untoward effects due to the immunogenicity of porcine factor VIII sequences. A hybrid human/other mammalian or porcine/other mammalian factor VIII molecule will not contain foreign porcine proteins. Additionally, the extensive epitope mapping accomplished in the porcine A2 domain indicates that greater than 95% of the therapeutic hybrid human/porcine factor VIII sequence will be human.

Preparation of hybrid factor VIII equivalents:

The methods for amino acid substitution in factor VIII molecules described above and in the examples can also be used to prepare procoagulant recombinant hybrid factor VIII equivalent molecules or fragments thereof comprising at least one amino acid sequence including one or more amino acids having no known amino acid sequence identity to factor VIII ("non-factor VIII sequence") substituted for at least one specific amino acid sequence that includes an antigenic and/or immunogenic site in human, animal, or hybrid factor VIII. The resulting active hybrid factor VIII equivalent molecule has equal or less reactivity with factor VIII inhibitory antibodies and/or less immunogenicity in human and animals than the unsubstituted human, animal, or hybrid factor VIII.

Suitable amino acid residues that can be substituted for those sequences of amino acids critical to coagulant and/or antigenic and/or immunogenic activity in human or animal factor VIII or hybrid human/animal factor VIII to prepare a hybrid equivalent factor VIII molecule include any amino acids having no known sequence identity to animal or human factor VIII amino acid sequence that has coagulant, antigenic, or immunogenic activity. In a preferred embodiment, the amino acids that can be substituted include alanine residues using alanine scanning mutagenesis techniques.

Hybrid factor VIII equivalent molecules described herein also include those molecules in which amino acid residues having no known identity to animal factor VIII sequence are substituted for amino acid residues not critical to coagulant, antigenic, or immunogenic activity.

As described above, in one embodiment of a hybrid factor VIII equivalent molecule, the molecule has reduced cross-reactivity with inhibitor plasmas. One or more epitopes in the cross-reactive factor VIII are identified, as described above, and then replaced by non-factor VIII amino acid sequence, preferably alanine residues, using, for example, the alanine scanning mutagenesis method.

In a preferred embodiment, a procoagulant recombinant hybrid factor VIII equivalent molecule is prepared comprising at least one sequence including one or more amino acids having no known sequence identity to factor VIII, preferably alanine residues, substituted for at least one sequence including one or more amino acids including an epitope, and/or for at least one sequence including one or more amino acids including an immunogenic site, preferably in human factor VIII. The resulting hybrid equivalent factor VIII molecule or fragment thereof has reduced or no immunoreactivity with inhibitory antibodies to factor VIII and/or reduced or no immunogenicity in human or animals. The methods for identifying specific antigenic amino acid sequence in the A2 domain of human factor VIII for substitution by nonantigenic porcine unique amino acid sequence are described in Examples 7 and 8 and are exemplary for identifying antigenic sequence in the A2 and other domains of human and animal factor VIII and for using site-directed mutagenesis methods such as alanine scanning mutagenesis to substitute non-factor VIII amino acid sequence.

Since the human A2 epitope has been narrowed to 25 or fewer amino acids, as described in Example 8, alanine scanning mutagenesis can be performed on a limited number of hybrid factor VIII constructs having human amino acid sequence to determine which are procoagulant, non-immunoreactive and/or nonimmunogenic hybrid factor VIII constructs based on A2 amino acid substitutions. In the A2 domain, the most likely candidates for alanine substitutions to achieve both reduced antigenicity and immunogenicity in the hybrid construct are Arg484, Pro485, Tyr487, Ser488, Arg489, Pro492, Val495, Phe501, and Ile508. The binding affinity of a hybrid construct comprising each of these mutants for mAb413 and a panel of A2 specific patient IgGs will be determined by ELISA. Any mutant that is active and has a binding affinity for A2 inhibitors that is reduced by more than 2 orders of magnitude is a candidate for the A2 substituted factor VIII molecule. Constructs having more than one mutation will be selected, based on the assumption that the more the epitope is altered, the less immunogenic it will be. It is possible that there are other candidate residues in the region between Arg484-Ile508, since there may be key residues for the epitope that are common to both human and porcine factor VIII. For example, charged residues are frequently involved in protein-protein interactions, so an alanine substitution for Lys493 is a possible candidate.

This procedure will be carried out in the C2 epitope and the putative third epitope, which is thought to be in the A3 or C1 domains, as well as any other epitopes identified in factor VIII, to prepare hybrid equivalent factor VIII constructs.

Diagnostic Assays

The hybrid human/animal, animal/animal, or equivalent factor VIII cDNA and/or protein expressed therefrom, in whole or in part, can be used in assays as diagnostic reagents for the detection of inhibitory antibodies to human or animal factor VIII or to hybrid human/animal factor or equivalent VIII in substrates, including, for example, samples of serum and body fluids of human patients with factor VIII deficiency. These antibody assays include assays such as ELISA assays, immunoblots, radioimmunoassays, immunodiffusion assays, and assay of factor VIII biological activity (e.g., by coagulation assay). Techniques for preparing these reagents and methods for use thereof are known to those skilled in the art. For example, an immunoassay for detection of inhibitory antibodies in a patient serum sample can include reacting the test sample with a sufficient amount of the hybrid human/animal factor VIII that contains at least one antigenic site, wherein the amount is sufficient to form a detectable complex with the inhibitory antibodies in the sample.

Nucleic acid and amino acid probes can be prepared based on the sequence of the hybrid human/porcine, human/non-human, non-porcine mammalian, animal/animal, or equivalent factor VIII cDNA or protein molecule or fragments thereof. In some embodiments, these can be labeled using dyes or enzymatic, fluorescent, chemiluminescent, or radioactive labels that are commercially available. The amino acid probes can be used, for example, to screen sera or other body fluids where the presence of inhibitors to human, animal, or hybrid human/animal factor VIII is suspected. Levels of inhibitors can be quantitated in patients and compared to healthy controls, and can be used, for example, to determine whether a patient with a factor VIII deficiency can be treated with a hybrid human/animal or hybrid equivalent factor VIII. The cDNA probes can be used, for example, for research purposes in screening DNA libraries.

Pharmaceutical Compositions

Pharmaceutical compositions containing hybrid human/animal, porcine/non-human, non-porcine mammalian, animal-1/animal-2, or equivalent factor VIII, alone or in combination with appropriate pharmaceutical stabilization compounds, delivery vehicles, and/or carrier vehicles, are prepared according to known methods, as described in *Remington's Pharmaceutical Sciences* by E. W. Martin.

In one preferred embodiment, the preferred carriers or delivery vehicles for intravenous infusion are physiological saline or phosphate buffered saline.

In another preferred embodiment, suitable stabilization compounds, delivery vehicles, and carrier vehicles include but are not limited to other human or animal proteins such as albumin.

Phospholipid vesicles or liposomal suspensions are also preferred as pharmaceutically acceptable carriers or delivery vehicles. These can be prepared according to methods known to those skilled in the art and can contain, for example, phosphatidylserine/-phosphatidylcholine or other compositions of phospholipids or detergents that together impart a negative charge to the surface, since factor VIII binds to negatively charged phospholipid membranes. Liposomes may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the hybrid factor VIII is then introduced into the container. The container is then swirled by hand to free lipid material from the sides of the container and to disperse lipid aggregates, thereby forming the liposomal suspension.

The hybrid factor or hybrid equivalent VIII can be combined with other suitable stabilization compounds, delivery vehicles, and/or carrier vehicles, including vitamin K dependent clotting factors, tissue factor, and von Willebrand factor (vWf) or a fragment of vWf that contains the factor VIII binding site, and polysaccharides such as sucrose.

Hybrid or hybrid equivalent factor VIII can also be delivered by gene therapy in the same way that human factor VIII can be delivered, using delivery means such as retroviral vectors. This method consists of incorporation of factor VIII cDNA into human cells that are transplanted directly into a factor VIII deficient patient or that are placed in an implantable device, permeable to the factor VIII molecules but impermeable to cells, that is then transplanted. The preferred method will be retroviral-mediated gene transfer. In this method, an exogenous gene (e.g., a factor VIII cDNA) is cloned into the genome of a modified retrovirus. The gene is inserted into the genome of the host cell by viral machinery where it will be expressed by the cell. The retroviral vector is modified so that it will not produce virus, preventing viral infection of the host. The general principles for this type of therapy are known to those skilled in the art and have been reviewed in the literature (e.g., Kohn, D. B., and P. W. Kantoff, 29 Transfusion 812–820, 1989).

Hybrid factor VIII can be stored bound to vWf to increase the half-life and shelf-life of the hybrid molecule. Additionally, lyophilization of factor VIII can improve the yields of active molecules in the presence of vWf. Current methods for storage of human and animal factor VIII used by commercial suppliers can be employed for storage of hybrid factor VIII. These methods include: (1) lyophilization of factor VIII in a partially-purified state (as a factor VIII "concentrate" that is infused without further purification); (2) immunoaffinity-purification of factor VIII by the Zimmerman method and lyophilization in the presence of albumin, which stabilizes the factor VIII; (3) lyophilization of recombinant factor VIII in the presence of albumin.

Additionally, hybrid factor VIII has been indefinitely stable at 4° C. in 0.6M NaCl, 20 mM MES, and 5 mM $CaCl_2$ at pH 6.0 and also can be stored frozen in these buffers and thawed with minimal loss of activity.

Methods of Treatment

Hybrid or hybrid equivalent factor VIII is used to treat uncontrolled bleeding due to factor VIII deficiency (e.g., intraarticular, intracranial, or gastrointestinal hemorrhage) in hemophiliacs with and without inhibitory antibodies and in patients with acquired factor VIII deficiency due to the development of inhibitory antibodies. The active materials are preferably administered intravenously.

Additionally, hybrid or hybrid equivalent factor VIII can be administered by transplant of cells genetically engineered to produce the hybrid or by implantation of a device containing such cells, as described above.

In a preferred embodiment, pharmaceutical compositions of hybrid or hybrid equivalent factor VIII alone or in combination with stabilizers, delivery vehicles, and/or carriers are infused into patients intravenously according to the same procedure that is used for infusion of human or animal factor VIII.

The treatment dosages of hybrid or hybrid equivalent factor VIII composition that must be administered to a patient in need of such treatment will vary depending on the severity of the factor VIII deficiency. Generally, dosage level is adjusted in frequency, duration, and units in keeping with the severity and duration of each patient's bleeding episode. Accordingly, the hybrid factor VIII is included in the pharmaceutically acceptable carrier, delivery vehicle, or stabilizer in an amount sufficient to deliver to a patient a therapeutically effective amount of the hybrid to stop bleeding, as measured by standard clotting assays.

Factor VIII is classically defined as that substance present in normal blood plasma that corrects the clotting defect in plasma derived from individuals with hemophilia A. The coagulant activity in vitro of purified and partially-purified forms of factor VIII is used to calculate the dose of factor VIII for infusions in human patients and is a reliable indicator of activity recovered from patient plasma and of correction of the in vivo bleeding defect. There are no reported discrepancies between standard assay of novel factor VIII molecules in vitro and their behavior in the dog infusion model or in human patients, according to Lusher, J. M., et al., 328 *New. Engl. J. Med.* 453–459 (1993); Pittman, D. D., et al., 79 *Blood* 389–397 (1992), and Brinkhous et al., 82 *Proc. Natl. Acad. Sci.* 8752–8755 (1985).

Usually, the desired plasma factor VIII level to be achieved in the patient through administration of the hybrid or hybrid equivalent factor VIII is in the range of 30–100% of normal. In a preferred mode of administration of the hybrid or hybrid equivalent factor VIII, the composition is given intravenously at a preferred dosage in the range from about 5 to 50 units/kg body weight, more preferably in a range of 10–50 units/kg body weight, and most preferably at a dosage of 20–40 units/kg body weight; the interval frequency is in the range from about 8 to 24 hours (in severely affected hemophiliacs); and the duration of treatment in days is in the range from 1 to 10 days or until the bleeding episode is resolved. See, e.g., Roberts, H. R., and M. R. Jones, "Hemophilia and Related Conditions—Congenital Deficiencies of Prothrombin (Factor II, Factor V, and Factors VII to XII)," Ch. 153, 1453–1474, 1460, in *Hematology*, Williams, W. J., et al., ed. (1990). Patients with inhibitors may require more hybrid or hybrid equivalent factor VIII, or patients may require less hybrid or hybrid equivalent factor VIII because of its higher specific activity than human factor VIII or decreased antibody reactivity or immunogenicity. As in treatment with human or porcine factor VIII, the amount of hybrid or hybrid equivalent factor VIII infused is defined by the one-stage factor VIII coagulation assay and, in selected instances, in vivo recovery is determined by measuring the factor VIII in the patient's plasma after infusion. It is to be understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition.

Treatment can take the form of a single intravenous administration of the composition or periodic or continuous administration over an extended period of time, as required. Alternatively, hybrid or hybrid equivalent factor VIII can be administered subcutaneously or orally with liposomes in one or several doses at varying intervals of time.

Hybrid or hybrid equivalent factor VIII can also be used to treat uncontrolled bleeding due to factor VIII deficiency in hemophiliacs who have developed antibodies to human factor VIII. In this case, coagulant activity that is superior to that of human or animal factor VIII alone is not necessary. Coagulant activity that is inferior to that of human factor VIII (i.e., less than 3,000 units/mg) will be useful if that activity is not neutralized by antibodies in the patient's plasma.

The hybrid or hybrid equivalent factor VIII molecule and the methods for isolation, characterization, making, and using it generally described above will be further understood with reference to the following non-limiting examples.

EXAMPLE 1
Assay of porcine factor VIII and hybrid human/porcine factor VIII

Porcine factor VIII has more coagulant activity than human factor VIII, based on specific activity of the molecule. These results are shown in Table III in Example 4. This conclusion is based on the use of appropriate standard curves that allow human and porcine factor VIII to be fairly compared. Coagulation assays are based on the ability of factor VIII to shorten the clotting time of plasma derived from a patient with hemophilia A. Two types of assays were employed: the one-stage and the two-stage assay.

In the one-stage assay, 0.1 ml hemophilia A plasma (George King Biomedical, Inc.) was incubated with 0.1 ml activated partial thromboplastin reagent (APTT) (Organon Teknika) and 0.01 ml sample or standard, consisting of diluted, citrated normal human plasma, for 5 min at 37° C. in a water bath. Incubation was followed by addition of 0.1 ml 20 mM $CaCl_2$, and the time for development of a fibrin clot was determined by visual inspection.

A unit of factor VIII is defined as the amount present in 1 ml of citrated normal human plasma. With human plasma as the standard, porcine and human factor VIII activity were compared directly. Dilutions of the plasma standard or purified proteins were made into 0.15M NaCl, 0.02M HEPES, pH 7.4. The standard curve was constructed based on 3 or 4 dilutions of plasma, the highest dilution being 1/50, and on $log_{10}$ clotting time plotted against $log_{10}$ plasma concentration, which results in a linear plot. The units of factor VIII in an unknown sample were determined by interpolation from the standard curve.

The one-stage assay relies on endogenous activation of factor VIII by activators formed in the hemophilia A plasma, whereas the two-stage assay measures the procoagulant activity of preactivated factor VIII. In the two-stage assay, samples containing factor VIII that had been reacted with thrombin were added to a mixture of activated partial thromboplastin and human hemophilia A plasma that had been preincubated for 5 min at 37° C. The resulting clotting times were then converted to units/ml, based on the same human standard curve described above. The relative activity in the two-stage assay was higher than in the one-stage assay because the factor VIII had been preactivated.

EXAMPLE 2
Characterization of the functional difference between human and porcine factor VIII The isolation of porcine and human plasma-derived factor VIII and human recombinant factor VIII have been described in the literature in Fulcher, C. A., and T. S. Zimmerman, 79 *Proc. Natl. Acad. Sci. U.S.A.* 1648–1652 (1982); Toole, J. J., et al., 312 *Nature* 342–347 (1984) (Genetics Institute); Gitschier, J., et al., 312 *Nature* 326–330 (1984) (Genentech); Wood, W. I., et al., 312 *Nature* 330–337 (1984) (Genentech); Vehar, G. A., et al., 312 *Nature* 337–342 (1984) (Genentech); Fass, D. N., et al., 59 *Blood* 594 (1982); Toole, J. J., et al., 83 *Proc. Natl. Acad. Sci. U.S.A.* 5939–5942 (1986). This can be accomplished in several ways. All these preparations are similar in subunit composition, although there is a functional difference in stability between human and porcine factor VIII.

For comparison of human recombinant and porcine factor VIII, preparations of highly-purified human recombinant factor VIII (Cutter Laboratories, Berkeley, CA) and porcine factor VIII (immunopurified as described in Fass, D. N., et al., 59 *Blood* 594 (1982)) were subjected to high-pressure liquid chromatography (HPLC) over a Mono Q™ (Pharmacia-LKB, Piscataway, N.J.) anion-exchange column (Pharmacia, Inc.). The purposes of the Mono Q™ HPLC step were elimination of minor impurities and exchange of human and porcine factor VIII into a common buffer for comparative purposes. Vials containing 1000–2000 units of factor VIII were reconstituted with 5 ml $H_2O$. Hepes (2M at pH 7.4) was then added to a final concentration of 0.02M. Factor VIII was applied to a Mono Q™ HR 5/5 column equilibrated in 0.15M NaCl, 0.02M Hepes, 5 mM $CaCl_2$, at pH 7.4 (Buffer A plus 0.15M NaCl); washed with 10 ml Buffer A+0.15M NaCl; and eluted with a 20 ml linear gradient, 0.15M to 0.90M NaCl in Buffer A at a flow rate of 1 ml/min.

For comparison of human plasma-derived factor VIII (purified by Mono Q™ HPLC) and porcine factor VIII, immunoaffinity-purified, plasma-derived porcine factor VIII was diluted 1:4 with 0.04M Hepes, 5 mM $CaCl_2$, 0.01% Tween-80, at pH 7.4, and subjected to Mono Q™ HPLC under the same conditions described in the previous paragraph for human factor VIII. These procedures for the isolation of human and porcine factor VIII are standard for those skilled in the art.

Column fractions were assayed for factor VIII activity by a one-stage coagulation assay. The average results of the assays, expressed in units of activity per $A_{280}$ of material, are given in Table II, and indicate that porcine factor VIII has at least six times greater activity than human factor VIII when the one-stage assay is used.

TABLE II

COMPARISON OF HUMAN AND PORCINE
FACTOR VIII COAGULANT ACTIVITY

| | Activity (U/A$_{280}$) |
|---|---|
| Porcine | 21,300 |
| Human plasma-derived | 3,600 |
| Human recombinant | 2,400 |

EXAMPLE 3
Comparison of the stability of human and porcine factor VIII

The results of the one-stage assay for factor VIII reflect activation of factor VIII to factor VIIIa in the sample and possibly loss of formed factor VIIIa activity. A direct comparison of the stability of human and porcine factor VIII was made. Samples from Mono Q™ HPLC (Pharmacia, Inc., Piscataway, N.J.) were diluted to the same concentration and buffer composition and reacted with thrombin. At various times, samples were removed for two-stage coagulation assay. Typically, peak activity (at 2 min) was 10-fold greater for porcine than human factor VIIIa, and the activities of both porcine and human factor VIIIa subsequently decreased, with human factor VIIIa activity decreasing more rapidly.

Generally, attempts to isolate stable human factor VIIIa are not successful even when conditions that produce stable porcine factor VIIIa are used. To demonstrate this, Mono Q™ HPLC-purified human factor VIII was activated with thrombin and subjected to Mono S™ cation-exchange (Pharmacia, Inc.) HPLC under conditions that produce stable porcine factor VIIIa, as described by Lollar, J. S., and C. G. Parker, 28 *Biochemistry* 666 (1989).

Human factor VIII, 43 µg/ml (0.2 µM) in 0.2M NaCl, 0.01M Hepes, 2.5 mM CaCl$_2$, at pH 7.4, in 10 ml total volume, was reacted with thrombin (0.036 µM) for 10 min, at which time FPR-CH$_2$Cl D-phenyl-prolyl-arginyl-chloromethyl ketone was added to a concentration of 0.2 µM for irreversible inactivation of thrombin. The mixture then was diluted 1:1 with 40 mM 2-(N-morpholino)ethane sulfonic acid (MES), 5 mM CaCl$_2$, at pH 6.0, and loaded at 2 ml/min onto a Mono S™ HR 5/5 HPLC column (Pharmacia, Inc.) equilibrated in 5 mM MES, 5 mM CaCl$_2$, at pH 6.0 (Buffer B) plus 0.1M NaCl. Factor VIIIa was eluted without column washing with a 20 ml gradient from 0.1M NaCl to 0.9M NaCl in Buffer B at 1 ml/min.

The fraction with coagulant activity in the two-stage assay eluted as a single peak under these conditions. The specific activity of the peak fraction was approximately 7,500 U/A$_{280}$. Sodium dodecyl sulfate-polyacrylamide gel electrophoresis (SDS-PAGE) of the Mono S™ factor VIIIa peak, followed by silver staining of the protein, revealed two bands corresponding to a heterodimeric (A3-C1-C2/A1) derivative of factor VIII. Although the A2 fragment was not identified by silver staining under these conditions because of its low concentration, it was identified as a trace constituent by $^{125}$I-labeling.

In contrast to the results with human factor VIII, porcine factor VIIIa isolated by Mono S™ HPLC under the same conditions had a specific activity 1.6×10$^6$ U/A$_{280}$. Analysis of porcine factor VIIIa by SDS-PAGE revealed 3 fragments corresponding to A1, A2, and A3-C1-C2 subunits, demonstrating that porcine factor VIIIa possesses three subunits.

The results of Mono S™ HPLC of human thrombin-activated factor VIII preparations at pH 6.0 indicate that human factor VIIIa is labile under conditions that yield stable porcine factor VIIIa. However, although trace amounts of A2 fragment were identified in the peak fraction, determination of whether the coagulant activity resulted from small amounts of heterotrimeric factor VIIIa or from heterodimeric factor VIIIa that has a low specific activity was not possible from this method alone.

A way to isolate human factor VIIIa before it loses its A2 subunit is desirable to resolve this question. To this end, isolation was accomplished in a procedure that involves reduction of the pH of the Mono S™ buffers to pH 5. Mono Q™-purified human factor VIII (0.5 mg) was diluted with H$_2$O to give a final composition of 0.25 mg/ml (1 µM) factor VIII in 0.25M NaCl, 0.01M Hepes, 2.5 mM CaCl$_2$, 0.005% Tween-80, at pH 7.4 (total volume 7.0 ml). Thrombin was added to a final concentration of 0.072 µM and allowed to react for 3 min. Thrombin was then inactivated with FPR-CH$_2$Cl (0.2 µM). The mixture then was diluted 1:1 with 40 mM sodium acetate, 5 mM CaCl$_2$, 0.01% Tween-80, at pH 5.0, and loaded at 2 ml/min onto a Mono S™ HR 5/5 HPLC column equilibrated in 0.01M sodium acetate, 5 mM CaCl$_2$, 0.01% Tween-80, at pH 5.0, plus 0.1M NaCl. Factor VIIIa was eluted without column washing with a 20 ml gradient from 0.1M NaCl to 1.0M NaCl in the same buffer at 1 ml/min. This resulted in recovery of coagulant activity in a peak that contained detectable amounts of the A2 fragment as shown by SDS-PAGE and silver staining. The specific activity of the peak fraction was ten-fold greater than that recovered at pH 6.0 (75,000 U/A$_{280}$ v. 7,500 U/A$_{280}$). However, in contrast to porcine factor VIIIa isolated at pH 6.0, which is indefinitely stable at 4° C., human factor VIIIa activity decreased steadily over a period of several hours after elution from Mono S™. Additionally, the specific activity of factor VIIIa purified at pH 5.0 and assayed immediately is only 5% that of porcine factor VIIIa, indicating that substantial dissociation occurred prior to assay.

These results demonstrate that both human and porcine factor VIIIa are composed of three subunits (A1, A2, and A3-C1-C2). Dissociation of the A2 subunit is responsible for the loss of activity of both human and porcine factor VIIIa under certain conditions, such as physiological ionic strength, pH, and concentration. The relative stability of porcine factor VIIIa under certain conditions is because of stronger association of the A2 subunit.

EXAMPLE 4
Preparation of hybrid human/porcine factor VIII by reconstitution with subunits Porcine factor VIII light chains and factor VIII heavy chains were isolated as follows. A 0.5M solution of EDTA at pH 7.4 was added to Mono Q™-purified porcine factor VIII to a final concentration of 0.05M and was allowed to stand at room temperature for 18–24 h. An equal volume of 10 mM histidine-Cl, 10 mM EDTA, 0.02% v/v Tween 80, at pH 6.0 (Buffer B), was added, and the solution was applied at 1 ml/min to a Mono S™ HR 5/5 column previously equilibrated in Buffer A plus 0.25M NaCl. Factor VIII heavy chains did not bind the resin, as judged by SDS-PAGE. Factor VIII light chain was eluted with a linear, 20 ml, 0.1–0.7M NaCl gradient in Buffer A at 1 ml/min and was homogeneous by SDS-PAGE. Factor VIII heavy chains were isolated by mono Q™ HPLC (Pharmacia, Inc., Piscataway, N.J.) in the following way. Factor VIII heavy chains do not adsorb to mono S™ during the purification of factor VIII light chains. The fall-through material that contained factor VIII heavy chains was adjusted to pH 7.2 by addition of 0.5M Hepes buffer, pH 7.4, and applied to a mono Q™ HR5/5 HPLC column (Pharmacia, Inc.) equilibrated in 0.1M NaCl, 0.02M Hepes, 0.01% Tween-80, pH 7.4. The column was washed with 10 ml of this buffer, and factor VIII heavy chains were eluted with a 20 ml 0.1–1.0M NaCl gradient in this buffer. Human light chains and heavy chains were isolated in the same manner.

Human and porcine light and heavy chains were reconstituted according to the following steps. Ten μl human or porcine factor VIII light chain, 100 μg/ml, was mixed in 1M NaCl, 0.02M Hepes, 5 mM $CaCl_2$, 0.01% Tween-80, pH 7.4, with (1) 25 μl heterologous heavy chain, 60 μg/ml, in the same buffer; (2) 10 μl 0.02M Hepes, 0.01% Tween-80, pH 7.4; (3) 5 μl 0.6M $CaCl_2$, for 14 hr at room temperature. The mixture was diluted ¼ with 0.02M MES, 0.01% Tween-80, 5 mM $CaCl_2$ pH 6, and applied to Mono S™ Hr5/5 equilibrated in 0.1M NaCl, 0.02M MES, 0.01% Tween-80, 5 mM $CaCl_2$, pH 6.0. A 20 ml gradient was run from 0.1–1.0M NaCl in the same buffer at 1 ml/min, and 0.5 ml fractions were collected. Absorbance was read at 280 nm of fractions, and fractions were assayed with absorbance for factor VIII activity by the one-stage clotting assay. Heavy chains were present in excess, because free light chain (not associated with heavy chain) also binds Mono S™; excess heavy chains ensure that free light chains are not part of the preparation. Reconstitution experiments followed by Mono S™ HPLC purification were performed with all four possible combinations of chains: human light chain/human heavy chain, human light chain/porcine heavy chain, porcine light chain/porcine heavy chain, porcine light chain/human heavy chain. Table III shows that human light chain/porcine heavy chain factor VIII has activity comparable to native porcine factor VIII (Table II), indicating that structural elements in the porcine heavy chain are responsible for the increased coagulant activity of porcine factor VIII compared to human factor VIII.

TABLE III

COMPARISON OF HYBRID HUMAN/PORCINE FACTOR VIII COAGULANT ACTIVITY WITH HUMAN AND PORCINE FACTOR VIII

| | Activity (U/$A_{280}$) |
|---|---|
| Porcine light chain/porcine heavy chain | 30,600 |
| Human light chain/porcine heavy chain | 44,100 |
| Porcine light chain/human heavy chain | 1,100 |
| Human light chain/human heavy chain | 1,000 |

EXAMPLE 5

Preparation of active hybrid human/porcine factor VIII by reconstitution with domains The porcine A1/A3-C1-C2 dimer, the porcine A2 domain, the human A1/A3-C1-C2 dimer, and the human A2 domain were each isolated from porcine or human blood, according to the method described in Lollar, P., et al., 267(33) *J. Biol. Chem.* 23652–23657 (Nov. 25, 1992). For example, to isolate the porcine A1/A3-C1-C2 dimer, porcine factor VIIIa (140 μg) at pH 6.0 was raised to pH 8.0 by addition of 5N NaOH for 30 minutes, producing dissociation of the A2 domain and 95 percent inactivation by clotting assay. The mixture was diluted 1:8 with buffer B (20 mM HEPES, 5 mM $CaCl_2$, 0.01 % Tween 80, pH 7.4) and applied to a monoS column equilibrated in buffer B. The A1/A3-C1-C2 dimer eluted as a single sharp peak at approximately 0.4M NaCl by using a 0.1–1.0M NaCl gradient in buffer B. To isolate the porcine A2 domain, porcine factor VIIIa was made according to the method of Lollar, P., and C. G. Parker, 28 *Biochem.* 666–674 (1989), starting with 0.64 mg of factor VIII. Free porcine A2 domain was isolated as a minor component (50 μg) at 0.3M NaCl in the monoS™ chromatogram.

Hybrid human/porcine factor VIII molecules were reconstituted from the dimers and domains as follows. The concentrations and buffer conditions for the purified components were as follows: porcine A2, 0.63 μM in buffer A (5 mM MES; 5 mM $CaCl_2$, 0.01% Tween 80, pH 6.0) plus 0.3M NaCl; porcine A1/A3-C1-C2, 0.27 μM in buffer B plus 0.4M NaCl, pH 7.4; human A2, 1 μM in 0.3M NaCl, 10 mM histidine-HCl, 5 mM $CaCl_2$, 0.01 % Tween 20, pH 6.0; human A1/A3-C1-C2, 0.18 μM in 0.5M NaCl, 10 mM histidine-Cl, 2.5 mM $CaCl_2$, 0.1 % Tween 20, pH 6.0. Reconstitution experiments were done by mixing equal volumes of A2 domain and A1/A3-C1-C2 dimer. In mixing experiments with porcine A1/A3-C1-C2 dimer, the pH was lowered to 6.0 by addition of 0.5M MES, pH 6.0, to 70 mM.

The coagulation activities of all four possible hybrid factor VIIIa molecules—[pA2/(hA1/A3-C1-C2)], [hA2/(pA1/A3-C1-C2)], [pA2/(pA1/pA3-C1-C2)], and [hA2/(hA1/A3-C1-C2)]—were obtained by a two-stage clotting assay at various times.

The generation of activity following mixing the A2 domains and A1/A3-C1-C2 dimers was nearly complete by one hour and was stable for at least 24 hours at 37° C. Table IV shows the activity of reconstituted hybrid factor VIIIa molecules when assayed at 1 hour. The two-stage assay, by which the specific activities of factor VIIIa molecules were obtained, differs from the one-stage assay, and the values cannot be compared to activity values of factor VIII molecules obtained by a one-stage assay.

TABLE IV

COMPARISON OF COAGULANT ACTIVITIES OF DOMAIN-SUBSTITUTED HYBRID HUMAN/PORCINE FACTOR VIIIa

| Hybrid fVIIIa | Specific Activity (U/mg) |
|---|---|
| Porcine A2 + Human A1/A3-C1-C2 | 140,000 |
| Porcine A2 + Porcine A1/A3-C1-C2 | 70,000 |
| Human A2 + Porcine A1/A3-C1-C2 | 40,000 |
| Human A2 + Human A1/A3-C1-C2 | 40,000 |

Table IV shows that the greatest activity was exhibited by the porcine A2 domain/human A1/A3-C1-C2 dimer, followed by the porcine A2 domain/porcine A1/A3-C1-C2 dimer.

Thus, when the A2 domain of porcine factor VIIIa was mixed with the A1/A3-C1-C2 dimer of human factor VIIIa, coagulant activity was obtained. Further, when the A2 domain of human factor VIIIa was mixed with the A1/A3-C1-C2 dimer of porcine factor VIIIa, coagulant activity was obtained. By themselves, the A2, A1, and A3-C1-C2 regions have no coagulant activity.

EXAMPLE 6

Isolation and sequencing of the A2 domain of porcine factor VIII

Only the nucleotide sequence encoding the B domain and part of the A2 domain of porcine factor VIII has been sequenced previously (Toole, J. J., et al., 83 *Proc. Natl. Acad. Sci. U.S.A.* 5939–5942 (1986)). The cDNA and predicted amino acid sequences (SEQ ID NOs:5 and 6, respectively) for the entire porcine factor VIII A2 domain are disclosed herein.

The porcine factor VIII A2 domain was cloned by reverse transcription of porcine spleen total RNA and PCR amplification; degenerate primers based on the known human factor VIII cDNA sequence and an exact porcine primer based on a part of the porcine factor VIII sequence were used. A 1 kb PCR product was isolated and amplified by insertion into a Bluescript™ (Stratagene) phagemid vector.

The porcine A2 domain was completely sequenced by dideoxy sequencing. The cDNA and predicted amino acid sequences are as described in SEQ ID NOs:5 and 6, respectively.

EXAMPLE 7

Preparation of recombinant hybrid human/animal factor VIII

The nucleotide and predicted amino acid sequences (SEQ ID NOs:1 and 2, respectively) of human factor VIII have been described in the literature (Toole, J. J., et al., 312 *Nature* 342–347 (1984) (Genetics Institute); Gitschier, J., et al., 312 *Nature* 326–330 (1984) (Genentech); Wood, W. I., et al., 312 *Nature* 330–337 (1984) (Genentech); Vehar, G. A., et al., 312 *Nature* 337–342 (1984) (Genentech)).

Making recombinant hybrid human/animal factor VIII requires that a region of human factor VIII cDNA (Biogen Corp.) be removed and the animal cDNA sequence having sequence identity be inserted. Subsequently, the hybrid CDNA is expressed in an appropriate expression system. As an example, hybrid factor VIII cDNAs were cloned in which some or all of the porcine A2 domain was substituted for the corresponding human A2 sequences. Initially, the entire cDNA sequence corresponding to the A2 domain of human factor VIII and then a smaller part of the A2 domain was looped out by oligonucleotide-mediated mutagenesis, a method commonly known to those skilled in the art (see, e.g., Sambrook, J., E. F. Fritsch, and T. Maniatis, *Molecular Cloning: A Laboratory Manual*, Chapter 15, Cold Spring Harbor Press, Cold Spring Harbor, 1989). The steps were as follows.

Materials.

Methoxycarbonyl-D-cyclohexylglycyl-glycl-arginine-p-nitroanilide (Spectrozyme™ Xa) and anti-factor VIII monoclonal antibodies ESH4 and ESH8 were purchased from American Diagnostica (Greenwich, Conn.). Unilamellar phosphatidylcholine/phosphatidylserine (75/25, w/w) vesicles were prepared according to the method of Barenholtz, Y., et al., 16 *Biochemistry* 2806–2810 (1977). Recombinant desulfatohirudin was obtained from Dr. R. B. Wallis, Ciba-Geigy Pharmaceuticals (Cerritos, Calif.). Porcine factors IXa, X, Xa, and thrombin were isolated according to the methods of Lollar, P., et al., 63 *Blood* 1303–1306 (1984), and Duffy, E. J., and P. Lollar, 207 *J. Biol. Chem.* 7621–7827 (1992). Albumin-free pure recombinant human factor VIII was obtained from Baxter-Biotech (Deerfield, Ill.).

Cloning of the porcine factor VIII A2 domain.

The cDNA encoding the porcine A2 domain was obtained following PCR of reverse-transcribed porcine spleen mRNA isolated as described by Chomczyneki, P., and Sacohi, N., 162 *Anal. Biochem.* 156–159 (1987). cDNA was prepared using the first-strand cDNA synthesis kit with random hexamers as primers (Pharmacia, Piscataway, N.J.). PCR was carried out using a 5'-terminal degenerate primer 5' AARCAYCCNAARACNTGGG 3' (SEQ ID NO:11), based on known limited porcine A2 amino acid sequence, and a 3'-terminal exact primer, 5' GCTCGCACTAGGGGGTCT-TGAATTC 3' (SEQ ID NO:12), based on known porcine DNA sequence immediately 3' of the porcine A2 domain. These oligonucleotides correspond to nucleotides 1186–1203 and 2289–2313 in the human sequence (SEQ ID NO:1). Amplification was carried out for 35 cycles (1 minute 94° C., 2 minutes 50° C., 2 minutes 72° C.) using Taq DNA polymerase (Promega Corp., Madison, Wisc.). The 1.1-kilobase amplified fragment was cloned into pBluescript II KS-(Stratagene) at the EcoRV site using the T-vector procedure, as described by Murchuk, D., et al., 19 *Nucl. Acids Res.* 1154 (1991). *Escherichia coli* XL1-Blue-competent cella were transformed, and plasmid DNA was isolated. Sequencing was carried out in both directions using Sequenase™ version 2.0 (U.S. Biochemical Corp., a Division of Amersham LifeScience, Inc., Arlington Hts, Ill.). This sequence was confirmed by an identical sequence that was obtained by direct sequencing of the PCR product from an independent reverse transcription of spleen RNA from the same pig (CircumVent™, New England Biolabs, Beverly, Mass.). The region containing the epitope for autoantibody RC was identified as 373–536 in human factor VIII (SEQ ID NO:2).

Construction and expression of a hybrid human/porcine factor VIII cDNA.

B-domainless human factor VIII (HB–, from Biogen, Inc. Cambridge, Mass.), which lacks sequences encoding for amino acid residues 741–1648 (SEQ ID NO:2), was used as the starting material for construction of a hybrid human/porcine factor VIII. HB– was cloned into the expression vector Reneo. To facilitate manipulation, the cDNA for factor VIII was isolated as a XhoI/HpaI fragment from ReNeo⁻ and cloned into Xho1/EcoRV digested pBlueScript II KS⁻. An oligonucleotide, 5' CCTTCCTTTATC-CAAATACGTAGATCAAGAGGAAATTGAC 3' (SEQ ID NO:7), was used in a site-directed mutagenesis reaction using uracil-containing phage DNA, as described by Kunkel, T. A., et al., 204 *Meth. Enzymol.* 125–139 (1991), to simultaneously loop-out the human A2 sequence (nucleotides 1169–2304 in SEQ ID NO:1) and introduce a SnaBI restriction site. The A2-domainless human factor VIII containing plasmid was digested with SnaBI followed by addition of ClaI linkers. The porcine A2 domain was then amplified by PCR using the phosphorylated 5' primer 5' GTAGCGTTGCCAAGAAGCACCCTAAGACG 3' (SEQ ID NO:8) and 3' primer 5' GAAGAGTAGTACGAGT-TATTTCTCTGGGTTCAATGAC 3' (SEQ ID NO:9), respectively. ClaI linkers were added to the PCR product followed by ligation into the human factor VIII-containing vector. The A1/A2 and A2/A3 junctions were corrected to restore the precise thrombin cleavage and flanking sequences by site-directed mutagenesis using the oligonucleotide shown in SEQ ID NO:8 and nucleotides 1–22 (5' GAA . . . TTC in SEQ ID NO:9) to correct the 5'- and 3'-terminal junctions, respectively. In the resulting construct, designated HP1, the human A2 domain was exactly substituted with the porcine A2 domain. A preliminary product contained an unwanted thymine at the A1-A2 junction as a result of the PCR amplification of the porcine A2 domain. This single base can be looped out by use of the mutagenic oligonucleotide 5' CCTTTATCCAAATACG-TAGCGTTTGCCAAGAAG 3' (SEQ ID NO:10).

A region containing 63% of the porcine NH$_2$-terminal A2 domain, which encompasses the putative A2 epitope, was substituted for the homologous human sequence of B-domainless cDNA by exchanging SpeI/BamHI fragments between the pBluescript plasmids containing human factor VIII and human/porcine A2 factor VIII cDNA. The sequence was confirmed by sequencing the A2 domain and splice sites. Finally, a SpeI/ApaI fragment, containing the entire A2 sequence, was substituted in place of the corresponding sequence in HB–, producing the HP2 construct.

Preliminary expression of HB– and HP2 in COS-7 cells was tested after DEAE-dextran-mediated DNA transfection, as described by Seldon, R. F., in *Current Protocols in Molecular Biology* (Ausubel, F. M., et al., eds), pp. 9.21–9.26, Wiley Interscience, N.Y. After active factor VIII expression was confirmed and preliminary antibody inhibition studies were done, HB– and HP2 DNA were then stably transfected into baby hamster kidney cells using liposome-mediated transfection (Lipofectin®, Life Technologies, Inc., Gaithersburg, Md.). Plasmid-containing clones were selected for G418 resistance in Dulbecco's modified Eagle's medium-F12, 10% fetal calf serum (DMEM-F12/10% fetal calf serum) containing 400 μg/ml G418, followed by maintenance in DMEM-F12/10% fetal calf serum containing 100 μg/ml G418. Colonies showing maximum expression of HB– and HP2 factor VIII activity were selected by ring cloning and expanded for further characterization.

HB– and HP2 factor VIII expression was compared by plasma-free factor VIII assay, one-stage clotting assay, and enzyme-linked immunosorbent assay using purified recombinant human factor VIII as a standard. Specific coagulant activities of 2600 and 2580 units/mg were obtained for HB– and HP2, respectively. HB– and HP2 produced 1.2 and 1.4 units/ml/48 hours/$10^7$ cells, respectively. This is identical to that of the wild type construct (2,600±200 units/mg). The specific activities of HB– and HP2 were indistinguishable in the plasma-free factor VIII assay.

Construction and expression of hybrid human/non-human, non-porcine mammalian and hybrid equivalent factor VIII.

Cloning of other animal A1, A3, C1, and C2 domains and part domains is feasible with the same strategy that was used for cloning the porcine A2 domain. Fragments of these domains can be cloned by the looping out mutagenesis technique. Excision of the corresponding domains in human factor VIII and any fragments thereof, including single amino acid eliminations, is feasible by looping out mutagenesis as described above. All possible domain replacements, fragments of domain replacements, or single amino acid residue replacements are possible by this approach combined with site-directed mutagenesis techniques, such as splicing by overlap extension and alanine scanning mutagenesis.

The biological activity of recombinant hybrid human/animal and equivalent factor VIII with A1, A2, A3, C1, and/or C2 domain substitutions can be evaluated initially by use of a COS-cell mammalian transient expression system. Hybrid human/animal and equivalent cDNA can be transfected into COS cells, and supernatants can be analyzed for factor VIII activity by use of one-stage and two-stage coagulation assays as described above. Additionally, factor VIII activity can be measured by use of a chromogenic substrate assay, which is more sensitive and allows analysis of larger numbers of samples. Similar assays are standard in the assay of factor VIII activity (Wood, W. I., et al., 312 *Nature* 330–337, 1984; Toole, J. J., et al., 312 *Nature* 342–347, 1984). Expression of recombinant factor VIII in COS cells is also a standard procedure (Toole, J. J., et al., 312 *Nature* 342–347, 1984; Pittman, D. D., and R. J. Kaufman, 85 *Proc. Natl. Acad. Sci. U.S.A.* 2429–2433, 1988). The human factor VIII CDNA used as starting material for the recombinant molecules described herein has been expressed in COS cells yielding a product with biological activity. This material, as described above, can be used as a standard to compare hybrid human/animal factor VIII molecules. The activity in the assays is converted to a specific activity for proper comparison of the hybrid molecules. For this, a measurement of the mass of factor VIII produced by the cells is necessary and can be done by immunoassay with purified human and/or animal factor VIII as standards. Immunoassays for factor VIII are routine for those skilled in the art (See, e.g., Lollar, P., et al., 71 *Blood* 137–143, 1988).

EXAMPLE 8

Determination of inhibitory activity in hybrid human/animal and equivalent factor VIII Sequences of human and animal factor VIII likely to be involved as epitopes (i.e., as recognition sites for inhibitory antibodies that react with factor VIII) can be determined using routine procedures, for example through use of assay with antibodies to factor VIII combined with site directed mutagenesis techniques such as splicing by overlap extension methods (SOE), as shown below. Sequences of animal factor VIII that are not antigenic compared to corresponding antigenic human sequences can be identified, and substitutions can be made to insert animal sequences and delete human sequences according to standard recombinant DNA methods. Sequences of amino acids such as alanine residues having no known sequence identity to factor VIII can also be substituted by standard recombinant DNA methods or by alanine scanning mutagenesis. Porcine factor VIII reacts less than human factor VIII with some inhibitory antibodies; this provides a basis for current therapy for patients with inhibitors. After the recombinant hybrids are made, they can be tested in vitro for reactivity with routine assays, including the Bethesda inhibitor assay. Those constructs that are less reactive than native human factor VIII and native animal factor VIII are candidates for replacement therapy.

The epitopes to which most, if not all, inhibitory antibodies reactive with human factor VIII are directed are thought to reside in two regions in the 2332 amino acid human factor VIII molecule, the A2 domain (amino acid residues 373–740) and the C2 domain (amino acid residues 2173–2332, both sequences shown in SEQ ID NO:2). The A2 epitope has been eliminated by making a recombinant hybrid human/porcine factor VIII molecule in which part of the human A2 domain is replaced by the porcine sequence having sequence identity to the replaced human amino acid sequence. This was accomplished, as described in Example 7, by cloning the porcine A2 domain by standard molecular biology techniques and then cutting and splicing within the A2 domain using restriction sites. In the resulting construct, designated HP2, residues 373–604 (SEQ ID NO:4) of porcine factor VIII were substituted into the human A2 domain. HP2 was assayed for immunoreactivity with anti-human factor VIII antibodies using the following methods.

Factor VIII enzyme-linked immunosorbent assay.

Microtiter plate wells were coated with 0.15 ml of 6 μg/ml ESH4, a human factor VIII light-chain antibody, and incubated overnight. After the plate was washed three times with $H_2O$, the wells were blocked for 1 hour with 0.15M NaCl, 10 mM sodium phosphate, 0.05% Tween 20, 0.05% nonfat dry milk, 0.05% sodium azide, pH 7.4. To increase sensitivity, samples containing factor VIII were activated with 30 nM thrombin for 15 minutes. Recombinant desulfatohirudin then was added at 100 nM to inhibit thrombin. The plate was washed again and 0.1 ml of sample or pure recombinant human factor VIII (10–600 ng/ml), used as the standard, were added. Following a 2 hour incubation, the plate was washed and 0.1 ml of biotinylated ESH8, another factor VIII light-chain antibody, was added to each well. ESH8 was biotinylated using the Pierce sulfosuccinimidyl-6-(biotinamide)hexanoate biotinylation kit. After a 1 hour incubation, the plate was washed and 0.1 ml of strepavidin alkaline phosphatase was added to each well. The plate was developed using the Bio-Rad alkaline phosphatase substrate reagent kit, and the resulting absorbance at 405 nm for each well was determined by using a Vmax microtiter plate reader (Molecular Devices, Inc., Sunnyville, Calif.). Unknown factor VIII concentrations were determined from the linear portion of the factor VIII standard curve.

Factor VIII assays.

HB– and HB2 factor VIII were measured in a one-stage clotting assay, which was performed as described above (Bowie, E. J. W., and C. A. Owen, in *Disorders of Hemostasis* (Ratnoff and Forbes, eds) pp. 43–72, Grunn & Stratton, Inc., Orlando, Fla. (1984)), or by a plasma-free assay as follows. HB-- or HP2 factor VIII was activated by 40 nM thrombin in 0.15M NaCl, 20 nM HEPES, 5 mM $CaCl_2$, 0.01% Tween 80, pH 7.4, in the presence of 10 nM factor IXa, 425 nM factor X, and 50 µM unilamellar phosphatidylserine/phosphatidylcholine (25/75, w/w) vesicles. After 5 minutes, the reaction was stopped with 0.05M EDTA and 100 nM recombinant desulfatohirudin, and the resultant factor Xa was measured by chromogenic substrate assay, according to the method of Hill-Eubanks, D. C., and P. Lollar, 265 *J. Biol. Chem.* 17854–17858 (1990). Under these conditions, the amount of factor Xa formed was linearly proportional to the starting factor VIII concentration as judged by using purified recombinant human factor VIII (Baxter Biotech, Deerfield, Ill.) as the standard.

Prior to clotting assay, HB– or HP2 factor VIII were concentrated from 48 hour conditioned medium to 10–15 units/ml by heparin-Sepharose™ chromatography. HB– or HP2 factor VIII were added to hemophilia A plasma (George King Biomedical) to a final concentration of 1 unit/ml. Inhibitor titers in RC or MR plasma or a stock solution of mAb 413 IgG (4 µM) were measured by the Bethesda assay as described by Kasper, C. K., et al., 34 *Thromb. Diath. Haemorrh.* 869–872 (1975). Inhibitor IgG was prepared as described by Leyte, A., et al., 266 *J. Biol. Chem.* 740–746 (1991).

HP2 does not react with anti-A2 antibodies. Therefore, residues 373–603 must contain an epitope for anti-A2 antibodies.

Preparation of hybrid human/porcine factor VIII and assay by splicing by overlap extension (SOE).

Several more procoagulant recombinant hybrid human/porcine factor VIII B-domainless molecules with porcine amino acid substitutions in the human A2 region have been prepared to further narrow the A2 epitope. Besides restriction site techniques, the "splicing by overlap extension" method (SOE) as described by Ho, S. N., et al., 77 *Gene* 51–59 (1989), has been used to substitute any arbitrary region of porcine factor VIII cDNA. In SOE, the splice site is defined by overlapping oligonucleotides that can be amplified to produce the desired cDNA by PCR. Ten cDNA constructs, designated HP4 through HP13, have been made. They were inserted into the ReNeo expression vector, stably transfected into baby hamster kidney cells, and expressed to high levels [0.5–1 μg (approximately 3–6 units)/$10^7$ cells/24 hours, as described in Example 7. Factor VIII coagulant activity was determined in the presence and absence of a model murine monoclonal inhibitory antibody specific for the A2 domain, mAb413. In the absence of inhibitor, all of the constructs had a specific coagulant activity that was indistinguishable from B(−) human factor VIII.

The hybrid human/porcine factor VIII constructs were assayed for reactivity with the anti-A2 inhibitor mAb413 using the Bethesda assay (Kasper, C. K., et al., 34 *Thromb. Diath. Haemorrh.* 869–872 (1975)). The Bethesda unit (BU) is the standard method for measuring inhibitor titers. The results are shown in Table V, and are compared to recombinant human factor VIII.

TABLE V

COMPARISON OF IMMUNOREACTIVITY OF AMINO ACID-SUBSTITUTED HYBRID HUMAN/PORCINE FACTOR VIII

| Construct | Porcine Substitution | Inhibition mAb413 (BU/mg IgG) |
|---|---|---|
| Human B(-) fVIII | None | 1470 |
| HP4 | 373–540 | <0.7 |
| HP5 | 373–508 | <0.7 |
| HP6 | 373–444 | 1450 |
| HP7 | 445–508 | <0.7 |
| HP8 | 373–483 | 1250 |
| HP9 | 484–508 | <0.7 |
| HP10 | 373–403 | 1170 |
| HP11 | 404–508 | <0.7 |
| HP12 | 489–508 | <0.7 |
| HP13 | 484–488 | <0.7 |

The boundaries of porcine substitutions are defined by the first amino acids that differ between human and porcine factor VIII at the $NH_2$-terminal and C-terminal ends of the insertion. As shown in Table V, if the Bethesda titer is not measurable (<0.7 BU/mg IgG), then an A2 epitope lies in the region of substituted porcine sequence. The epitope has been progressively narrowed to residues 484–509 (SEQ ID NO:2), consisting of only 25 residues, as exemplified by non-reactivity of mAb413 with HP9. Among constructs HP4 through HP11, HP9 was the most "humanized" construct that did not react with the inhibitor. This indicates that a critical region in the A2 epitope is located within the sequence Arg484-Ile508.

Based on a comparison between human and porcine factor VIII of the amino acid sequence in this critical region, two more constructs, HP12 and HP13, were made, in which corresponding porcine amino acid sequence was substituted for human amino acids 489–508 and 484–488, respectively. Neither reacts with mAb413. This indicates that residues on each side of the Arg488-Ser489 bond are important for reaction with A2 inhibitors. In HP12 only 5 residues are non-human, and in HP13 only 4 residues are non-human. The 484–508, 484–488, and 489–508 porcine substituted hybrids displayed decreased inhibition by A2 inhibitors from four patient plasmas, suggesting that there is little variation in the structure of the A2 epitope according to the inhibitor population response.

The reactivity of the most humanized constructs, HP9, HP12, and HP13, with two anti-A2 IgG5 preparations prepared from inhibitor plasmas was determined. Like mAb413, these antibodies did not react with HP9, HP12, and HP13, but did react with the control constructs HB(−) and HP8.

The region between 484–508 can be further analyzed for final identification of the critical A2 epitope, using the same procedures.

The methods described in Examples 7 and 8 can be used to prepare other hybrid human/non-porcine mammalian factor VIII with amino acid substitution in the human A2 or other domains, hybrid human/animal or animal/animal factor VIII with amino acid substitution in any domain, or hybrid factor VIII equivalent molecules or fragments of any of these, such hybrid factor VIII having reduced or absent immunoreactivity with anti-factor VIII antibodies.

Although only preferred embodiments are specifically illustrated and described herein, it will be appreciated that many modifications and variations of the present invention are possible in light of the above teachings and within the purview of the appended claims without departing from the spirit and intended scope of the invention.

We claim:

1. A method for treating human patients with factor VIII deficiency comprising administering to the patient a hybrid human/non-human mammalian factor VIII molecule, said molecule comprising at least one specific sequence including one or more unique amino acids of the factor VIII of one species and shorter than a domain substituted for the corresponding sequence one or more amino acids of the factor VIII of the other species, wherein at least one specific sequence including one or more unique amino acids of the factor VIII of the other sequence corresponds to human amino acid sequence as shown in SEQ ID NO:2 selected from the group consisting of amino acids 373–540, 373–508, 445–508, 484–508, 404–508, 489–508, and 484–488.

2. The method of claim 1, wherein the molecule is a hybrid human/porcine molecule, the corresponding sequence to be substituted by the specific sequence is human, and the specific sequence is porcine.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 9009 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapien
        ( F ) TISSUE TYPE: Liver ( i x ) FEATURE:
        ( A ) NAME/KEY: misc_feature (Domain Structure)
        ( B ) LOCATION: 5125 . . . 7053
        ( D ) OTHER INFORMATION: /note= "Equivalent to the A3-C1-C2 domain"

( i x ) FEATURE:
        ( A ) NAME/KEY: misc_feature (Domain Structure)
        ( B ) LOCATION: 1 . . . 2277
        ( D ) OTHER INFORMATION: /note="Equivalent to the A1-A2 domain."

( i x ) FEATURE:
        ( A ) NAME/KEY: Domain
        ( B ) LOCATION: 1..2277
        ( D ) OTHER INFORMATION: /note= "cDNA encoding human factor VIII."

( x i ) SEQUENCE DESCRIPTION: SEQ ID NO:1:

```
CAGTGGGTAA GTTCCTTAAA TGCTCTGCAA AGAAATTGGG ACTTTTCATT AAATCAGAAA      60
TTTTACTTTT TTCCCCTCCT GGGAGCTAAA GATATTTTAG AGAAGAATTA ACCTTTTGCT     120
TCTCCAGTTG AACATTTGTA GCAATAAGTC ATGCAAATAG AGCTCTCCAC CTGCTTCTTT     180
CTGTGCCTTT TGCGATTCTG CTTTAGTGCC ACCAGAAGAT ACTACCTGGG TGCAGTGGAA     240
CTGTCATGGG ACTATATGCA AAGTGATCTC GGTGAGCTGC CTGTGGACGC AAGATTTCCT     300
CCTAGAGTGC CAAAATCTTT TCCATTCAAC ACCTCAGTCG TGTACAAAAA GACTCTGTTT     360
GTAGAATTCA CGGTTCACCT TTTCAACATC GCTAAGCCAA GGCCACCCTG GATGGGTCTG     420
CTAGGTCCTA CCATCCAGGC TGAGGTTTAT GATACAGTGG TCATTACACT TAAGAACATG     480
GCTTCCCATC CTGTCAGTCT TCATGCTGTT GGTGTATCCT ACTGGAAAGC TTCTGAGGGA     540
GCTGAATATG ATGATCAGAC CAGTCAAAGG GAGAAAGAAG ATGATAAAGT CTTCCCTGGT     600
GGAAGCCATA CATATGTCTG GCAGGTCCTG AAAGAGAATG GTCCAATGGC CTCTGACCCA     660
CTGTGCCTTA CCTACTCATA TCTTTCTCAT GTGGACCTGG TAAAAGACTT GAATTCAGGC     720
CTCATTGGAG CCCTACTAGT ATGTAGAGAA GGGAGTCTGG CCAAGGAAAA GACACAGACC     780
TTGCACAAAT TTATACTACT TTTTGCTGTA TTTGATGAAG GGAAAGTTG GCACTCAGAA     840
ACAAAGAACT CCTTGATGCA GGATAGGGAT GCTGCATCTG CTCGGGCCTG GCCTAAAATG     900
CACACAGTCA ATGGTTATGT AAACAGGTCT CTGCCAGGTC TGATTGGATG CCACAGGAAA     960
TCAGTCTATT GGCATGTGAT TGGAATGGGC ACCACTCCTG AAGTGCACTC AATATTCCTC    1020
GAAGGTCACA CATTTCTTGT GAGGAACCAT CGCCAGGCGT CCTTGGAAAT CTCGCCAATA    1080
```

```
ACTTTCCTTA CTGCTCAAAC ACTCTTGATG GACCTTGGAC AGTTTCTACT GTTTTGTCAT    1140
ATCTCTTCCC ACCAACATGA TGGCATGGAA GCTTATGTCA AAGTAGACAG CTGTCCAGAG    1200
GAACCCCAAC TACGAATGAA AAATAATGAA GAAGCGGAAG ACTATGATGA TGATCTTACT    1260
GATTCTGAAA TGGATGTGGT CAGGTTTGAT GATGACAACT CTCCTTCCTT TATCCAAATT    1320
CGCTCAGTTG CCAAGAAGCA TCCTAAAACT TGGGTACATT ACATTGCTGC TGAAGAGGAG    1380
GACTGGGACT ATGCTCCCTT AGTCCTCGCC CCCGATGACA GAAGTTATAA AGTCAATAT     1440
TTGAACAATG GCCCTCAGCG GATTGGTAGG AAGTACAAAA AAGTCCGATT TATGGCATAC    1500
ACAGATGAAA CCTTTAAGAC TCGTGAAGCT ATTCAGCATG AATCAGGAAT CTTGGGACCT    1560
TTACTTTATG GGGAAGTTGG AGACACACTG TTGATTATAT TAAGAATCA  AGCAAGCAGA    1620
CCATATAACA TCTACCCTCA CGGAATCACT GATGTCCGTC CTTTGTATTC AAGGAGATTA    1680
CCAAAAGGTG TAAAACATTT GAAGGATTTT CCAATTCTGC CAGGAGAAAT ATTCAAATAT    1740
AAATGGACAG TGACTGTAGA AGATGGGCCA ACTAAATCAG ATCCTCGGTG CCTGACCCGC    1800
TATTACTCTA GTTTCGTTAA TATGGAGAGA GATCTAGCTT CAGGACTCAT GGCCCTCTC     1860
CTCATCTGCT ACAAAGAATC TGTAGATCAA AGAGGAAACC AGATAATGTC AGACAAGAGG    1920
AATGTCATCC TGTTTTCTGT ATTTGATGAG AACCGAAGCT GGTACCTCAC AGAGAATATA    1980
CAACGCTTTC TCCCCAATCC AGCTGGAGTG CAGCTTGAGG ATCCAGAGTT CCAAGCCTCC    2040
AACATCATGC ACAGCATCAA TGGCTATGTT TTTGATAGTT TGCAGTTGTC AGTTTGTTTG    2100
CATGAGGTGG CATACTGGTA CATTCTAAGC ATTGGAGCAC AGACTGACTT CCTTTCTGTC    2160
TTCTTCTCTG GATATACCTT CAAACACAAA ATGGTCTATG AAGACACACT CACCCTATTC    2220
CCATTCTCAG GAGAAACTGT CTTCATGTCG ATGGAAAACC CAGGTCTATG GATTCTGGGG    2280
TGCCACAACT CAGACTTTCG GAACAGAGGC ATGACCGCCT TACTGAAGGT TTCTAGTTGT    2340
GACAAGAACA CTGGTGATTA TTACGAGGAC AGTTATGAAG ATATTTCAGC ATACTTGCTG    2400
AGTAAAAACA ATGCCATTGA ACCAAGAAGC TTCTCCCAGA ATTCAAGACA CCCTAGCACT    2460
AGGCAAAAGC AATTTAATGC CACCACAATT CCAGAAAATG ACATAGAGAA GACTGACCCT    2520
TGGTTTGCAC ACAGAACACC TATGCCTAAA ATACAAAATG TCTCCTCTAG TGATTTGTTG    2580
ATGCTCTTGC GACAGAGTCC TACTCCACAT GGGCTATCCT TATCTGATCT CCAAGAAGCC    2640
AAATATGAGA CTTTTTCTGA TGATCCATCA CCTGGAGCAA TAGACAGTAA TAACAGCCTG    2700
TCTGAAATGA CACACTTCAG GCCACAGCTC CATCACAGTG GGACATGGT  ATTTACCCCT    2760
GAGTCAGGCC TCCAATTAAG ATTAAATGAG AAACTGGGGA CAACTGCAGC AACAGAGTTG    2820
AAGAAACTTG ATTTCAAAGT TTCTAGTACA TCAAATAATC TGATTTCAAC AATTCCATCA    2880
GACAATTTGG CAGCAGGTAC TGATAATACA AGTTCCTTAG GACCCCCAAG TATGCCAGTT    2940
CATTATGATA GTCAATTAGA TACCACTCTA TTTGGCAAAA AGTCATCTCC CCTTACTGAG    3000
TCTGGTGGAC CTCTGAGCTT GAGTGAAGAA ATAATGATT  CAAAGTTGTT AGAATCAGGT    3060
TTAATGAATA GCCAAGAAAG TTCATGGGGA AAAAATGTAT CGTCAACAGA GAGTGGTAGG    3120
TTATTTAAAG GGAAAAGAGC TCATGGACCT GCTTTGTTGA CTAAAGATAA TGCCTTATTC    3180
AAAGTTAGCA TCTCTTTGTT AAAGACAAAC AAAACTTCCA ATAATTCAGC AACTAATAGA    3240
AAGACTCACA TTGATGGCCC ATCATTATTA ATTGAGAATA GTCCATCAGT CTGGCAAAAT    3300
ATATTAGAAA GTGACACTGA GTTTAAAAAA GTGACACCTT TGATTCATGA CAGAATGCTT    3360
ATGGACAAAA ATGCTACAGC TTTGAGGCTA AATCATATGT CAAATAAAAC TACTTCATCA    3420
AAAACATGG  AAATGGTCCA ACAGAAAAAA GAGGGCCCCA TTCCACCAGA TGCACAAAAT    3480
```

```
CCAGATATGT CGTTCTTTAA GATGCTATTC TTGCCAGAAT CAGCAAGGTG GATACAAAGG      3540

ACTCATGGAA AGAACTCTCT GAACTCTGGG CAAGGCCCCA GTCCAAAGCA ATTAGTATCC      3600

TTAGGACCAG AAAAATCTGT GGAAGGTCAG AATTTCTTGT CTGAGAAAAA CAAAGTGGTA      3660

GTAGGAAAGG GTGAATTTAC AAAGGACGTA GGACTCAAAG AGATGGTTTT TCCAAGCAGC      3720

AGAAACCTAT TTCTTACTAA CTTGGATAAT TTACATGAAA ATAATACACA CAATCAAGAA      3780

AAAAAAATTC AGGAAGAAAT AGAAAGAAG GAAACATTAA TCCAAGAGAA TGTAGTTTTG       3840

CCTCAGATAC ATACAGTGAC TGGCACTAAG AATTTCATGA AGAACCTTTT CTTACTGAGC      3900

ACTAGGCAAA ATGTAGAAGG TTCATATGAG GGGCATATG CTCCAGTACT TCAAGATTTT       3960

AGGTCATTAA ATGATTCAAC AAATAGAACA AGAAACACA CAGCTCATTT CTCAAAAAAA       4020

GGGGAGGAAG AAAACTTGGA AGGCTTGGGA AATCAAACCA AGCAAATTGT AGAGAAATAT     4080

GCATGCACCA CAAGGATATC TCCTAATACA AGCCAGCAGA ATTTGTCAC GCAACGTAGT       4140

AAGAGAGCTT TGAAACAATT CAGACTCCCA CTAGAAGAAA CAGAACTTGA AAAAGGATA       4200

ATTGTGGATG ACACCTCAAC CCAGTGGTCC AAAAACATGA ACATTTGAC CCCGAGCACC       4260

CTCACACAGA TAGACTACAA TGAGAAGGAG AAAGGGGCCA TTACTCAGTC TCCCTTATCA     4320

GATTGCCTTA CGAGGAGTCA TAGCATCCCT CAAGCAAATA GATCTCCATT ACCCATTGCA     4380

AAGGTATCAT CATTTCCATC TATTAGACCT ATATATCTGA CCAGGGTCCT ATTCCAAGAC     4440

AACTCTTCTC ATCTTCCAGC AGCATCTTAT AGAAAGAAAG ATTCTGGGGT CCAAGAAAGC    4500

AGTCATTTCT TACAAGGAGC CAAAAAAAAT AACCTTTCTT TAGCCATTCT AACCTTGGAG     4560

ATGACTGGTG ATCAAAGAGA GGTTGGCTCC CTGGGGACAA GTGCCACAAA TTCAGTCACA     4620

TACAAGAAAG TTGAGAACAC TGTTCTCCCG AAACCAGACT GCCCAAAAC ATCTGGCAAA      4680

GTTGAATTGC TTCCAAAAGT TCACATTTAT CAGAAGGACC TATTCCCTAC GGAAACTAGC     4740

AATGGGTCTC CTGGCCATCT GGATCTCGTG GAAGGGAGCC TTCTTCAGGG AACAGAGGGA    4800

GCGATTAAGT GGAATGAAGC AAACAGACCT GGAAAAGTTC CCTTTCTGAG AGTAGCAACA    4860

GAAAGCTCTG CAAAGACTCC CTCCAAGCTA TTGGATCCTC TTGCTTGGGA TAACCACTAT     4920

GGTACTCAGA TACCAAAAGA AGAGTGGAAA TCCCAAGAGA AGTCACCAGA AAAAACAGCT    4980

TTTAAGAAAA AGGATACCAT TTTGTCCCTG AACGCTTGTG AAAGCAATCA TGCAATAGCA     5040

GCAATAAATG AGGGACAAAA TAAGCCCGAA ATAGAAGTCA CCTGGGCAAA GCAAGGTAGG    5100

ACTGAAAGGC TGTGCTCTCA AAACCCACCA GTCTTGAAAC GCCATCAACG GAAATAACT     5160

CGTACTACTC TTCAGTCAGA TCAAGAGGAA ATTGACTATG ATGATACCAT ATCAGTTGAA    5220

ATGAAGAAGG AAGATTTTGA CATTTATGAT GAGGATGAAA ATCAGAGCCC CCGCAGCTTT    5280

CAAAAGAAAA CACGACACTA TTTTATTGCT GCAGTGGAGA GGCTCTGGGA TTATGGGATG    5340

AGTAGCTCCC CACATGTTCT AAGAAACAGG GCTCAGAGTG GCAGTGTCCC TCAGTTCAAG    5400

AAAGTTGTTT TCCAGGAATT TACTGATGGC TCCTTTACTC AGCCCTTATA CCGTGGAGAA    5460

CTAAATGAAC ATTTGGGACT CCTGGGGCCA TATATAAGAG CAGAAGTTGA AGATAATATC    5520

ATGGTAACTT TCAGAAATCA GGCCTCTCGT CCCTATTCCT TCTATTCTAG CCTTATTTCT    5580

TATGAGGAAG ATCAGAGGCA AGGAGCAGAA CCTAGAAAAA ACTTTGTCAA GCCTAATGAA    5640

ACCAAAACTT ACTTTTGGAA AGTGCAACAT CATATGGCAC CCACTAAAGA TGAGTTTGAC    5700

TGCAAAGCCT GGGCTTATTT CTCTGATGTT GACCTGGAAA AAGATGTGCA CTCAGGCCTG   5760

ATTGGACCCC TTCTGGTCTG CCACACTAAC ACACTGAACC CTGCTCATGG GAGACAAGTG    5820

ACAGTACAGG AATTTGCTCT GTTTTTCACC ATCTTTGATG AGACCAAAAG CTGGTACTTC    5880
```

```
ACTGAAAATA  TGGAAAGAAA  CTGCAGGGCT  CCCTGCAATA  TCCAGATGGA  AGATCCCACT    5940
TTTAAAGAGA  ATTATCGCTT  CCATGCAATC  AATGGCTACA  TAATGGATAC  ACTACCTGGC    6000
TTAGTAATGG  CTCAGGATCA  AAGGATTCGA  TGGTATCTGC  TCAGCATGGG  CAGCAATGAA    6060
AACATCCATT  CTATTCATTT  CAGTGGACAT  GTGTTCACTG  TACGAAAAAA  AGAGGAGTAT    6120
AAAATGGCAC  TGTACAATCT  CTATCCAGGT  GTTTTGAGA   CAGTGGAAAT  GTTACCATCC    6180
AAAGCTGGAA  TTTGGCGGGT  GGAATGCCTT  ATTGGCGAGC  ATCTACATGC  TGGGATGAGC    6240
ACACTTTTTC  TGGTGTACAG  CAATAAGTGT  CAGACTCCCC  TGGGAATGGC  TTCTGGACAC    6300
ATTAGAGATT  TTCAGATTAC  AGCTTCAGGA  CAATATGGAC  AGTGGGCCCC  AAAGCTGGCC    6360
AGACTTCATT  ATTCCGGATC  AATCAATGCC  TGGAGCACCA  AGGAGCCCTT  TTCTTGGATC    6420
AAGGTGGATC  TGTTGGCACC  AATGATTATT  CACGGCATCA  AGACCCAGGG  TGCCCGTCAG    6480
AAGTTCTCCA  GCCTCTACAT  CTCTCAGTTT  ATCATCATGT  ATAGTCTTGA  TGGGAAGAAG    6540
TGGCAGACTT  ATCGAGGAAA  TTCCACTGGA  ACCTTAATGG  TCTTCTTTGG  CAATGTGGAT    6600
TCATCTGGGA  TAAAACACAA  TATTTTTAAC  CCTCCAATTA  TTGCTCGATA  CATCCGTTTG    6660
CACCCAACTC  ATTATAGCAT  TCGCAGCACT  CTTCGCATGG  AGTTGATGGG  CTGTGATTTA    6720
AATAGTTGCA  GCATGCCATT  GGGAATGGAG  AGTAAAGCAA  TATCAGATGC  ACAGATTACT    6780
GCTTCATCCT  ACTTTACCAA  TATGTTTGCC  ACCTGGTCTC  CTTCAAAAGC  TCGACTTCAC    6840
CTCCAAGGGA  GGAGTAATGC  CTGGAGACCT  CAGGTGAATA  ATCCAAAAGA  GTGGCTGCAA    6900
GTGGACTTCC  AGAAGACAAT  GAAAGTCACA  GGAGTAACTA  CTCAGGGAGT  AAAATCTCTG    6960
CTTACCAGCA  TGTATGTGAA  GGAGTTCCTC  ATCTCCAGCA  GTCAAGATGG  CCATCAGTGG    7020
ACTCTCTTTT  TTCAGAATGG  CAAAGTAAAG  GTTTTTCAGG  GAAATCAAGA  CTCCTTCACA    7080
CCTGTGGTGA  ACTCTCTAGA  CCCACCGTTA  CTGACTCGCT  ACCTTCGAAT  TCACCCCCAG    7140
AGTTGGGTGC  ACCAGATTGC  CCTGAGGATG  GAGGTTCTGG  GCTGCGAGGC  ACAGGACCTC    7200
TACTGAGGGT  GGCCACTGCA  GCACCTGCCA  CTGCCGTCAC  CTCTCCCTCC  TCAGCTCCAG    7260
GGCAGTGTCC  CTCCCTGGCT  TGCCTTCTAC  CTTTGTGCTA  AATCCTAGCA  GACACTGCCT    7320
TGAAGCCTCC  TGAATTAACT  ATCATCAGTC  CTGCATTTCT  TTGGTGGGGG  GCCAGGAGGG    7380
TGCATCCAAT  TTAACTTAAC  TCTTACCTAT  TTTCTGCAGC  TGCTCCCAGA  TTACTCCTTC    7440
CTTCCAATAT  AACTAGGCAA  AAAGAAGTGA  GGAGAAACCT  GCATGAAAGC  ATTCTTCCCT    7500
GAAAAGTTAG  GCCTCTCAGA  GTCACCACTT  CCTCTGTTGT  AGAAAAACTA  TGTGATGAAA    7560
CTTTGAAAAA  GATATTTATG  ATGTTAACAT  TTCAGGTTAA  GCCTCATACG  TTTAAAATAA    7620
AACTCTCAGT  TGTTTATTAT  CCTGATCAAG  CATGGAACAA  AGCATGTTTC  AGGATCAGAT    7680
CAATACAATC  TTGGAGTCAA  AAGGCAAATC  ATTTGGACAA  TCTGCAAAAT  GGAGAGAATA    7740
CAATAACTAC  TACAGTAAAG  TCTGTTTCTG  CTTCCTTACA  CATAGATATA  ATTATGTTAT    7800
TTAGTCATTA  TGAGGGGCAC  ATTCTTATCT  CCAAAACTAG  CATTCTTAAA  CTGAGAATTA    7860
TAGATGGGGT  TCAAGAATCC  CTAAGTCCCC  TGAAATTATA  TAAGGCATTC  TGTATAAATG    7920
CAAATGTGCA  TTTTTCTGAC  GAGTGTCCAT  AGATATAAAG  CCATTGGTCT  TAATTCTGAC    7980
CAATAAAAAA  ATAAGTCAGG  AGGATGCAAT  TGTTGAAAGC  TTTGAAATAA  AATAACATGT    8040
CTTCTTGAAA  TTTGTGATGG  CCAAGAAAGA  AAATGATGAT  GACATTAGGC  TTCTAAAGGA    8100
CATACATTTA  ATATTTCTGT  GGAAATATGA  GGAAAATCCA  TGGTTATCTG  AGATAGGAGA    8160
TACAAACTTT  GTAATTCTAA  TAATGCACTC  AGTTTACTCT  CTCCCTCTAC  TAATTTCCTG    8220
CTGAAAATAA  CACAACAAAA  ATGTAACAGG  GGAAATTATA  TACCGTGACT  GAAAACTAGA    8280
```

```
GTCCTACTTA  CATAGTTGAA  ATATCAAGGA  GGTCAGAAGA  AAATTGGACT  GGTGAAAACA    8340

GAAAAAACAC  TCCAGTCTGC  CATATCACCA  CACAATAGGA  TCCCCCTTCT  TGCCCTCCAC    8400

CCCCATAAGA  TTGTGAAGGG  TTTACTGCTC  CTTCCATCTG  CCTGCACCCC  TTCACTATGA    8460

CTACACAGAA  CTCTCCTGAT  AGTAAAGGGG  GCTGGAGGCA  AGGATAAGTT  ATAGAGCAGT    8520

TGGAGGAAGC  ATCCAAAGAC  TGCAACCCAG  GGCAAATGGA  AAACAGGAGA  TCCTAATATG    8580

AAAGAAAAAT  GGATCCCAAT  CTGAGAAAAG  GCAAAAGAAT  GGCTACTTTT  TTCTATGCTG    8640

GAGTATTTTC  TAATAATCCT  GCTTGACCCT  TATCTGACCT  CTTTGGAAAC  TATAACATAG    8700

CTGTCACAGT  ATAGTCACAA  TCCACAAATG  ATGCAGGTGC  AAATGGTTTA  TAGCCCTGTG    8760

AAGTTCTTAA  AGTTTAGAGG  CTAACTTACA  GAAATGAATA  AGTTGTTTTG  TTTTATAGCC    8820

CGGTAGAGGA  GTTAACCCCA  AAGGTGATAT  GGTTTTATTT  CCTGTTATGT  TTAACTTGAT    8880

AATCTTATTT  TGGCATTCTT  TTCCCATTGA  CTATATACAT  CTCTATTTCT  CAAATGTTCA    8940

TGGAACTAGC  TCTTTTATTT  TCCTGCTGGT  TTCTTCAGTA  ATGAGTTAAA  TAAAACATTG    9000

ACACATACA                                                                 9009
```

( 2 ) INFORMATION FOR SEQ ID NO:2:

( i ) SEQUENCE CHARACTERISTICS:
        ( A ) LENGTH: 2332 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v ) FRAGMENT TYPE: N-terminal ( v i ) ORIGINAL SOURCE:
        ( A ) ORGANISM: Homo sapien
        ( F ) TISSUE TYPE: Liver cDNA sequence ( x i ) SEQUENCE DESCRIPTION: SEQ ID NO:2:

```
Ala  Thr  Arg  Arg  Tyr  Tyr  Leu  Gly  Ala  Val  Glu  Leu  Ser  Trp  Asp  Tyr
1                  5                        10                       15

Met  Gln  Ser  Asp  Leu  Gly  Glu  Leu  Pro  Val  Asp  Ala  Arg  Phe  Pro  Pro
                20                       25                       30

Arg  Val  Pro  Lys  Ser  Phe  Pro  Phe  Asn  Thr  Ser  Val  Val  Tyr  Lys  Lys
           35                       40                       45

Thr  Leu  Phe  Val  Glu  Phe  Thr  Val  His  Leu  Phe  Asn  Ile  Ala  Lys  Pro
      50                       55                       60

Arg  Pro  Pro  Trp  Met  Gly  Leu  Leu  Gly  Pro  Thr  Ile  Gln  Ala  Glu  Val
65                       70                       75                       80

Tyr  Asp  Thr  Val  Val  Ile  Thr  Leu  Lys  Asn  Met  Ala  Ser  His  Pro  Val
                     85                       90                       95

Ser  Leu  His  Ala  Val  Gly  Val  Ser  Tyr  Trp  Lys  Ala  Ser  Glu  Gly  Ala
                100                      105                      110

Glu  Tyr  Asp  Asp  Gln  Thr  Ser  Gln  Arg  Glu  Lys  Glu  Asp  Asp  Lys  Val
           115                      120                      125

Phe  Pro  Gly  Gly  Ser  His  Thr  Tyr  Val  Trp  Gln  Val  Leu  Lys  Glu  Asn
      130                      135                      140

Gly  Pro  Met  Ala  Ser  Asp  Pro  Leu  Cys  Leu  Thr  Tyr  Ser  Tyr  Leu  Ser
145                      150                      155                      160
```

```
His  Val  Asp  Leu  Val  Lys  Asp  Leu  Asn  Ser  Gly  Leu  Ile  Gly  Ala  Leu
               165                 170                      175

Leu  Val  Cys  Arg  Glu  Gly  Ser  Leu  Ala  Lys  Glu  Lys  Thr  Gln  Thr  Leu
               180                 185                      190

His  Lys  Phe  Ile  Leu  Leu  Phe  Ala  Val  Phe  Asp  Glu  Gly  Lys  Ser  Trp
               195                 200                      205

His  Ser  Glu  Thr  Lys  Asn  Ser  Leu  Met  Gln  Asp  Arg  Asp  Ala  Ala  Ser
     210                      215                      220

Ala  Arg  Ala  Trp  Pro  Lys  Met  His  Thr  Val  Asn  Gly  Tyr  Val  Asn  Arg
225                      230                 235                           240

Ser  Leu  Pro  Gly  Leu  Ile  Gly  Cys  His  Arg  Lys  Ser  Val  Tyr  Trp  His
               245                      250                           255

Val  Ile  Gly  Met  Gly  Thr  Thr  Pro  Glu  Val  His  Ser  Ile  Phe  Leu  Glu
               260                 265                      270

Gly  His  Thr  Phe  Leu  Val  Arg  Asn  His  Arg  Gln  Ala  Ser  Leu  Glu  Ile
          275                      280                 285

Ser  Pro  Ile  Thr  Phe  Leu  Thr  Ala  Gln  Thr  Leu  Leu  Met  Asp  Leu  Gly
     290                      295                      300

Gln  Phe  Leu  Leu  Phe  Cys  His  Ile  Ser  Ser  His  Gln  His  Asp  Gly  Met
305                      310                 315                           320

Glu  Ala  Tyr  Val  Lys  Val  Asp  Ser  Cys  Pro  Glu  Glu  Pro  Gln  Leu  Arg
               325                 330                      335

Met  Lys  Asn  Asn  Glu  Glu  Ala  Glu  Asp  Tyr  Asp  Asp  Asp  Leu  Thr  Asp
               340                 345                      350

Ser  Glu  Met  Asp  Val  Val  Arg  Phe  Asp  Asp  Asp  Asn  Ser  Pro  Ser  Phe
          355                      360                      365

Ile  Gln  Ile  Arg  Ser  Val  Ala  Lys  Lys  His  Pro  Lys  Thr  Trp  Val  His
     370                      375                      380

Tyr  Ile  Ala  Ala  Glu  Glu  Glu  Asp  Trp  Asp  Tyr  Ala  Pro  Leu  Val  Leu
385                      390                 395                           400

Ala  Pro  Asp  Asp  Arg  Ser  Tyr  Lys  Ser  Gln  Tyr  Leu  Asn  Asn  Gly  Pro
               405                 410                      415

Gln  Arg  Ile  Gly  Arg  Lys  Tyr  Lys  Lys  Val  Arg  Phe  Met  Ala  Tyr  Thr
               420                 425                      430

Asp  Glu  Thr  Phe  Lys  Thr  Arg  Glu  Ala  Ile  Gln  His  Glu  Ser  Gly  Ile
          435                      440                 445

Leu  Gly  Pro  Leu  Leu  Tyr  Gly  Glu  Val  Gly  Asp  Thr  Leu  Leu  Ile  Ile
     450                      455                 460

Phe  Lys  Asn  Gln  Ala  Ser  Arg  Pro  Tyr  Asn  Ile  Tyr  Pro  His  Gly  Ile
465                      470                 475                           480

Thr  Asp  Val  Arg  Pro  Leu  Tyr  Ser  Arg  Arg  Leu  Pro  Lys  Gly  Val  Lys
               485                 490                      495

His  Leu  Lys  Asp  Phe  Pro  Ile  Leu  Pro  Gly  Glu  Ile  Phe  Lys  Tyr  Lys
               500                 505                      510

Trp  Thr  Val  Thr  Val  Glu  Asp  Gly  Pro  Thr  Lys  Ser  Asp  Pro  Arg  Cys
          515                      520                 525

Leu  Thr  Arg  Tyr  Tyr  Ser  Ser  Phe  Val  Asn  Met  Glu  Arg  Asp  Leu  Ala
     530                      535                 540

Ser  Gly  Leu  Ile  Gly  Pro  Leu  Leu  Ile  Cys  Tyr  Lys  Glu  Ser  Val  Asp
545                      550                 555                           560

Gln  Arg  Gly  Asn  Gln  Ile  Met  Ser  Asp  Lys  Arg  Asn  Val  Ile  Leu  Phe
               565                 570                      575

Ser  Val  Phe  Asp  Glu  Asn  Arg  Ser  Trp  Tyr  Leu  Thr  Glu  Asn  Ile  Gln
               580                 585                      590
```

-continued

```
Arg  Phe  Leu  Pro  Asn  Pro  Ala  Gly  Val  Gln  Leu  Glu  Asp  Pro  Glu  Phe
          595                 600                 605

Gln  Ala  Ser  Asn  Ile  Met  His  Ser  Ile  Asn  Gly  Tyr  Val  Phe  Asp  Ser
     610                 615                 620

Leu  Gln  Leu  Ser  Val  Cys  Leu  His  Glu  Val  Ala  Tyr  Trp  Tyr  Ile  Leu
625                 630                 635                          640

Ser  Ile  Gly  Ala  Gln  Thr  Asp  Phe  Leu  Ser  Val  Phe  Phe  Ser  Gly  Tyr
                    645                 650                          655

Thr  Phe  Lys  His  Lys  Met  Val  Tyr  Glu  Asp  Thr  Leu  Thr  Leu  Phe  Pro
               660                 665                 670

Phe  Ser  Gly  Glu  Thr  Val  Phe  Met  Ser  Met  Glu  Asn  Pro  Gly  Leu  Trp
          675                 680                 685

Ile  Leu  Gly  Cys  His  Asn  Ser  Asp  Phe  Arg  Asn  Arg  Gly  Met  Thr  Ala
     690                 695                 700

Leu  Leu  Lys  Val  Ser  Ser  Cys  Asp  Lys  Asn  Thr  Gly  Asp  Tyr  Tyr  Glu
705                 710                 715                          720

Asp  Ser  Tyr  Glu  Asp  Ile  Ser  Ala  Tyr  Leu  Leu  Ser  Lys  Asn  Asn  Ala
                    725                 730                 735

Ile  Glu  Pro  Arg  Ser  Phe  Ser  Gln  Asn  Ser  Arg  His  Pro  Ser  Thr  Arg
               740                 745                 750

Gln  Lys  Gln  Phe  Asn  Ala  Thr  Thr  Ile  Pro  Glu  Asn  Asp  Ile  Glu  Lys
          755                 760                 765

Thr  Asp  Pro  Trp  Phe  Ala  His  Arg  Thr  Pro  Met  Pro  Lys  Ile  Gln  Asn
     770                 775                 780

Val  Ser  Ser  Ser  Asp  Leu  Leu  Met  Leu  Leu  Arg  Gln  Ser  Pro  Thr  Pro
785                 790                 795                          800

His  Gly  Leu  Ser  Leu  Ser  Asp  Leu  Gln  Glu  Ala  Lys  Tyr  Glu  Thr  Phe
                    805                 810                 815

Ser  Asp  Asp  Pro  Ser  Pro  Gly  Ala  Ile  Asp  Ser  Asn  Asn  Ser  Leu  Ser
               820                 825                 830

Glu  Met  Thr  His  Phe  Arg  Pro  Gln  Leu  His  His  Ser  Gly  Asp  Met  Val
          835                 840                 845

Phe  Thr  Pro  Glu  Ser  Gly  Leu  Gln  Leu  Arg  Leu  Asn  Glu  Lys  Leu  Gly
     850                 855                 860

Thr  Thr  Ala  Ala  Thr  Glu  Leu  Lys  Lys  Leu  Asp  Phe  Lys  Val  Ser  Ser
865                 870                 875                          880

Thr  Ser  Asn  Asn  Leu  Ile  Ser  Thr  Ile  Pro  Ser  Asp  Asn  Leu  Ala  Ala
                    885                 890                 895

Gly  Thr  Asp  Asn  Thr  Ser  Ser  Leu  Gly  Pro  Pro  Ser  Met  Pro  Val  His
               900                 905                 910

Tyr  Asp  Ser  Gln  Leu  Asp  Thr  Thr  Leu  Phe  Gly  Lys  Lys  Ser  Ser  Pro
          915                 920                 925

Leu  Thr  Glu  Ser  Gly  Gly  Pro  Leu  Ser  Leu  Ser  Glu  Glu  Asn  Asn  Asp
     930                 935                 940

Ser  Lys  Leu  Leu  Glu  Ser  Gly  Leu  Met  Asn  Ser  Gln  Glu  Ser  Ser  Trp
945                 950                 955                          960

Gly  Lys  Asn  Val  Ser  Ser  Thr  Glu  Ser  Gly  Arg  Leu  Phe  Lys  Gly  Lys
                    965                 970                          975

Arg  Ala  His  Gly  Pro  Ala  Leu  Leu  Thr  Lys  Asp  Asn  Ala  Leu  Phe  Lys
               980                 985                 990

Val  Ser  Ile  Ser  Leu  Leu  Lys  Thr  Asn  Lys  Thr  Ser  Asn  Asn  Ser  Ala
          995                1000                1005

Thr  Asn  Arg  Lys  Thr  His  Ile  Asp  Gly  Pro  Ser  Leu  Leu  Ile  Glu  Asn
```

```
                    1010                    1015                    1020
    Ser  Pro  Ser  Val  Trp  Gln  Asn  Ile  Leu  Glu  Ser  Asp  Thr  Glu  Phe  Lys
    1025                    1030                    1035                    1040

Lys  Val  Thr  Pro  Leu  Ile  His  Asp  Arg  Met  Leu  Met  Asp  Lys  Asn  Ala
                    1045                    1050                    1055

Thr  Ala  Leu  Arg  Leu  Asn  His  Met  Ser  Asn  Lys  Thr  Thr  Ser  Ser  Lys
                    1060                    1065                    1070

Asn  Met  Glu  Met  Val  Gln  Gln  Lys  Lys  Glu  Gly  Pro  Ile  Pro  Pro  Asp
                    1075                    1080                    1085

Ala  Gln  Asn  Pro  Asp  Met  Ser  Phe  Phe  Lys  Met  Leu  Phe  Leu  Pro  Glu
                    1090                    1095                    1100

Ser  Ala  Arg  Trp  Ile  Gln  Arg  Thr  His  Gly  Lys  Asn  Ser  Leu  Asn  Ser
    1105                    1110                    1115                    1120

Gly  Gln  Gly  Pro  Ser  Pro  Lys  Gln  Leu  Val  Ser  Leu  Gly  Pro  Glu  Lys
                    1125                    1130                    1135

Ser  Val  Glu  Gly  Gln  Asn  Phe  Leu  Ser  Glu  Lys  Asn  Lys  Val  Val  Val
                    1140                    1145                    1150

Gly  Lys  Gly  Glu  Phe  Thr  Lys  Asp  Val  Gly  Leu  Lys  Glu  Met  Val  Phe
                    1155                    1160                    1165

Pro  Ser  Ser  Arg  Asn  Leu  Phe  Leu  Thr  Asn  Leu  Asp  Asn  Leu  His  Glu
                    1170                    1175                    1180

Asn  Asn  Thr  His  Asn  Gln  Glu  Lys  Lys  Ile  Gln  Glu  Glu  Ile  Glu  Lys
    1185                    1190                    1195                    1200

Lys  Glu  Thr  Leu  Ile  Gln  Glu  Asn  Val  Val  Leu  Pro  Gln  Ile  His  Thr
                    1205                    1210                    1215

Val  Thr  Gly  Thr  Lys  Asn  Phe  Met  Lys  Asn  Leu  Phe  Leu  Leu  Ser  Thr
                    1220                    1225                    1230

Arg  Gln  Asn  Val  Glu  Gly  Ser  Tyr  Glu  Gly  Ala  Tyr  Ala  Pro  Val  Leu
                    1235                    1240                    1245

Gln  Asp  Phe  Arg  Ser  Leu  Asn  Asp  Ser  Thr  Asn  Arg  Thr  Lys  Lys  His
                    1250                    1255                    1260

Thr  Ala  His  Phe  Ser  Lys  Lys  Gly  Glu  Glu  Glu  Asn  Leu  Glu  Gly  Leu
    1265                    1270                    1275                    1280

Gly  Asn  Gln  Thr  Lys  Gln  Ile  Val  Glu  Lys  Tyr  Ala  Cys  Thr  Thr  Arg
                    1285                    1290                    1295

Ile  Ser  Pro  Asn  Thr  Ser  Gln  Gln  Asn  Phe  Val  Thr  Gln  Arg  Ser  Lys
                    1300                    1305                    1310

Arg  Ala  Leu  Lys  Gln  Phe  Arg  Leu  Pro  Leu  Glu  Glu  Thr  Glu  Leu  Glu
                    1315                    1320                    1325

Lys  Arg  Ile  Ile  Val  Asp  Asp  Thr  Ser  Thr  Gln  Trp  Ser  Lys  Asn  Met
                    1330                    1335                    1340

Lys  His  Leu  Thr  Pro  Ser  Thr  Leu  Thr  Gln  Ile  Asp  Tyr  Asn  Glu  Lys
1345                    1350                    1355                    1360

Glu  Lys  Gly  Ala  Ile  Thr  Gln  Ser  Pro  Leu  Ser  Asp  Cys  Leu  Thr  Arg
                    1365                    1370                    1375

Ser  His  Ser  Ile  Pro  Gln  Ala  Asn  Arg  Ser  Pro  Leu  Pro  Ile  Ala  Lys
                    1380                    1385                    1390

Val  Ser  Ser  Phe  Pro  Ser  Ile  Arg  Pro  Ile  Tyr  Leu  Thr  Arg  Val  Leu
                    1395                    1400                    1405

Phe  Gln  Asp  Asn  Ser  Ser  His  Leu  Pro  Ala  Ala  Ser  Tyr  Arg  Lys  Lys
                    1410                    1415                    1420

Asp  Ser  Gly  Val  Gln  Glu  Ser  Ser  His  Phe  Leu  Gln  Gly  Ala  Lys  Lys
    1425                    1430                    1435                    1440
```

```
Asn Asn Leu Ser Leu Ala Ile Leu Thr Leu Glu Met Thr Gly Asp Gln
            1445                1450                1455
Arg Glu Val Gly Ser Leu Gly Thr Ser Ala Thr Asn Ser Val Thr Tyr
            1460                1465                1470
Lys Lys Val Glu Asn Thr Val Leu Pro Lys Pro Asp Leu Pro Lys Thr
            1475                1480                1485
Ser Gly Lys Val Glu Leu Leu Pro Lys Val His Ile Tyr Gln Lys Asp
            1490                1495                1500
Leu Phe Pro Thr Glu Thr Ser Asn Gly Ser Pro Gly His Leu Asp Leu
1505                1510                1515                1520
Val Glu Gly Ser Leu Leu Gln Gly Thr Glu Gly Ala Ile Lys Trp Asn
            1525                1530                1535
Glu Ala Asn Arg Pro Gly Lys Val Pro Phe Leu Arg Val Ala Thr Glu
            1540                1545                1550
Ser Ser Ala Lys Thr Pro Ser Lys Leu Leu Asp Pro Leu Ala Trp Asp
            1555                1560                1565
Asn His Tyr Gly Thr Gln Ile Pro Lys Glu Glu Trp Lys Ser Gln Glu
            1570                1575                1580
Lys Ser Pro Glu Lys Thr Ala Phe Lys Lys Lys Asp Thr Ile Leu Ser
1585                1590                1595                1600
Leu Asn Ala Cys Glu Ser Asn His Ala Ile Ala Ala Ile Asn Glu Gly
            1605                1610                1615
Gln Asn Lys Pro Glu Ile Glu Val Thr Trp Ala Lys Gln Gly Arg Thr
            1620                1625                1630
Glu Arg Leu Cys Ser Gln Asn Pro Pro Val Leu Lys Arg His Gln Arg
            1635                1640                1645
Glu Ile Thr Arg Thr Thr Leu Gln Ser Asp Gln Glu Glu Ile Asp Tyr
            1650                1655                1660
Asp Asp Thr Ile Ser Val Glu Met Lys Lys Glu Asp Phe Asp Ile Tyr
1665                1670                1675                1680
Asp Glu Asp Glu Asn Gln Ser Pro Arg Ser Phe Gln Lys Lys Thr Arg
            1685                1690                1695
His Tyr Phe Ile Ala Ala Val Glu Arg Leu Trp Asp Tyr Gly Met Ser
            1700                1705                1710
Ser Ser Pro His Val Leu Arg Asn Arg Ala Gln Ser Gly Ser Val Pro
            1715                1720                1725
Gln Phe Lys Lys Val Val Phe Gln Glu Phe Thr Asp Gly Ser Phe Thr
            1730                1735                1740
Gln Pro Leu Tyr Arg Gly Glu Leu Asn Glu His Leu Gly Leu Leu Gly
1745                1750                1755                1760
Pro Tyr Ile Arg Ala Glu Val Glu Asp Asn Ile Met Val Thr Phe Arg
            1765                1770                1775
Asn Gln Ala Ser Arg Pro Tyr Ser Phe Tyr Ser Ser Leu Ile Ser Tyr
            1780                1785                1790
Glu Glu Asp Gln Arg Gln Gly Ala Glu Pro Arg Lys Asn Phe Val Lys
            1795                1800                1805
Pro Asn Glu Thr Lys Thr Tyr Phe Trp Lys Val Gln His His Met Ala
            1810                1815                1820
Pro Thr Lys Asp Glu Phe Asp Cys Lys Ala Trp Ala Tyr Phe Ser Asp
1825                1830                1835                1840
Val Asp Leu Glu Lys Asp Val His Ser Gly Leu Ile Gly Pro Leu Leu
            1845                1850                1855
Val Cys His Thr Asn Thr Leu Asn Pro Ala His Gly Arg Gln Val Thr
            1860                1865                1870
```

Val Gln Glu Phe Ala Leu Phe Phe Thr Ile Phe Asp Glu Thr Lys Ser
            1875                1880                1885

Trp Tyr Phe Thr Glu Asn Met Glu Arg Asn Cys Arg Ala Pro Cys Asn
            1890                1895                1900

Ile Gln Met Glu Asp Pro Thr Phe Lys Glu Asn Tyr Arg Phe His Ala
1905                1910                1915                1920

Ile Asn Gly Tyr Ile Met Asp Thr Leu Pro Gly Leu Val Met Ala Gln
            1925                1930                1935

Asp Gln Arg Ile Arg Trp Tyr Leu Leu Ser Met Gly Ser Asn Glu Asn
            1940                1945                1950

Ile His Ser Ile His Phe Ser Gly His Val Phe Thr Val Arg Lys Lys
            1955                1960                1965

Glu Glu Tyr Lys Met Ala Leu Tyr Asn Leu Tyr Pro Gly Val Phe Glu
            1970                1975                1980

Thr Val Glu Met Leu Pro Ser Lys Ala Gly Ile Trp Arg Val Glu Cys
1985                1990                1995                2000

Leu Ile Gly Glu His Leu His Ala Gly Met Ser Thr Leu Phe Leu Val
            2005                2010                2015

Tyr Ser Asn Lys Cys Gln Thr Pro Leu Gly Met Ala Ser Gly His Ile
            2020                2025                2030

Arg Asp Phe Gln Ile Thr Ala Ser Gly Gln Tyr Gly Gln Trp Ala Pro
            2035                2040                2045

Lys Leu Ala Arg Leu His Tyr Ser Gly Ser Ile Asn Ala Trp Ser Thr
            2050                2055                2060

Lys Glu Pro Phe Ser Trp Ile Lys Val Asp Leu Leu Ala Pro Met Ile
2065                2070                2075                2080

Ile His Gly Ile Lys Thr Gln Gly Ala Arg Gln Lys Phe Ser Ser Leu
            2085                2090                2095

Tyr Ile Ser Gln Phe Ile Ile Met Tyr Ser Leu Asp Gly Lys Lys Trp
            2100                2105                2110

Gln Thr Tyr Arg Gly Asn Ser Thr Gly Thr Leu Met Val Phe Phe Gly
            2115                2120                2125

Asn Val Asp Ser Ser Gly Ile Lys His Asn Ile Phe Asn Pro Pro Ile
            2130                2135                2140

Ile Ala Arg Tyr Ile Arg Leu His Pro Thr His Tyr Ser Ile Arg Ser
2145                2150                2155                2160

Thr Leu Arg Met Glu Leu Met Gly Cys Asp Leu Asn Ser Cys Ser Met
            2165                2170                2175

Pro Leu Gly Met Glu Ser Lys Ala Ile Ser Asp Ala Gln Ile Thr Ala
            2180                2185                2190

Ser Ser Tyr Phe Thr Asn Met Phe Ala Thr Trp Ser Pro Ser Lys Ala
            2195                2200                2205

Arg Leu His Leu Gln Gly Arg Ser Asn Ala Trp Arg Pro Gln Val Asn
            2210                2215                2220

Asn Pro Lys Glu Trp Leu Gln Val Asp Phe Gln Lys Thr Met Lys Val
2225                2230                2235                2240

Thr Gly Val Thr Thr Gln Gly Val Lys Ser Leu Leu Thr Ser Met Tyr
            2245                2250                2255

Val Lys Glu Phe Leu Ile Ser Ser Ser Gln Asp Gly His Gln Trp Thr
            2260                2265                2270

Leu Phe Phe Gln Asn Gly Lys Val Lys Val Phe Gln Gly Asn Gln Asp
            2275                2280                2285

Ser Phe Thr Pro Val Val Asn Ser Leu Asp Pro Pro Leu Leu Thr Arg

|   | 2290 |   |   |   | 2295 |   |   |   | 2300 |   |   |   |   |
|---|---|---|---|---|---|---|---|---|---|---|---|---|---|
| Tyr | Leu | Arg | Ile | His | Pro | Gln | Ser | Trp | Val | His | Gln | Ile | Ala | Leu | Arg |
| 2305 |   |   |   |   | 2310 |   |   |   | 2315 |   |   |   |   | 2320 |
| Met | Glu | Val | Leu | Gly | Cys | Glu | Ala | Gln | Asp | Leu | Tyr |
|   |   |   |   | 2325 |   |   |   |   | 2330 |

( 2 ) INFORMATION FOR SEQ ID NO:3:

( i ) SEQUENCE CHARACTERISTICS:
        ( A ) LENGTH: 1130 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Porcine
        ( F ) TISSUE TYPE: Blood ( i x ) FEATURE:
        ( A ) NAME/KEY: Region
        ( B ) LOCATION: 1..1130
        ( D ) OTHER INFORMATION: /note= "cDNA encoding A2
            domain of porcine factor VIII."

( x i ) SEQUENCE DESCRIPTION: SEQ ID NO:3:

| TAAGCACCCT | AAGACGTGGG | TGCACTACAT | CTCTGCAGAG | GAGGAGGACT | GGGACTACGC | 60 |
| CCCCGCGGTC | CCCAGCCCCA | GTGACAGAAG | TTATAAAAGT | CTCTACTTGA | ACAGTGGTCC | 120 |
| TCAGCGAATT | GGTAGGAAAT | ACAAAAAAGC | TCGATTCGTC | GCTTACACGG | ATGTAACATT | 180 |
| TAAGACTCGT | AAAGCTATTC | CGTATGAATC | AGGAATCCTG | GGACCTTTAC | TTTATGGAGA | 240 |
| AGTTGGAGAC | ACACTTTTGA | TTATATTTAA | GAATAAAGCG | AGCCGACCAT | ATAACATCTA | 300 |
| CCCTCATGGA | ATCACTGATG | TCAGCGCTTT | GCACCCAGGG | AGACTTCTAA | AAGGTTGGAA | 360 |
| ACATTTGAAA | GACATGCCAA | TTCTGCCAGG | AGAGACTTTC | AAGTATAAAT | GGACAGTGAC | 420 |
| TGTGGAAGAT | GGGCCAACCA | AGTCCGATCC | TCGGTGCCTG | ACCCGCTACT | ACTCGAGCTC | 480 |
| CATTAATCTA | GAGAAAGATC | TGGCTTCGGG | ACTCATTGGC | CCTCTCCTCA | TCTGCTACAA | 540 |
| AGAATCTGTA | GACCAAAGAG | GAAACCAGAT | GATGTCAGAC | AAGAGAAACG | TCATCCTGTT | 600 |
| TTCTGTATTC | GATGAGAATC | AAAGCTGGTA | CCTCGCAGAG | AATATTCAGC | GCTTCCTCCC | 660 |
| CAATCCGGAT | GGATTACAGC | CCCAGGATCC | AGAGTTCCAA | GCTTCTAACA | TCATGCACAG | 720 |
| CATCAATGGC | TATGTTTTTG | ATAGCTTGCA | GCTGTCGGTT | TGTTTGCACG | AGGTGGCATA | 780 |
| CTGGTACATT | CTAAGTGTTG | GAGCACAGAC | GGACTTCCTC | TCCGTCTTCT | TCTCTGGCTA | 840 |
| CACCTTCAAA | CACAAAATGG | TCTATGAAGA | CACACTCACC | CTGTTCCCCT | TCTCAGGAGA | 900 |
| AACGGTCTTC | ATGTCAATGG | AAAACCCAGG | TCTCTGGGTC | CTAGGGTGCC | ACAACTCAGA | 960 |
| CTTGCGGAAC | AGAGGGATGA | CAGCCTTACT | GAAGGTGTAT | AGTTGTGACA | GGGACATTGG | 1020 |
| TGATTATTAT | GACAACACTT | ATGAAGATAT | TCCAGGCTTC | TTGCTGAGTG | GAAAGAATGT | 1080 |
| CATTGAACCC | AGAAGCTTTG | CCCAGAATTC | AAGACCCCT | AGTGCGAGCA |   | 1130 |

( 2 ) INFORMATION FOR SEQ ID NO:4:

( i ) SEQUENCE CHARACTERISTICS:
        ( A ) LENGTH: 368 amino acids
        ( B ) TYPE: amino acid
        ( C ) STRANDEDNESS: single (D) TOPOLOGY: linear (ii) MOLECULE TYPE: protein (iii) HYPOTHETICAL: YES (iv) ANTI-SENSE: NO (v) FRAGMENT TYPE: N-terminal (vi) ORIGINAL SOURCE:
 (A) ORGANISM: Porcine
 (F) TISSUE TYPE: Spleen (ix) FEATURE:
 (A) NAME/KEY: Protein
 (B) LOCATION: 1..368
 (D) OTHER INFORMATION: /note= "Predicted amino acid sequence of the porcine factor VIII A2 domain, defined as residues homologous to human factor VIII amino acid sequence 373-740. (Residues 1-4 are from known porcine amino acid sequence.)

(xi) SEQUENCE DESCRIPTION: SEQ ID NO:4:

```
Ser  Val  Ala  Lys  Lys  His  Pro  Lys  Thr  Trp  Val  His  Tyr  Ile  Ser  Ala
1               5                   10                  15

Glu  Glu  Glu  Asp  Trp  Asp  Tyr  Ala  Pro  Ala  Val  Pro  Ser  Pro  Ser  Asp
            20                  25                  30

Arg  Ser  Tyr  Lys  Ser  Leu  Tyr  Leu  Asn  Ser  Gly  Pro  Gln  Arg  Ile  Gly
        35                  40                  45

Arg  Lys  Tyr  Lys  Lys  Ala  Arg  Phe  Val  Ala  Tyr  Thr  Asp  Val  Thr  Phe
    50                  55                  60

Lys  Thr  Arg  Lys  Ala  Ile  Pro  Tyr  Glu  Ser  Gly  Ile  Leu  Gly  Pro  Leu
65                  70                  75                  80

Leu  Tyr  Gly  Glu  Val  Gly  Asp  Thr  Leu  Leu  Ile  Ile  Phe  Lys  Asn  Lys
            85                  90                  95

Ala  Ser  Arg  Pro  Tyr  Asn  Ile  Tyr  Pro  His  Gly  Ile  Thr  Asp  Val  Ser
            100                 105                 110

Ala  Leu  His  Pro  Gly  Arg  Leu  Leu  Lys  Gly  Trp  Lys  His  Leu  Lys  Asp
            115                 120                 125

Met  Pro  Ile  Leu  Pro  Gly  Glu  Thr  Phe  Lys  Tyr  Lys  Trp  Thr  Val  Thr
     130                 135                 140

Val  Glu  Asp  Gly  Pro  Thr  Lys  Ser  Asp  Pro  Arg  Cys  Leu  Thr  Arg  Tyr
145                 150                 155                 160

Tyr  Ser  Ser  Ser  Ile  Asn  Leu  Glu  Lys  Asp  Leu  Ala  Ser  Gly  Leu  Ile
                165                 170                 175

Gly  Pro  Leu  Leu  Ile  Cys  Tyr  Lys  Glu  Ser  Val  Asp  Gln  Arg  Gly  Asn
            180                 185                 190

Gln  Met  Met  Ser  Asp  Lys  Arg  Asn  Val  Ile  Leu  Phe  Ser  Val  Phe  Asp
     195                 200                 205

Glu  Asn  Gln  Ser  Trp  Tyr  Leu  Ala  Glu  Asn  Ile  Gln  Arg  Phe  Leu  Pro
     210                 215                 220

Asn  Pro  Asp  Gly  Leu  Gln  Pro  Gln  Asp  Pro  Glu  Phe  Gln  Ala  Ser  Asn
225                 230                 235                 240

Ile  Met  His  Ser  Ile  Asn  Gly  Tyr  Val  Phe  Asp  Ser  Leu  Gln  Leu  Ser
                245                 250                 255

Val  Cys  Leu  His  Glu  Val  Ala  Tyr  Trp  Tyr  Ile  Leu  Ser  Val  Gly  Ala
            260                 265                 270

Gln  Thr  Asp  Phe  Leu  Ser  Val  Phe  Phe  Ser  Gly  Tyr  Thr  Phe  Lys  His
            275                 280                 285

Lys  Met  Val  Tyr  Glu  Asp  Thr  Leu  Thr  Leu  Phe  Pro  Phe  Ser  Gly  Glu
```

|  |  |  | 290 |  |  |  | 295 |  |  |  | 300 |  |  |  |
|---|---|---|---|---|---|---|---|---|---|---|---|---|---|---|
| Thr | Val | Phe | Met | Ser | Met | Glu | Asn | Pro | Gly | Leu | Trp | Val | Leu | Gly | Cys |
| 305 |  |  |  |  | 310 |  |  |  |  | 315 |  |  |  |  | 320 |
| His | Asn | Ser | Asp | Leu | Arg | Asn | Arg | Gly | Met | Thr | Ala | Leu | Leu | Lys | Val |
|  |  |  |  | 325 |  |  |  |  | 330 |  |  |  |  | 335 |  |
| Tyr | Ser | Cys | Asp | Arg | Asp | Ile | Gly | Asp | Tyr | Tyr | Asp | Asn | Thr | Tyr | Glu |
|  |  |  | 340 |  |  |  |  | 345 |  |  |  |  | 350 |  |  |
| Asp | Ile | Pro | Gly | Phe | Leu | Leu | Ser | Gly | Lys | Asn | Val | Ile | Glu | Pro | Arg |
|  |  |  | 355 |  |  |  |  | 360 |  |  |  |  | 365 |  |  |

(2) INFORMATION FOR SEQ ID NO:5:

(i) SEQUENCE CHARACTERISTICS:
        (A) LENGTH: 7493 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Mus musculus (ix) FEATURE:
        (A) NAME/KEY: repeat_unit
        (B) LOCATION: 1..407
        (D) OTHER INFORMATION: /rpt_type="terminal"
            / note="5'UTR"

(ix) FEATURE:
        (A) NAME/KEY: misc_feature
        (B) LOCATION: 7471..7476
        (D) OTHER INFORMATION: /function="PolyA_signal"

(ix) FEATURE:
        (A) NAME/KEY: repeat_unit
        (B) LOCATION: 7368..7493
        (D) OTHER INFORMATION: /rpt_type="terminal"
            / note="3'UTR"

(ix) FEATURE:
        (A) NAME/KEY: misc_feature
        (B) LOCATION: 408..7367
        (D) OTHER INFORMATION: /product="Coagulation Factor VIII"

(x) PUBLICATION INFORMATION:
        (A) AUTHORS: Elder, F.
                Lakich, D.
                Gitschier, J.
        (B) TITLE: Sequence of the Murine Factor VIII cDNA.
        (C) JOURNAL: Genomics
        (D) VOLUME: 16
        (F) PAGES: 374-379
        (G) DATE: 1993
        (K) RELEVANT RESIDUES IN SEQ ID NO:5: FROM 1 TO 7476

(xi) SEQUENCE DESCRIPTION: SEQ ID NO:5:

```
TCTAGAGTTT    CTTTGCTACA    GGTACCAAGG    AACAGTCTTT    TAGAATAGGC    TAGGAATTTA         60

AATACACCTG    AACGCCCCTC    CTCAGTATTC    TGTTCCTTTT    CTTAAGGATT    CAAACTTGTT        120

AGGATGCACC    CAGCAGGAAA    TGGGTTAAGC    CTTAGCTCAG    CCACTCTTCC    TATTCCAGTT        180

TTCCTGTGCC    TGCTTCCTAC    TACCCAAAAG    GAAGTAATCC    TTCAGATCTG    TTTTGTGCTA        240

ATGCTACTTT    CACTCACAGT    AGATAAACTT    CCAGAAAATC    CTCTGCAAAA    TATTTAGGAC        300

TTTTTACTAA    ATCATTACAT    TTCTTTTTGT    TCTTAAAAGC    TAAAGTTATT    TTAGAGAAGA        360

GTTAAATTTT    CATTTCTTTA    GTTGAACATT    TTCTAGTAAT    AAAAGCCATG    CAAATAGCAC        420
```

| | | | | | |
|---|---|---|---|---|---|
| TCTTCGCTTG | CTTCTTTCTG | AGCCTTTTCA | ATTTCTGCTC | TAGTGCCATC | AGAAGATACT | 480
| ACCTTGGTGC | AGTGGAATTG | TCCTGGAACT | ATATTCAGAG | TGATCTGCTC | AGTGTGCTGC | 540
| ATACAGACTC | AAGATTTCTT | CCTAGAATGT | CAACATCTTT | TCCATTCAAC | ACCTCCATCA | 600
| TGTATAAAAA | GACTGTGTTT | GTAGAGTACA | AGGACCAGCT | TTTCAACATT | GCCAAGCCCA | 660
| GGCCACCCTG | GATGGGTTTG | CTAGGTCCTA | CCATTTGGAC | TGAGGTTCAT | GACACAGTGG | 720
| TCATTACACT | TAAAAACATG | GCTTCTCATC | CTGTCAGTCT | TCATGCTGTT | GGTGTGTCCT | 780
| ACTGGAAAGC | TTCTGAGGGA | GATGAATATG | AAGATCAGAC | AAGCCAAATG | GAGAAGGAAG | 840
| ATGATAAAGT | TTTCCCTGGT | GAAAGTCATA | CTTATGTTTG | GCAAGTCCTG | AAAGAGAATG | 900
| GTCCAATGGC | CTCTGACCCT | CCATGTCTCA | CTTACTCATA | TATGTCTCAT | GTGGATCTGG | 960
| TGAAAGATTT | GAATTCAGGC | CTCATTGGAG | CTCTGCTAGT | ATGTAAAGAA | GGCAGTCTCT | 1020
| CCAAAGAAAG | AACACAGATG | TTGTACCAAT | TTGTACTGCT | TTTTGCTGTA | TTTGATGAAG | 1080
| GGAAGAGCTG | GCACTCAGAA | ACAAACGACT | CTTATACACA | GTCTATGGAT | TCTGCATCTG | 1140
| CTAGAGACTG | GCCTAAAATG | CACACAGTCA | ATGGCTATGT | AAACAGGTCT | CTTCCAGGTC | 1200
| TGATTGGATG | CCATAGGAAA | TCAGTCTACT | GGCACGTGAT | TGGAATGGGC | ACCACTCCTG | 1260
| AAATACACTC | AATATTCCTC | GAAGGTCACA | CATTTTTGT | GAGGAACCAC | CGTCAAGCTT | 1320
| CATTGGAGAT | ATCACCAATA | ACTTTCCTTA | CTGCTCAAAC | ACTCTTGATA | GATCTTGGGC | 1380
| AGTTCCTACT | ATTTTGTCAT | ATCTCTTCCC | ATAAACATGA | TGGCATGGAA | GCTTATGTCA | 1440
| AAGTAGATAG | CTGCCCTGAG | GAATCCCAAT | GGCAAAAGAA | AATAATAAT | GAGGAAATGG | 1500
| AAGATTATGA | TGATGATCTT | TATTCAGAAA | TGGATATGTT | CACATTGGAT | TATGACAGCT | 1560
| CTCCTTTTAT | CCAAATTCGC | TCGGTTGCTA | AAAAGTACCC | TAAAACTTGG | ATACATTATA | 1620
| TTTCTGCTGA | GGAGGAAGAC | TGGGACTATG | CACCTTCAGT | TCCTACCTCG | GATAATGGAA | 1680
| GTTATAAAAG | CCAGTATCTG | AGCAATGGTC | CTCATCGGAT | TGGTAGGAAA | TATAAAAAAG | 1740
| TCAGATTTAT | AGCATACACA | GATGAAACCT | TTAAGACTCG | TGAAACTATT | CAGCATGAAT | 1800
| CAGGACTCTT | GGGACCTTTA | CTTTATGGAG | AAGTTGGAGA | CACACTGTTG | ATTATTTTA | 1860
| AGAATCAAGC | AAGCCGACCA | TATAACATTT | ACCCTCATGG | AATCACTGAT | GTCAGTCCTC | 1920
| TACATGCAAG | GAGATTGCCA | AGAGGTATAA | AGCACGTGAA | GGATTTGCCA | ATTCATCCAG | 1980
| GAGAGATATT | CAAGTACAAG | TGGACAGTTA | CAGTAGAAGA | TGGACCAACT | AAATCAGATC | 2040
| CACGGTGCCT | GACCCGCTAT | TATTCAAGTT | TCATTAACCC | TGAGAGAGAT | CTAGCTTCAG | 2100
| GACTGATTGG | CCCTCTTCTC | ATCTGCTACA | AGAATCTGT | AGATCAAAGG | GGAAACCAGA | 2160
| TGATGTCAGA | CAAAAGAAAT | GTCATCCTGT | TTTCTATATT | TGATGAGAAC | CAAAGCTGGT | 2220
| ACATCACAGA | GAACATGCAA | CGCTTCCTCC | CCAATGCAGC | TAAAACACAG | CCCCAGGACC | 2280
| CTGGGTTCCA | GGCCTCCAAC | ATCATGCACA | GCATCAATGG | CTATGTTTTT | GATAGCTTGG | 2340
| AGTTGACAGT | TTGTTTGCAT | GAGGTGGCAT | ACTGGCACAT | TCTCAGTGTT | GGAGCACAGA | 2400
| CAGACTTCTT | ATCTATCTTC | TTCTCTGGAT | ATACTTTCAA | ACACAAAATG | GTCTATGAAG | 2460
| ATACACTTAC | CCTGTTCCCA | TTCTCAGGAG | AAACTGTCTT | TATGTCGATG | GAAAACCCAG | 2520
| GTCTATGGGT | CTTGGGGTGT | CATAATTCAG | ACTTTCGGAA | GAGAGGTATG | ACAGCATTGC | 2580
| TGAAAGTTTC | TAGTTGTGAC | AAGAGCACTA | GTGATTATTA | TGAAGAAATA | TATGAAGATA | 2640
| TTCCAACACA | GTTGGTGAAT | GAGAACAATG | TCATTGATCC | CAGAAGCTTC | TTCCAGAATA | 2700
| CAAATCATCC | TAATACTAGG | AAAAAGAAAT | TCAAAGATTC | CACAATTCCA | AAAAATGATA | 2760
| TGGAGAAGAT | TGAGCCTCAG | TTTGAAGAGA | TAGCAGAGAT | GCTTAAAGTA | CAGAGTGTCT | 2820

```
CAGTTAGTGA  CATGTTGATG  CTCTTGGGAC  AGAGTCATCC  TACTCCACAT  GGCTTATTTT    2880

TATCAGATGG  CCAAGAAGCC  ATCTATGAGG  CTATTCATGA  TGATCATTCA  CCAAATGCAA    2940

TAGACAGCAA  TGAAGGCCCA  TCTAAAGTGA  CCCAACTCAG  GCCAGAATCC  CATCACAGTG    3000

AGAAATAGT   ATTTACTCCT  CAGCCCGGCC  TCCAGTTAAG  ATCCAATAAA  AGTTTGGAGA    3060

CAACTATAGA  AGTAAAGTGG  AAGAAACTTG  GTTTGCAAGT  TTCTAGTTTG  CCAAGTAATC    3120

TAATGACTAC  AACAATTCTG  TCAGACAATT  TGAAAGCAAC  TTTTGAAAAG  ACAGATTCTT    3180

CAGGATTTCC  AGATATGCCA  GTTCACTCTA  GTAGTAAATT  AAGTACTACT  GCATTTGGTA    3240

AGAAAGCATA  TTCCCTTGTT  GGGTCTCATG  TACCTTTAAA  CGCGAGTGAA  GAAAATAGTG    3300

ATTCCAACAT  ATTGGATTCA  ACTTTAATGT  ATAGTCAAGA  AAGTTTACCA  AGAGATAATA    3360

TATTATCAAT  AGAGAATGAT  AGATTACTCA  GAGAGAAGAG  GTTTCATGGA  ATTGCTTTAT    3420

TGACCAAAGA  TAATACTTTA  TTCAAAGACA  ATGTCTCCTT  AATGAAAACA  AACAAAACAT    3480

ATAATCATTC  AACAACTAAT  GAAAAACTAC  ACACTGAGAG  CCCAACATCA  ATTGAGAATA    3540

GTACAACAGA  CTTGCAAGAT  GCCATATTAA  AGGTCAATAG  TGAGATTCAA  GAAGTAACAG    3600

CTTTGATTCA  TGATGGAACA  CTTTTAGGCA  AAAATTCTAC  ATATTTGAGA  CTAAACCATA    3660

TGCTAAATAG  AACTACCTCA  ACAAAAAATA  AAGACATATT  TCATAGAAAA  GATGAAGATC    3720

CTATTCCACA  AGATGAAGAG  AATACAATCA  TGCCATTTTC  CAAGATGTTG  TTCTTGTCAG    3780

AATCTTCAAA  TTGGTTTAAA  AAGACCAATG  GAAATAATTC  CTTGAACTCT  GAGCAAGAAC    3840

ATAGTCCAAA  GCAATTAGTA  TATTTAATGT  TTAAAAAATA  TGTAAAAAAT  CAAAGTTTCT    3900

TGTCAGAGAA  AAATAAAGTC  ACAGTAGAAC  AGGATGGATT  TACAAAGAAC  ATAGGACTTA    3960

AAGACATGGC  TTTTCCACAT  AATATGAGCA  TATTTCTTAC  CACTTTGTCT  AACGTACATG    4020

AAAATGGTAG  GCACAATCAA  GAAAAAAATA  TTCAGGAAGA  GATAGAGAAG  GAAGCACTAA    4080

TTGAAGAGAA  AGTAGTTTTG  CCCCAGGTGC  ACGAAGCAAC  TGGCTCTAAG  AATTTCTTGA    4140

AAGACATATT  GATACTAGGC  ACTAGGCAAA  ATATAAGTTT  ATATGAAGTA  CATGTACCAG    4200

TACTTCAAAA  CATCACATCA  ATAAACAATT  CAACAAATAC  AGTACAGATT  CACATGGAGC    4260

ATTTCTTTAA  AGAAGGAAG   GACAAGGAAA  CAAATTCAGA  AGGCTTGGTA  AATAAAACCA    4320

GAGAAATGGT  AAAAAACTAT  CCAAGCCAGA  AGAATATTAC  TACTCAACGT  AGTAAACGGG    4380

CTTTGGGACA  ATTCAGACTG  TCAACTCAAT  GGCTTAAAAC  CATAAACTGT  CAACACAGT    4440

GTATCATTAA  ACAGATAGAC  CACAGCAAGG  AAATGAAAAA  GTTCATTACT  AAATCTTCCT    4500

TATCAGATTC  TTCTGTGATT  AAAAGCACCA  CTCAGACAAA  TAGTTCTGAC  TCACACATTG    4560

TAAAAACATC  AGCATTTCCA  CCAATAGATC  TCAAAAGGAG  TCCATTCCAA  AACAAATTTT    4620

CTCATGTTCA  AGCATCATCC  TACATTTATG  ACTTTAAGAC  AAAAAGTTCA  AGAATTCAAG    4680

AAAGCAATAA  TTTCTTAAAA  GAAACCAAAA  TAAATAACCC  TTCTTTAGCC  ATTCTACCAT    4740

GGAATATGTT  CATAGATCAA  GGAAAATTTA  CCTCCCCAGG  GAAAAGTAAC  ACAAACTCAG    4800

TCACATATAA  GAAACGTGAG  AACATTATTT  TCTTGAAACC  AACTTTGCCT  GAAGAATCTG    4860

GCAAAATTGA  ATTGCTTCCT  CAAGTTTCCA  TTCAAGAGGA  AGAAATTTTA  CCTACAGAAA    4920

CTAGCCATGG  ATCTCCTGGA  CACTTGAATC  TCATGAAAGA  GGTCTTTCTT  CAGAAAATAC    4980

AGGGGCCTAC  TAAATGGAAT  AAAGCAAAGA  GGCATGGAGA  AAGTATAAAA  GGTAAAACAG    5040

AGAGCTCTAA  AAATACTCGC  TCAAAACTGC  TAAATCATCA  TGCTTGGGAT  TATCATTATG    5100

CTGCACAGAT  ACCAAAAGAT  ATGTGGAAAT  CCAAAGAGAA  GTCACCAGAA  ATTATATCCA    5160

TTAAGCAAGA  GGACACCATT  TTGTCTCTGA  GGCCTCATGG  AAACAGTCAT  TCAATAGGGG    5220
```

```
CAAATGAGAA  ACAAAATTGG  CCTCAAAGAG  AAACCACTTG  GGTAAAGCAA  GGCCAAACTC   5280

AAAGGACATG  CTCTCAAATC  CCACCAGTGT  TGAAACGACA  TCAAAGGGAA  CTTAGTGCTT   5340

TTCAATCAGA  ACAAGAAGCA  ACTGACTATG  ATGATGCCAT  CACCATTGAA  ACAATCGAGG   5400

ATTTTGACAT  TTACAGTGAG  GACATAAAGC  AAGGTCCCCG  CAGCTTTCAA  CAGAAAACAA   5460

GGCACTATTT  TATTGCAGCT  GTGGAACGAC  TCTGGGACTA  TGGGATGAGT  ACATCTCATG   5520

TTCTACGAAA  TAGGTATCAA  AGTGACAATG  TACCTCAGTT  CAAGAAAGTA  GTTTTCCAGG   5580

AATTTACTGA  TGGCTCCTTT  AGTCAGCCCT  TATATCGTGG  AGAATTAAAT  GAACACCTGG   5640

GGTTGTTGGG  CCCATATATA  AGAGCAGAAG  TTGAAGACAA  CATTATGGTA  ACTTTCAAAA   5700

ACCAGGCCTC  CCGTCCCTAC  TCCTTCTATT  CTAGCCTCAT  TTCTTATAAA  GAAGATCAGA   5760

GAGGAGAAGA  ACCTAGAAGA  AACTTTGTCA  AGCCTAATGA  AACCAAAATT  TATTTTTGGA   5820

AAGTACAACA  TCATATGGCA  CCCACAGAAG  ATGAGTTTGA  CTGCAAGGCC  TGGGCTTATT   5880

TCTCTGATGT  TGATCTTGAA  AGAGATATGC  ACTCGGGATT  AATTGGACCC  CTTCTGATTT   5940

GCCACGCGAA  CACACTGAAT  CCTGCTCATG  GGAGACAAGT  GTCAGTACAG  GAATTTGCTC   6000

TGCTTTTCAC  TATCTTTGAT  GAGACCAAGA  GCTGGTACTT  CACTGAAAAC  GTGAAAAGGA   6060

ACTGCAAGAC  ACCCTGCAAT  TTCCAGATGG  AAGACCCCAC  TTTGAAAGAG  AATTATCGCT   6120

TCCATGCAAT  CAATGGTTAT  GTAATGGATA  CCCTACCAGG  CTTAGTAATG  GCTCAAGATC   6180

AAAGGATTCG  ATGGTATCTT  CTCAGCATGG  GCAACAATGA  GAACATCCAA  TCTATTCATT   6240

TCAGTGGACA  TGTTTTCACT  GTACGGAAAA  AAGAGGAGTA  TAAAATGGCA  GTGTACAACC   6300

TCTACCCAGG  TGTTTTTGAG  ACTCTGGAAA  TGATACCATC  CAGAGCTGGA  ATATGGCGAG   6360

TAGAATGCCT  TATTGGCGAG  CACTTACAGG  CTGGGATGAG  CACTCTTTTT  CTGGTGTACA   6420

GCAAGCAGTG  TCAGATTCCT  CTTGGAATGG  CTTCTGGAAG  CATCCGTGAT  TTCCAGATTA   6480

CAGCTTCAGG  ACATTATGGA  CAGTGGGCCC  CAAACCTGGC  AAGACTTCAT  TATTCCGGAT   6540

CAATCAATGC  CTGGAGTACC  AAGGAGCCCT  TTTCTTGGAT  CAAGGTAGAT  CTGTTGGCAC   6600

CAATGATTGT  TCATGGCATC  AAGACTCAGG  GTGCTCGTCA  GAAATTTTCC  AGCCTTTATA   6660

TCTCTCAATT  TATCATCATG  TATAGCCTGG  ATGGGAAGAA  GTGGCTGAGT  TATCAAGGAA   6720

ATTCCACTGG  AACCTTAATG  GTTTTCTTTG  GCAATGTGGA  CTCATCTGGG  ATTAAGCATA   6780

ATAGTTTTAA  TCCTCCAATT  ATTGCTCGAT  ATATCCGTTT  GCACCCCACT  CATTCTAGCA   6840

TCCGTAGTAC  TCTTCGCATG  GAGTTGATGG  GCTGTGATTT  AAACAGTTGC  AGCATACCAT   6900

TGGGAATGGA  AAGTAAAGTA  ATATCAGATA  CACAAATCAC  TGCCTCATCC  TACTTCACCA   6960

ACATGTTTGC  TACTTGGTCT  CCTTCACAAG  CTCGACTTCA  CCTCCAGGGA  AGGACTAATG   7020

CCTGGCGACC  TCAGGTGAAT  GATCCAAAAC  AATGGTTGCA  AGTGGACTTA  CAAAAGACAA   7080

TGAAAGTCAC  TGGAATAATA  ACCCAGGGAG  TGAAATCTCT  CTTTACCAGC  ATGTTTGTGA   7140

AAGAGTTCCT  TATTTCCAGC  AGTCAAGATG  GCCATCACTG  GACTCAAATT  TTATACAATG   7200

GCAAGGTAAA  GGTTTTTCAG  GGGAATCAGG  ACTCATCCAC  ACCTATGATG  AATTCTCTAG   7260

ACCCACCATT  ACTCACTCGC  TATCTTCGAA  TTCACCCCCA  GATCTGGGAG  CACCAAATTG   7320

CTCTGAGGCT  TGAGATTCTA  GGATGTGAGG  CCCAGCAGCA  ATACTGAGGT  AGCCTCTGCA   7380

TCACCTGCTT  ATTCCCCTTC  CTCAGCTCAA  AGATTGTCTT  AATGTTTTAT  TGCTGTGAAG   7440

AGACACTATG  ACCATGGCAA  CTCTTTATAA  AATAAAGCAT  TTAATCAGGG  CTT          7493
```

( 2 ) INFORMATION FOR SEQ ID NO:6:

( i ) SEQUENCE CHARACTERISTICS:
    ( A ) LENGTH: 2319 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: YES ( i v ) ANTI-SENSE: NO ( v ) FRAGMENT TYPE: N-terminal ( v i ) ORIGINAL SOURCE:
    ( A ) ORGANISM: Mus musculus ( x ) PUBLICATION INFORMATION:
    ( A ) AUTHORS: Elder, F.
                   Lakich, D.
                   Gitschier, J.
    ( B ) TITLE: Sequence of the Murine Factor VIII cDNA.
    ( C ) JOURNAL: Genomics
    ( D ) VOLUME: 16
    ( F ) PAGES: 374-379
    ( G ) DATE: 1993
    ( K ) RELEVANT RESIDUES IN SEQ ID NO:6: FROM 1 TO 2319

( x i ) SEQUENCE DESCRIPTION: SEQ ID NO:6:

```
Met Gln Ile Ala Leu Phe Ala Cys Phe Phe Leu Ser Leu Phe Asn Phe
1               5                   10                  15

Cys Ser Ser Ala Ile Arg Arg Tyr Tyr Leu Gly Ala Val Glu Leu Ser
            20                  25                  30

Trp Asn Tyr Ile Gln Ser Asp Leu Leu Ser Val Leu His Thr Asp Ser
                35              40                  45

Arg Phe Leu Pro Arg Met Ser Thr Ser Phe Pro Phe Asn Thr Ser Ile
        50              55                  60

Met Tyr Lys Lys Thr Val Phe Val Glu Tyr Lys Asp Gln Leu Phe Asn
65              70                  75                  80

Ile Ala Lys Pro Arg Pro Pro Trp Met Gly Leu Leu Gly Pro Thr Ile
                85              90                  95

Trp Thr Glu Val His Asp Thr Val Val Ile Thr Leu Lys Asn Met Ala
            100                 105                 110

Ser His Pro Val Ser Leu His Ala Val Gly Val Ser Tyr Trp Lys Ala
            115                 120                 125

Ser Glu Gly Asp Glu Tyr Glu Asp Gln Thr Ser Gln Met Glu Lys Glu
        130                 135                 140

Asp Asp Lys Val Phe Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Met Ser His Val Asp Leu Val Lys Asp Leu Asn Ser Gly Leu
            180                 185                 190

Ile Gly Ala Leu Leu Val Cys Lys Glu Gly Ser Leu Ser Lys Glu Arg
        195                 200                 205

Thr Gln Met Leu Tyr Gln Phe Val Leu Leu Phe Ala Val Phe Asp Glu
    210                 215                 220

Gly Lys Ser Trp His Ser Glu Thr Asn Asp Ser Tyr Thr Gln Ser Met
225                 230                 235                 240

Asp Ser Ala Ser Ala Arg Asp Trp Pro Lys Met His Thr Val Asn Gly
            245                 250                 255

Tyr Val Asn Arg Ser Leu Pro Gly Leu Ile Gly Cys His Arg Lys Ser
            260                 265                 270
```

-continued

| | | | | | | | | | | | | | | |
|---|---|---|---|---|---|---|---|---|---|---|---|---|---|---|
|Val|Tyr 275|Trp|His|Val|Ile 280|Gly|Met|Gly|Thr|Thr 285|Pro|Glu|Ile|His|Ser|
|Ile|Phe 290|Leu|Glu|Gly|His 295|Thr|Phe|Phe|Val|Arg 300|Asn|His|Arg|Gln|Ala|
|Ser 305|Leu|Glu|Ile|Ser|Pro 310|Ile|Thr|Phe|Leu|Thr 315|Ala|Gln|Thr|Leu|Leu 320|
|Ile|Asp|Leu|Gly|Gln 325|Phe|Leu|Leu|Phe|Cys 330|His|Ile|Ser|Ser|His 335|Lys|
|His|Asp|Gly|Met 340|Glu|Ala|Tyr|Val|Lys 345|Val|Asp|Ser|Cys|Pro 350|Glu|Glu|
|Ser|Gln|Trp 355|Gln|Lys|Lys|Asn|Asn 360|Asn|Glu|Glu|Met|Glu 365|Asp|Tyr|Asp|
|Asp|Asp 370|Leu|Tyr|Ser|Glu|Met 375|Asp|Met|Phe|Thr|Leu 380|Asp|Tyr|Asp|Ser|
|Ser 385|Pro|Phe|Ile|Gln|Ile 390|Arg|Ser|Val|Ala|Lys 395|Lys|Tyr|Pro|Lys|Thr 400|
|Trp|Ile|His|Tyr|Ile 405|Ser|Ala|Glu|Glu|Glu 410|Asp|Trp|Asp|Tyr|Ala 415|Pro|
|Ser|Val|Pro|Thr 420|Ser|Asp|Asn|Gly|Ser 425|Tyr|Lys|Ser|Gln|Tyr 430|Leu|Ser|
|Asn|Gly|Pro 435|His|Arg|Ile|Gly|Arg 440|Lys|Tyr|Lys|Lys|Val 445|Arg|Phe|Ile|
|Ala|Tyr 450|Thr|Asp|Glu|Thr|Phe 455|Lys|Thr|Arg|Glu|Thr 460|Ile|Gln|His|Glu|
|Ser|Gly 465|Leu|Leu|Gly|Pro 470|Leu|Leu|Tyr|Gly|Glu 475|Val|Gly|Asp|Thr|Leu 480|
|Leu|Ile|Ile|Phe|Lys 485|Asn|Gln|Ala|Ser|Arg 490|Pro|Tyr|Asn|Ile|Tyr 495|Pro|
|His|Gly|Ile|Thr 500|Asp|Val|Ser|Pro|Leu 505|His|Ala|Arg|Arg|Leu 510|Pro|Arg|
|Gly|Ile|Lys 515|His|Val|Lys|Asp|Leu 520|Pro|Ile|His|Pro|Gly 525|Glu|Ile|Phe|
|Lys|Tyr 530|Lys|Trp|Thr|Val|Thr 535|Val|Glu|Asp|Gly|Pro 540|Thr|Lys|Ser|Asp|
|Pro 545|Arg|Cys|Leu|Thr|Arg 550|Tyr|Tyr|Ser|Ser|Phe 555|Ile|Asn|Pro|Glu|Arg 560|
|Asp|Leu|Ala|Ser|Gly 565|Leu|Ile|Gly|Pro|Leu 570|Leu|Ile|Cys|Tyr|Lys 575|Glu|
|Ser|Val|Asp|Gln 580|Arg|Gly|Asn|Gln|Met 585|Met|Ser|Asp|Lys|Arg 590|Asn|Val|
|Ile|Leu|Phe 595|Ser|Ile|Phe|Asp|Glu 600|Asn|Gln|Ser|Trp|Tyr 605|Ile|Thr|Glu|
|Asn|Met|Gln 610|Arg|Phe|Leu|Pro|Asn 615|Ala|Ala|Lys|Thr|Gln 620|Pro|Gln|Asp|
|Pro|Gly 625|Phe|Gln|Ala|Ser|Asn 630|Ile|Met|His|Ser|Ile 635|Asn|Gly|Tyr|Val 640|
|Phe|Asp|Ser|Leu|Glu 645|Leu|Thr|Val|Cys|Leu 650|His|Glu|Val|Ala|Tyr 655|Trp|
|His|Ile|Leu|Ser 660|Val|Gly|Ala|Gln|Thr 665|Asp|Phe|Leu|Ser|Ile 670|Phe|Phe|
|Ser|Gly|Tyr 675|Thr|Phe|Lys|His|Lys 680|Met|Val|Tyr|Glu|Asp 685|Thr|Leu|Thr|
|Leu|Phe|Pro|Phe|Ser|Gly|Glu|Thr|Val|Phe|Met|Ser|Met|Glu|Asn|Pro|

-continued

|     |     |     | 690 |     |     |     | 695 |     |     |     | 700 |     |     |     |
| --- | --- | --- | --- | --- | --- | --- | --- | --- | --- | --- | --- | --- | --- | --- |
| Gly 705 | Leu | Trp | Val | Leu 710 | Gly | Cys | His | Asn | Ser 715 | Asp | Phe | Arg | Lys | Arg 720 |
| Met | Thr | Ala | Leu | Leu 725 | Lys | Val | Ser | Ser | Cys 730 | Asp | Lys | Ser | Thr | Ser Asp 735 |
| Tyr | Tyr | Glu | Glu 740 | Ile | Tyr | Glu | Asp | Ile 745 | Pro | Thr | Gln | Leu 750 | Val | Asn Glu |
| Asn | Asn | Val | Ile 755 | Asp | Pro | Arg | Ser 760 | Phe | Phe | Gln | Asn | Thr 765 | Asn | His Pro |
| Asn | Thr | Arg 770 | Lys | Lys | Lys | Phe 775 | Lys | Asp | Ser | Thr | Ile 780 | Pro | Lys | Asn Asp |
| Met 785 | Glu | Lys | Ile | Glu | Pro 790 | Gln | Phe | Glu | Glu | Ile 795 | Ala | Glu | Met | Leu Lys 800 |
| Val | Gln | Ser | Val | Ser 805 | Val | Ser | Asp | Met | Leu 810 | Met | Leu | Leu | Gly | Gln Ser 815 |
| His | Pro | Thr | Pro 820 | His | Gly | Leu | Phe | Leu 825 | Ser | Asp | Gly | Gln | Glu 830 | Ala Ile |
| Tyr | Glu | Ala 835 | Ile | His | Asp | Asp | His 840 | Ser | Pro | Asn | Ala | Ile 845 | Asp | Ser Asn |
| Glu | Gly 850 | Pro | Ser | Lys | Val | Thr 855 | Gln | Leu | Arg | Pro | Glu 860 | Ser | His | His Ser |
| Glu 865 | Lys | Ile | Val | Phe | Thr 870 | Pro | Gln | Pro | Gly | Leu 875 | Gln | Leu | Arg | Ser Asn 880 |
| Lys | Ser | Leu | Glu | Thr 885 | Thr | Ile | Glu | Val | Lys 890 | Trp | Lys | Lys | Leu | Gly Leu 895 |
| Gln | Val | Ser | Ser 900 | Leu | Pro | Ser | Asn | Leu 905 | Met | Thr | Thr | Thr | Ile 910 | Leu Ser |
| Asp | Asn | Leu 915 | Lys | Ala | Thr | Phe | Glu 920 | Lys | Thr | Asp | Ser | Ser 925 | Gly | Phe Pro |
| Asp | Met | Pro 930 | Val | His | Ser | Ser 935 | Ser | Lys | Leu | Ser | Thr 940 | Thr | Ala | Phe Gly |
| Lys 945 | Lys | Ala | Tyr | Ser | Leu 950 | Val | Gly | Ser | His | Val 955 | Pro | Leu | Asn | Ala Ser 960 |
| Glu | Glu | Asn | Ser | Asp 965 | Ser | Asn | Ile | Leu | Asp 970 | Ser | Thr | Leu | Met | Tyr Ser 975 |
| Gln | Glu | Ser | Leu 980 | Pro | Arg | Asp | Asn | Ile 985 | Leu | Ser | Ile | Glu | Asn 990 | Asp Arg |
| Leu | Leu | Arg 995 | Glu | Lys | Arg | Phe | His 1000 | Gly | Ile | Ala | Leu | Leu 1005 | Thr | Lys Asp |
| Asn | Thr | Leu 1010 | Phe | Lys | Asp | Asn | Val 1015 | Ser | Leu | Met | Lys | Thr 1020 | Asn | Lys Thr |
| Tyr 1025 | Asn | His | Ser | Thr | Thr 1030 | Asn | Glu | Lys | Leu | His 1035 | Thr | Glu | Ser | Pro Thr 1040 |
| Ser | Ile | Glu | Asn | Ser 1045 | Thr | Thr | Asp | Leu | Gln 1050 | Asp | Ala | Ile | Leu | Lys Val 1055 |
| Asn | Ser | Glu | Ile 1060 | Gln | Glu | Val | Thr | Ala 1065 | Leu | Ile | His | Asp | Gly 1070 | Thr Leu |
| Leu | Gly | Lys | Asn 1075 | Ser | Thr | Tyr | Leu 1080 | Arg | Leu | Asn | His | Met 1085 | Leu | Asn Arg |
| Thr | Thr | Ser 1090 | Thr | Lys | Asn | Lys 1095 | Asp | Ile | Phe | His | Arg 1100 | Lys | Asp | Glu Asp |
| Pro 1105 | Ile | Pro | Gln | Asp | Glu 1110 | Glu | Asn | Thr | Ile | Met 1115 | Pro | Phe | Ser | Lys Met 1120 |

```
Leu Phe Leu Ser Glu Ser Ser Asn Trp Phe Lys Lys Thr Asn Gly Asn
            1125                1130                1135
Asn Ser Leu Asn Ser Glu Gln Glu His Ser Pro Lys Gln Leu Val Tyr
            1140                1145                1150
Leu Met Phe Lys Lys Tyr Val Lys Asn Gln Ser Phe Leu Ser Glu Lys
            1155                1160                1165
Asn Lys Val Thr Val Glu Gln Asp Gly Phe Thr Lys Asn Ile Gly Leu
            1170                1175                1180
Lys Asp Met Ala Phe Pro His Asn Met Ser Ile Phe Leu Thr Thr Leu
1185            1190                1195                    1200
Ser Asn Val His Glu Asn Gly Arg His Asn Gln Glu Lys Asn Ile Gln
            1205                1210                1215
Glu Glu Ile Glu Lys Glu Ala Leu Ile Glu Glu Lys Val Val Leu Pro
            1220                1225                1230
Gln Val His Glu Ala Thr Gly Ser Lys Asn Phe Leu Lys Asp Ile Leu
            1235                1240                1245
Ile Leu Gly Thr Arg Gln Asn Ile Ser Leu Tyr Glu Val His Val Pro
            1250                1255                1260
Val Leu Gln Asn Ile Thr Ser Ile Asn Asn Ser Thr Asn Thr Val Gln
1265            1270                1275                    1280
Ile His Met Glu His Phe Phe Lys Arg Arg Lys Asp Lys Glu Thr Asn
            1285                1290                1295
Ser Glu Gly Leu Val Asn Lys Thr Arg Glu Met Val Lys Asn Tyr Pro
            1300                1305                1310
Ser Gln Lys Asn Ile Thr Thr Gln Arg Ser Lys Arg Ala Leu Gly Gln
            1315                1320                1325
Phe Arg Leu Ser Thr Gln Trp Leu Lys Thr Ile Asn Cys Ser Thr Gln
            1330                1335                1340
Cys Ile Ile Lys Gln Ile Asp His Ser Lys Glu Met Lys Lys Phe Ile
1345            1350                1355                    1360
Thr Lys Ser Ser Leu Ser Asp Ser Ser Val Ile Lys Ser Thr Thr Gln
            1365                1370                1375
Thr Asn Ser Ser Asp Ser His Ile Val Lys Thr Ser Ala Phe Pro Pro
            1380                1385                1390
Ile Asp Leu Lys Arg Ser Pro Phe Gln Asn Lys Phe Ser His Val Gln
            1395                1400                1405
Ala Ser Ser Tyr Ile Tyr Asp Phe Lys Thr Lys Ser Ser Arg Ile Gln
            1410                1415                1420
Glu Ser Asn Asn Phe Leu Lys Glu Thr Lys Ile Asn Asn Pro Ser Leu
1425            1430                1435                    1440
Ala Ile Leu Pro Trp Asn Met Phe Ile Asp Gln Gly Lys Phe Thr Ser
            1445                1450                1455
Pro Gly Lys Ser Asn Thr Asn Ser Val Thr Tyr Lys Lys Arg Glu Asn
            1460                1465                1470
Ile Ile Phe Leu Lys Pro Thr Leu Pro Glu Glu Ser Gly Lys Ile Glu
            1475                1480                1485
Leu Leu Pro Gln Val Ser Ile Gln Glu Glu Glu Ile Leu Pro Thr Glu
            1490                1495                1500
Thr Ser His Gly Ser Pro Gly His Leu Asn Leu Met Lys Glu Val Phe
1505            1510                1515                    1520
Leu Gln Lys Ile Gln Gly Pro Thr Lys Trp Asn Lys Ala Lys Arg His
            1525                1530                1535
Gly Glu Ser Ile Lys Gly Lys Thr Glu Ser Ser Lys Asn Thr Arg Ser
            1540                1545                1550
```

```
Lys Leu Leu Asn His His Ala Trp Asp Tyr His Tyr Ala Ala Gln Ile
        1555                1560                1565

Pro Lys Asp Met Trp Lys Ser Lys Glu Lys Ser Pro Glu Ile Ile Ser
        1570                1575                1580

Ile Lys Gln Glu Asp Thr Ile Leu Ser Leu Arg Pro His Gly Asn Ser
1585                1590                1595                1600

His Ser Ile Gly Ala Asn Glu Lys Gln Asn Trp Pro Gln Arg Glu Thr
            1605                1610                1615

Thr Trp Val Lys Gln Gly Gln Thr Gln Arg Thr Cys Ser Gln Ile Pro
        1620                1625                1630

Pro Val Leu Lys Arg His Gln Arg Glu Leu Ser Ala Phe Gln Ser Glu
        1635                1640                1645

Gln Glu Ala Thr Asp Tyr Asp Asp Ala Ile Thr Ile Glu Thr Ile Glu
        1650                1655                1660

Asp Phe Asp Ile Tyr Ser Glu Asp Ile Lys Gln Gly Pro Arg Ser Phe
1665                1670                1675                1680

Gln Gln Lys Thr Arg His Tyr Phe Ile Ala Ala Val Glu Arg Leu Trp
            1685                1690                1695

Asp Tyr Gly Met Ser Thr Ser His Val Leu Arg Asn Arg Tyr Gln Ser
        1700                1705                1710

Asp Asn Val Pro Gln Phe Lys Lys Val Val Phe Gln Glu Phe Thr Asp
        1715                1720                1725

Gly Ser Phe Ser Gln Pro Leu Tyr Arg Gly Glu Leu Asn Glu His Leu
        1730                1735                1740

Gly Leu Leu Gly Pro Tyr Ile Arg Ala Glu Val Glu Asp Asn Ile Met
1745                1750                1755                1760

Val Thr Phe Lys Asn Gln Ala Ser Arg Pro Tyr Ser Phe Tyr Ser Ser
            1765                1770                1775

Leu Ile Ser Tyr Lys Glu Asp Gln Arg Gly Glu Glu Pro Arg Arg Asn
        1780                1785                1790

Phe Val Lys Pro Asn Glu Thr Lys Ile Tyr Phe Trp Lys Val Gln His
        1795                1800                1805

His Met Ala Pro Thr Glu Asp Glu Phe Asp Cys Lys Ala Trp Ala Tyr
    1810                1815                1820

Phe Ser Asp Val Asp Leu Glu Arg Asp Met His Ser Gly Leu Ile Gly
1825                1830                1835                1840

Pro Leu Leu Ile Cys His Ala Asn Thr Leu Asn Pro Ala His Gly Arg
                1845                1850                1855

Gln Val Ser Val Gln Glu Phe Ala Leu Leu Phe Thr Ile Phe Asp Glu
            1860                1865                1870

Thr Lys Ser Trp Tyr Phe Thr Glu Asn Val Lys Arg Asn Cys Lys Thr
        1875                1880                1885

Pro Cys Asn Phe Gln Met Glu Asp Pro Thr Leu Lys Glu Asn Tyr Arg
        1890                1895                1900

Phe His Ala Ile Asn Gly Tyr Val Met Asp Thr Leu Pro Gly Leu Val
1905                1910                1915                1920

Met Ala Gln Asp Gln Arg Ile Arg Trp Tyr Leu Leu Ser Met Gly Asn
                1925                1930                1935

Asn Glu Asn Ile Gln Ser Ile His Phe Ser Gly His Val Phe Thr Val
            1940                1945                1950

Arg Lys Lys Glu Glu Tyr Lys Met Ala Val Tyr Asn Leu Tyr Pro Gly
        1955                1960                1965

Val Phe Glu Thr Leu Glu Met Ile Pro Ser Arg Ala Gly Ile Trp Arg
```

|  | 1970 | | | | 1975 | | | | | 1980 | | | | |
|---|---|---|---|---|---|---|---|---|---|---|---|---|---|---|

Val Glu Cys Leu Ile Gly Glu His Leu Gln Ala Gly Met Ser Thr Leu
1985                          1990                          1995                          2000

Phe Leu Val Tyr Ser Lys Gln Cys Gln Ile Pro Leu Gly Met Ala Ser
                2005                          2010                          2015

Gly Ser Ile Arg Asp Phe Gln Ile Thr Ala Ser Gly His Tyr Gly Gln
                2020                          2025                          2030

Trp Ala Pro Asn Leu Ala Arg Leu His Tyr Ser Gly Ser Ile Asn Ala
                2035                          2040                          2045

Trp Ser Thr Lys Glu Pro Phe Ser Trp Ile Lys Val Asp Leu Leu Ala
                2050                          2055                          2060

Pro Met Ile Val His Gly Ile Lys Thr Gln Gly Ala Arg Gln Lys Phe
2065                          2070                          2075                          2080

Ser Ser Leu Tyr Ile Ser Gln Phe Ile Ile Met Tyr Ser Leu Asp Gly
                2085                          2090                          2095

Lys Lys Trp Leu Ser Tyr Gln Gly Asn Ser Thr Gly Thr Leu Met Val
                2100                          2105                          2110

Phe Phe Gly Asn Val Asp Ser Ser Gly Ile Lys His Asn Ser Phe Asn
                2115                          2120                          2125

Pro Pro Ile Ile Ala Arg Tyr Ile Arg Leu His Pro Thr His Ser Ser
                2130                          2135                          2140

Ile Arg Ser Thr Leu Arg Met Glu Leu Met Gly Cys Asp Leu Asn Ser
2145                          2150                          2155                          2160

Cys Ser Ile Pro Leu Gly Met Glu Ser Lys Val Ile Ser Asp Thr Gln
                2165                          2170                          2175

Ile Thr Ala Ser Ser Tyr Phe Thr Asn Met Phe Ala Thr Trp Ser Pro
                2180                          2185                          2190

Ser Gln Ala Arg Leu His Leu Gln Gly Arg Thr Asn Ala Trp Arg Pro
                2195                          2200                          2205

Gln Val Asn Asp Pro Lys Gln Trp Leu Gln Val Asp Leu Gln Lys Thr
                2210                          2215                          2220

Met Lys Val Thr Gly Ile Ile Thr Gln Gly Val Lys Ser Leu Phe Thr
2225                          2230                          2235                          2240

Ser Met Phe Val Lys Glu Phe Leu Ile Ser Ser Ser Gln Asp Gly His
                2245                          2250                          2255

His Trp Thr Gln Ile Leu Tyr Asn Gly Lys Val Lys Val Phe Gln Gly
                2260                          2265                          2270

Asn Gln Asp Ser Ser Thr Pro Met Met Asn Ser Leu Asp Pro Pro Leu
                2275                          2280                          2285

Leu Thr Arg Tyr Leu Arg Ile His Pro Gln Ile Trp Glu His Gln Ile
                2290                          2295                          2300

Ala Leu Arg Leu Glu Ile Leu Gly Cys Glu Ala Gln Gln Gln Tyr
                2305                          2310                          2315

( 2 ) INFORMATION FOR SEQ ID NO:7:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:7:

CCTTCCTTTA TCCAAATACG TAGATCAAGA GGAAATTGAC 40

( 2 ) INFORMATION FOR SEQ ID NO:8:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:8:

GTAGCGTTGC CAAGAAGCAC CCTAAGACG 29

( 2 ) INFORMATION FOR SEQ ID NO:9:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:9:

GAAGAGTAGT ACGAGTTATT TCTCTGGGTT CAATGAC 37

( 2 ) INFORMATION FOR SEQ ID NO:10:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:10:

CCTTTATCCA AATACGTAGC GTTTGCCAAG AAG 33

( 2 ) INFORMATION FOR SEQ ID NO:11:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:11:

AARCAYCCNA ARACNTGGG 19

(2) INFORMATION FOR SEQ ID NO:12:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: Other nucleic acid (iii) HYPOTHETICAL: NO (iv) ANTI-SENSE: NO (xi) SEQUENCE DESCRIPTION: SEQ ID NO:12:

GCTCGCACTA GGGGGTCTTG AATTC                                        25